US011850249B2

(12) United States Patent
Shah et al.

(10) Patent No.: US 11,850,249 B2
(45) Date of Patent: *Dec. 26, 2023

(54) METHODS OF EFFICIENTLY REDUCING INTRAOCULAR PRESSURE

(71) Applicant: Somerset Therapeutics, LLC, Hollywood, FL (US)

(72) Inventors: Mandar V. Shah, Rockaway, NJ (US); Ilango Subramanian, Warren, NJ (US); Veerappan Subramanian, Warren, NJ (US); Aman Trehan, Hillsborough, NJ (US)

(73) Assignee: Somerset Therapeutics, LLC, Hollywood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/494,681

(22) Filed: Oct. 5, 2021

(65) Prior Publication Data

US 2022/0105102 A1 Apr. 7, 2022

Related U.S. Application Data

(60) Provisional application No. 63/087,657, filed on Oct. 5, 2020.

(51) Int. Cl.
| | | |
|---|---|---|
| *A61K 31/542* | (2006.01) | |
| *A61K 31/498* | (2006.01) | |
| *A61K 9/00* | (2006.01) | |
| *A61K 47/02* | (2006.01) | |
| *A61K 47/10* | (2017.01) | |
| *A61K 47/18* | (2017.01) | |
| *A61K 9/08* | (2006.01) | |
| *A61K 47/32* | (2006.01) | |
| *A61K 47/34* | (2017.01) | |

(52) U.S. Cl.
CPC .......... *A61K 31/542* (2013.01); *A61K 9/0048* (2013.01); *A61K 9/08* (2013.01); *A61K 31/498* (2013.01); *A61K 47/02* (2013.01); *A61K 47/10* (2013.01); *A61K 47/186* (2013.01); *A61K 47/32* (2013.01); *A61K 47/34* (2013.01)

(58) Field of Classification Search
CPC .... A61K 31/498; A61K 31/542; A61K 47/02; A61K 47/10; A61K 47/12; A61K 47/186; A61K 47/26; A61K 47/32; A61K 47/34; A61K 9/0048; A61K 9/08
See application file for complete search history.

(56) References Cited

U.S. PATENT DOCUMENTS

| | | | |
|---|---|---|---|
| 5,378,703 A | 1/1995 | Dean et al. | |
| 6,071,904 A | 6/2000 | Ali et al. | |
| 6,242,442 B1 | 6/2001 | Dean | |
| 6,316,441 B1 | 11/2001 | Dean et al. | |
| 9,044,484 B2 | 6/2015 | Kabra | |
| 9,421,265 B2 | 8/2016 | Kabra | |
| 2010/0144719 A1 | 6/2010 | Kabra | |
| 2010/0324031 A1 | 12/2010 | Kabra | |
| 2013/0065888 A1 | 3/2013 | Cetina-Cizmek | |
| 2014/0378401 A1* | 12/2014 | Horn | A61K 31/4439 514/249 |
| 2015/0366854 A1 | 12/2015 | Ostrow | |
| 2021/0369728 A1* | 12/2021 | Jesudian | A61K 31/542 |

FOREIGN PATENT DOCUMENTS

| | | | | |
|---|---|---|---|---|
| WO | WO-2016063184 A1 * | 4/2016 | ......... | A61K 31/5377 |
| WO | WO 2019/091596 | 5/2019 | | |

OTHER PUBLICATIONS

Alphagan Label, Reference ID:3906086, Revised Mar. 2016.
Azopt Label, Reference ID: 3843548, Revised Jul. 2015.
Baudouin C et. al., "Preservatives in eyedrops: The good, the bad and the ugly," Progress in Retinal and Eye Research, 29 (2010) 312-334.
ClinicalTrials.gov, Identifier NCT0131077, "Brinzolamide/Brimonidine Twice a Day (BID) Fixed Combination (FC) vs Brinzolamide BID and Brimonidine BID in Patients with Open Angle Glaucoma or Ocular Hypertension". Completed. ast Updated Posted Mar. 6, 2014.
Goldstein, et al., "Ocular benzalkonium chloride exposure: problems and solutions," Royal College of Ophthalmologists, published via nature.com/eye online Jul. 14, 2021.
Nguyen, "Combination of brinzolamide and brimonidine for glaucoma and ocular hypertension: critical appraisal and patient focus," Patient Preference and Adherence; 2014; 8: 853-864.
Simbrinza Label, Reference ID: 3296143, Revised Apr. 2013.

(Continued)

*Primary Examiner* — Sarah Pihonak
(74) *Attorney, Agent, or Firm* — Transformative Legal LLC; Len S. Smith; Julie E. Kurzrok

(57) ABSTRACT

Disclosed herein are pharmacologically acceptable and ophthalmologically suitable compositions and methods of their use in treating ophthalmic diseases or related conditions. In aspects, the invention provides compositions comprising effective amounts of carbonic anhydrase inhibitor(s) and alpha-2-adrenergic agonist(s). In facets, compositions comprise a penetration enhancer component comprising one or more penetration enhancer compound(s)/molecule(s). In aspects, the invention provides compositions comprising effective amounts of brimonidine compound(s) and brinzolamide compound(s) capable of being administered once or twice daily for the treatment of elevated intraocular pressure, but which provide similar efficacy to a similar or substantially identical reference product requiring administration three times per day. In facets, the invention provides compositions capable of being administered at a frequency resulting in providing a lower total dose of both brinzolamide and brimonidine compound(s) to a recipient, but nonetheless are as or more effective in IOP control as such similar or substantially identical reference products.

14 Claims, No Drawings

(56) References Cited

OTHER PUBLICATIONS

European Medicines Agency, "EMEA Public Statement on Antimicrobial Preservatives in Ophthalmic Preparations for Human Use", Dec. 8, 2009, Doc. Ref: EMEA622721/2009.
Pharmaceutical Practice, Third Edition. 2004, Jan. 1, 2004, Winfield, A.J.
Non-Final Office Action dated Jul. 7, 2022 for U.S. Appl. No. 17/494,663, Jul. 7, 2022, Thomas, Timothy P.
Rowe et al., Benzalkonium chloride, Handbook of Pharmaceutical Excipients, 2009, Sixth Edition, Pharmacuetical Press, 56-58, Jan. 15, 2009, Rowe, Raymond C.
Okabe et al., Effect of benzalkonium chloride on transscleral drug delivery, Invest Opththalmol Vis Sci., Feb. 2005; 46(2): 703-8, printed from https://pubmed.ncbi.nih.gov/15671302/, 2 pages, abstract only, Feb. 1, 2005, Okabe, Kobei.
Lederer et al, Drop size of commercial medications. Doi: 10.1016/0002-9394(86)90771-3, Jun. 15, 1986, Lederer, Charles M.
Final Office Action dated Sep. 9, 2022 for U.S. Appl. No. 17/494,635, Sep. 9, 2022, Huang, Gigi Georgiana.
Non-Final Office Action dated May 4, 2022 for U.S. Appl. No. 17/494,635, May 4, 2022, Huang, Gigi Georgiana.
Final Office Action dated Jul. 6, 2022 for U.S. Appl. No. 17/494,713, Jul. 6, 2022, Huang, Gigi Georgiana.
Non-Final Office Action dated Mar. 7, 2022 for U.S. Appl. No. 17/494,713, Mar. 7, 2022, Huang, Gigi Georgiana.
Fechtner, Ocular hypotensive effect of fixed-combination brinzolarnide/brirnonidine adjunctive to a prostaglandin analog; a randomized clinical trial. doi: 10.1038/eye.2016.126, Jul. 1, 2016, Fechtner, Robert D.
Thickening Properties. Pharmaceutical Bulletin. May 2011, May 31, 2011, Corporation, Lubrizol.
Malhotra et al., Permeation through cornea, Indian J Exp Biol. Jan. 2001; 39(1):11-24.
Non-Final Office Action dated Nov. 1, 2022 for U.S. Appl. No. 17/494,713.
Vo et al. ("Factors affecting the particle size distribution and rheology of brinzolamide ophthalmic suspensions"; 20; pp. 1-1120 Jun. 14; International Journal of Pharmaceutics 586 (2020) 119495; pp. 1-11; https://doi.org/10.1016/j.jpharm.2020.119495 (Year: 2020).
Lubrizol (Pharmaceutical Bulletin 6; Thickening Properties; 2011; https://www.lubrizol.com/-/media/Lubrizol/Health/Literature/Bulletin-06-Thickening-Properties.pdf (Year: 2011).
Final Office Action dated Nov. 25, 2022 for U.S. Appl. No. 17/494,663.

\* cited by examiner

METHODS OF EFFICIENTLY REDUCING INTRAOCULAR PRESSURE

CROSS REFERENCE TO RELATED APPLICATIONS

This patent Application claims priority to U.S. Provisional Patent Application No. 63/087,657 filed Oct. 5, 2020, entitled "Brinzolamide and Brimonidine Ophthalmic Composition". This Application claims the benefit of priority to, and incorporates by reference the entirety of, this above-referenced priority application.

FIELD OF THE INVENTION

The invention primarily relates to the field of topical compositions and methods of their use in reducing elevated intraocular pressure and other ophthalmic conditions.

BACKGROUND OF THE INVENTION

About 10 out of every 100 people over the age of 40 years of age suffer from elevated intraocular pressure (IOP). A subset of this population experiences elevated IOP, or ocular hypertension, in association with glaucoma, most commonly open-angle glaucoma. Left untreated, ocular hypertension can itself lead to glaucoma, as increased ocular pressure can cause erosion of the optic nerve. Often times such erosion of the optic nerve leads to vision loss and even blindness. Glaucoma and its associated elevated IOP is a condition requiring chronic treatment, typically using topically applied products such as products delivered by eye drops.

Brinzolamide is a carbonic anhydrase inhibitor known for its use in treating elevated IOP such as that associated with glaucoma, e.g., open-angle glaucoma, and is found in a number of commercially available eye drop products. U.S. Pat. Nos. 5,378,703 and 6,071,904 disclose brinzolamide or salts thereof as carbonic anhydrase inhibitors and preparation of brinzolamide ophthalmic compositions, respectively. Similarly, brimonidine, a potent and relatively selective α-2-agonist (α-2-adrenergic-agonist), specifically the tartrate salt of brimonidine (brimonidine tartrate), is also known for its efficacy in reducing intraocular pressure. Brimonidine, too, is found in a number of commercially available eye drop products.

Azopt® (Alcon Laboratories, Inc.) is a United States Food and Drug Administration (US FDA) approved ophthalmic suspension product comprising 1% brinzolamide and 0.01% benzalkonium chloride for the indication elevated intraocular pressure in patients with ocular hypertension or open-angle glaucoma. Azopt® is administered according to an administration protocol comprising administration of one drop of Azopt® into affected eye(s) three times daily.

Alphagan® (Allergan, Inc.) is a US FDA approved ophthalmic solution product comprising 0.2% brimonidine tartrate, indicated for the reduction of elevated IOP in patients with open-angle glaucoma or ocular hypertension. Like Azopt®, the administration protocol for Alphagan® comprises administration of one drop in the affected eye three times daily, approximately 8 hours apart. Brimonidine tartrate is known for its somewhat significant side effects. According to the Alphagan® label, between 10% and 30% of patients receiving brimonidine ophthalmic solution (0.2%) experienced adverse events including oral dryness, ocular hyperemia, burning and stinging, headache, blurring, foreign body sensation, fatigue/drowsiness, conjunctival follicles, ocular allergic reactions, and ocular pruritus. Notably, brimonidine does not appear to be a vasoconstrictor in vessels in the back of the eye. In addition to the noted side effects including sedation, an effect theorized to be caused by the drug crossing the blood brain barrier, another known side effect of brimonidine is ocular hyperemia (e.g., in an allergic-like reaction) in some patients. The mechanism by which brimonidine causes hyperemia is not well understood.

As monotherapy may be insufficient to successfully treat elevated IOP, multidrug regimens have been proposed. However, as described in, e.g., Nguyen, "Combination of brinzolamide and brimonidine for glaucoma and ocular hypertension: critical appraisal and patient focus," (Patient Prefer Adherence; 2014; 8: 853-864), multidrug regimens can be complex and introduce significant risks, such as preservative-related effects and may potentially reduce overall drug exposure as a consequence of drug washout during closely timed sequential administration. For example, when Azopt® is used with one or more topical ophthalmic drug products, such as with Alphagan®, the products must be administered at least 10 minutes apart, in a particular order; e.g., with brimonidine administered first to constrict ocular vessels and reduce the flux of blood through the anterior portion of the eye, followed by brinzolamide, wherein the reduced circulation in the eye lends itself in an increase in the bioavailability of the CAI, its efficacy, and the duration of action(s).

Simbrinza® (Alcon Laboratories, Inc.) is a topically applied ophthalmic suspension product comprising 1% brinzolamide and 0.2% brimonidine, initially approved by the US FDA under NDA #204251 in April of 2013. United States patent numbers 9044484 ("US '484") and related U.S. Pat. No. 9,421,265 ("US '265") are listed in the FDA Orange Book in association with Simbrinza®. These patents disclose compositions comprising a combination of brinzolamide and brimonidine, compositions comprising borate-polyol complexes, compositions comprising use of two different polyols, and compositions comprising low amounts of benzalkonium chloride, specifically amounts of benzalkonium chloride greater than 0.00001 w/v. % but less than 0.0035 w/v. %, apparently without inclusion of any chelating agent.

Effective treatment with Simbrinza® requires 1 drop to be administered per affected eye three times per day. Given the high risk of adverse events known to occur with administration of brimonidine tartrate, and, e.g., because of the above-described administration challenges of individually administered products, ophthalmology companies/scientists have attempted for some time to reduce dosing of related ophthalmic formulations, but without any success leading to a change in the standard of care for such patients.

For example, U.S. Pat. No. 6,316,441 ("US '441") discloses compositions and methods for treating ocular conditions having an etiology related to compromised ocular blood flow with brinzolamide and brimonidine and including other excipients, such as a chelating agents and benzalkonium chloride. Such disclosure includes fixed dose combinations of brinzolamide and brimonidine along with higher amounts of benzalkonium chloride than is present in Simbrinza®, including 0.005 w/v. % and 0.01 w/v. %. While this disclosure dates back to December 1995 and the technology disclosed therein was filed by Alcon Manufacturing, Ltd. (the same, leading ophthalmology company that received FDA approval for Simbrinza®), no currently available product appears to exist that incorporates/employs the teachings of this disclosure, suggesting that such a composition met significant challenges in moving from animal studies (e.g., cat and rabbit data from which is disclosed in US '441) to human application(s).

Data available on clinicaltrials.gov (ClinicalTrials.gov Identifier NCT0131077) indicate that a phase 3 clinical trial was completed by Alcon in 2013, which investigated the efficacy of 1 drop of a 1% brinzolamide and 0.2% brimonidine tartrate 0.2% ophthalmic suspension administered twice per day compared to 1% brinzolamide alone and 0.2% brimonidine tartrate alone administered according to the same schedule. The primary indication/endpoint of the study was mean diurnal IOP change from baseline at month 3. However, this study did not lead to any new product or change in standard of care, suggesting that problems encountered in or after the study impeded any further development of such products. Also, notably, there did not appear to be any report of any head-to-head comparison between the approved three-times-a-day administration method of Simbrinza® and any such proposed or other twice daily administration method.

It is noteworthy that US '441 discloses the use of higher concentrations of benzalkonium chloride than what is present in Simbrinza®. In the years between the disclosure of US '441 and present, the art has generally directed product developers away from the use of benzalkonium chloride in ophthalmology products. For example, Baudouin C et. al., in Prog Retin Eye Res. 2010 July; 29(4)312-34 discloses a pattern of consistent ophthalmological side effects in laboratory, experimental, and clinical studies, including causing tear film instability, loss of goblet cells, conjunctival squamous metaplasia and apoptosis, disruption of the corneal epithelium barrier, and damage to deeper ocular tissues, in association with the use of benzalkonium chloride. Such data led authors to conclude that, "Care should be taken to avoid the long-term use of preservatives, otherwise a less toxic alternative to benzalkonium chloride should be developed, as this weakly allergenic but highly toxic compound exerts dose- and time-dependent effects." The authors further reported, "On the basis of all these experimental and clinical reports, it would be advisable to use benzalkonium-free solutions whenever possible." Patients can experience hypersensitivity reactions with BKC (benzalkonium chloride) and BKC may be absorbed by soft contact lenses creating challenges for contact lens users. In 2009, the European Medicines Agency's Committee for Medicinal Products for Human Use concluded that unpreserved formulations " . . . are needed for those patients who to not tolerate eye drops with preservatives. In addition, for long term treatment, formulations without preservatives are considered to be valuable alternatives." And a decade later, such directives continue. See, e.g., the July 2021 review article by Goldstein, et. al. (Royal College of Ophthalmologists, published via nature.com/eye) entitled, "Ocular benzalkonium chloride exposure: problems and solutions," wherein the authors review the cytotoxic and clinical effects of benzalkonium chloride on the ocular surface and discuss existing and emerging options for ocular disease management that can minimize or eliminate benzalkonium chloride exposure. These authors cite well over 10 studies demonstrating cytotoxic effects of benzalkonium chloride on ocular tissues. The concern over the use of BKC may serve to at least partly explain why the products described in US '441 were ultimately not developed.

From the foregoing it can be seen that the development of new treatments that are as or more effective than the current standard of care will require inventive ingenuity.

CONSTRUCTION, TERMS, AND ACRONYMS

This section offers guidelines for reading this disclosure. The intended audience for this disclosure ("readers") are persons having ordinary skill in the practice of technologies discussed or used herein. Readers may also be called "skilled persons," and such technologies called "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention ("aspects") ("cases," "facets," or "embodiments"). The invention encompasses all aspects, as described individually and as can be arrived at by any combination of such individual aspects. The breadth and scope of the invention should not be limited by any exemplary embodiments. No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here generally have the same meanings as commonly understood by skilled persons, regardless of any narrower examples or descriptions provided here (including any term introduced initially in quotations). However, aspects characterized by the inclusion of elements, steps, etc., associated with specific descriptions provided here are distinct embodiments of the invention. Uncontradicted, disclosure of any aspect using known terms, which terms are narrowed by example or otherwise in this disclosure, implicitly discloses related aspects in which such terms are alternatively interpreted using the broadest reasonable interpretation of skilled persons.

Uncontradicted, "or" means "and/or" here, regardless of any occasional inclusion of "and/or" (e.g., phrases such as "A, B, or C" and "A, B, and/or C" simultaneously disclose aspects including (1) all of A, B, and C; (2) A and C; (3) A and B; (4) B and C; (5) only A; (6) only B; and (7) only C (and also support sub-groupings, such as "A or B," "A or C," etc.)).

Uncontradicted, "also" means "also or alternatively." Uncontradicted, "here" and "herein" mean "in this disclosure." The abbreviation "i.a." ("ia" or "ia") means "inter alia" or "among other things." "Also known as" is abbreviated "aka" or "AKA." AKA also can mean "otherwise referred to as." "Elsewhere" means "elsewhere herein."

For conciseness, symbols are used where appropriate. E.g., "&" is used for "and," & "~" for "about." Symbols such as < and > are given their ordinary meaning (e.g., "≤" means "less than or equal to" & "≥" means "greater than or equal to"). A slash "/" can represent "or" ("A/B" means "A or B") or identify synonyms of an element, as will be clear from context.

The inclusion of "(s)" after an element or a step indicates that ≥1 of such an element is present, step performed, and the like. E.g., "element(s)" means both 1 element or ≥2 elements, with the understanding that each thereof is an independent aspect of the invention.

Use of the abbreviation "etc." (or "et cetera") in association with a list of elements/steps means any or all suitable combinations of the recited elements/steps or any known equivalents of such recited elements/steps for achieving the function(s) of such elements/steps that are known in the art. Uncontradicted, the phrase "and the like" is construed similarly. Terms such as "and combinations," or "or combinations" regarding listed elements/steps means combinations of any or all such elements/steps. "Suitability" means acceptable or appropriate for performing a particular function/achieving particular state(s)/outcome(s), and typically means effective, practical, and non-deleterious/harmful in the context the term is used. The term "suitable" is interpreted in a similar manner. More particular information concerning the suitability of certain elements or steps may be provided below.

Uncontradicted, heading(s) (e.g., "Construction, Terms . . . ") and subheadings in this disclosure are included for convenience and do not limit the scope of any aspect(s), claim(s), etc. Uncontradicted, aspect(s), step(s), or element(s) described under one heading can apply to any other aspect(s) or step(s)/element(s) provided in any other part of this disclosure.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593).

Terms of approximation (e.g., "about," "~," or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10-about 20"). The scope of value(s) encompassed by an approximate term typically depends on the context of the disclosure, criticality or operability, statistical significance, understanding in the art, etc. In the absence of guidance here or in the art, terms such as "about" should be interpreted as +/−10% of the indicated value(s).

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of a single element/step implicitly discloses corresponding use of a plurality of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys."

"Significant" and "significantly" mean results/characteristics that are statistically significant using ≥1 appropriate test(s)/trial(s) in the given context (e.g., $p \leq 0.05/0.01$). "Detectable" means measurably present/different using known detection tools/techniques. The acronym "DOS" (or "DoS") means "detectable(ly) or significant(ly)."

Uncontradicted, for any value here that is not accompanied by a unit of measurement (e.g., a weight of 50 or a length of 20), any previously provided unit for the same element/step or the same type of element/step will apply, or, in cases where no such disclosure exists, the unit most commonly used in association with such an element/step in the art applies.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps).

For conciseness, description of an aspect "comprising" or "including" an element, with respect to a collection/whole (e.g., a system, device, or composition), implicitly provides support for any detectable amount/number or ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the whole/collection being made up of the element, or essentially all of the whole/collection being made up of the element (i.e., that the collection consists essentially of the referenced element). Similarly, a method described as including a step with respect to an effect/outcome implicitly provides support for the referenced step providing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the effect/outcome, representing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the steps/effort performed, or both. Explicit listing of percentages of elements/steps in connection with aspects does not limit or contradict such implicit disclosure.

Uncontradicted, terms such as "comprising" when used in connection with a step of a method provide implicit support for performing the step once, ≥2 times, or until an associated function/effect is achieved.

Uncontradicted, the term "one" means a single type, single iteration/copy/thing, of a recited element or step, or both, which will be clear from context. For example, the referent "one" used with a component of a composition can refer to one type of element (which may be present in numerous copies, as in the case of an ingredient in a composition), one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a component of a composition/system).

Uncontradicted, the term "some" means ≥2 copies/instances or ≥5% of a listed collection/whole is, or is made up of, an element. Regarding methods, some means ≥5% of an effect, effort, or both, is made up of or is attributable to a step (e.g., as in "some of the method is performed by step Y") or indicates a step is performed ≥2 times (e.g., as in "step X is repeated some number of times"). "Predominately," "most," or "mostly," means detectably ≥50% (e.g., mostly comprises, predominately includes, etc., mean ≥50%) (e.g., a system that mostly includes element X is composed of ≥50% of element X). The term "generally" means ≥75% (e.g., generally consists of, generally associated with, generally comprises, etc., means ≥75%) (e.g., a method that generally consists of step X means that ≥75% of the effort or effect of the method is attributable to step X). "Substantially" or "nearly" means ≥95% (e.g., nearly all, substantially consists of, etc., mean ≥95%) (e.g., a collection that nearly entirely is made up of element X means that at least 95% of the elements in the collection are element X).

Uncontradicted, any aspect described with respect to an optionally present element(s)/step(s) also provides implicit support for corresponding aspect(s) in which one, some, most, generally all, nearly all, essentially all, or all of such element(s) are lacking/step(s) not performed, in respect of the relevant aspect. E.g., disclosure of a system comprising element X implicitly also supports a system lacking element X.

Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C, can be performed in the order C, B, and A; B and A and C simultaneously, etc.). Uncontradicted, elements of a composition, device, or system can be assembled in any suitable manner by any suitable method. In general, any methods and materials similar or equivalent to those described here can be used in the practice of embodiments. Uncontradicted, the use of ordinal numbers such as "first," "second," "third," and so on is to distinguish respective elements rather than to denote a particular order of those elements or suggest a particular relationship/characteristic between such elements.

Uncontradicted, any elements, steps, components, or features of aspects and all variations thereof, etc., are within the scope of the invention.

Elements associated with a function can be described as "means for" performing a function in a composition/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated by the use of the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, or the like using teachings provided here or in the art.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

Additional Terms, Concepts, and Acronyms

The following description of certain additional terms and acronyms is provided to assist readers in understanding the invention. Additional acronyms also may be only provided in other parts of this disclosure and acronyms that are well known in the art may not be included here.

Uncontradicted, any description of weight is percent by weight ("wt. %"). Use of the unit abbreviation "wt. %", when used with a value, should be interpreted as "by weight". Ingredient amounts can, in places in this disclosure, be presented as "weight/volume" percentages ("wt/v. %," "w/v," and the like). Use of weight/volume percentage is typically used when specifically presenting exemplary liquid formulations (such as, e.g., in the Examples section of this disclosure).

Herein, uncontradicted, the terms "composition" and "formulation" are used interchangeably, both terms used to refer to preparations comprising active ingredient(s) in a form suitable for ophthalmic administration to a mammal (a subject), such as a human.

Uncontradicted, compositions herein are suitable (as described above) and also can be characterized as "ophthalmologically suitable." "Pharmaceutical suitability", "pharmaceutically suitable", "ophthalmologically suitable" or "ophthalmological suitability" are phrases typically used to refer to compositions that are safe and effective for pharmaceutical administration and application, having sufficient potency, purity, strength, quality, and safety for pharmaceutical application, in cases specifically to the eye, as may be judged by regulatory authority review, and as established by, e.g., one or more well controlled and adequate clinical studies performed in compliance with generally prevailing regulatory authority standards as established by, e.g., the US Food and Drug Administration (FDA). Compositions described as "ophthalmologically suitable" are suitable for ophthalmic delivery, having sufficient potency, purity, strength, or quality making it safe and effective for ophthalmic use. Uncontradicted, components described as "ophthalmologically suitable" should be interpreted in a similar manner. Such terms generally mean that a referenced composition, excipient, API, etc., is suitable for application to the eye, the area around the eye, or both (e.g., as determined by safety testing such as through one or more well-controlled clinical studies in relevant subjects resulting in a significant determination of suitability in terms of safety, toxicity, irritability, lack of other major adverse events associated with such ophthalmological products, and the like). In certain embodiments, an ophthalmologically suitable composition is a composition which does not detectably or significantly irritate or inflame the eye or the area surrounding the eye (e.g., in a significant number of patients as determined through such above-referenced studies), cause significant eye irritation, or cause the receiving subject to experience significant discomfort due to its application (again, typically as determined on a detectable or significant level through one or more well-controlled studies). Compositions, formulations, components/excipients, etc., described/referenced with respect to compositions or methods of the invention are implicitly to be understood as referring to ophthalmologically suitable material(s)/composition(s).

Uncontradicted, a description of "suitability" implicitly means that the referenced element, step, etc., is ophthalmologically/pharmaceutically suitable or otherwise medically suitable (e.g., safe, and effective as determined by proper nonclinical/clinical testing).

Uncontradicted, any disclosed "compound," "API," "active," and the like, should be interpreted to include any appropriate/applicable derivative(s), prodrug(s), hydrate(s), salt(s), solvate(s), enantiomer(s), or polymorph(s) thereof (and to implicitly disclose each such applicable additional compound(s) as a separate aspect of the invention apart from the specifically described compound/API, etc.). For example, uncontradicted, use of "compound" in "brinzolamide compound" means the base compound brinzolamide or any pharmaceutically acceptable enantiomer(s), pharmaceutically acceptable salt(s), pharmaceutically acceptable derivative(s), pharmaceutically acceptable polymorph(s), pharmaceutically acceptable prodrug(s) thereof, or a combination of any or all thereof. Similarly, uncontradicted, a "brimonidine compound" means the base compound brimonidine, or any pharmaceutically acceptable enantiomer(s), pharmaceutically acceptable salt(s), pharmaceutically acceptable derivative(s), pharmaceutically acceptable polymorph(s), or pharmaceutically acceptable prodrug(s) thereof, or a combination of any or all thereof. In any instance where a combination of the terms is used, e.g., description of a "compound" and any applicable derivative thereof is used, the language should be interpreted as inclusive of free or unmodified base compound and any such appropriate derivative described here.

Except where explicitly indicated or clearly indicated by context, "improved" herein means "increased." However, in aspects, "improved" means "reduced," such as with respect to the toxicity of a composition, adverse events, and other negative characteristics, properties, or events. Uncontradicted, terms such as "enhanced," "improved," and the like are used synonymously. Any description of an improvement, increase, reduction, or enhancement or use of similar language, means a detectable or significant (DOS) level/amount of such improvement, increase, reduction, or enhancement (or the like).

Described here are compositions which can be characterized, in aspects, by the elements of which they are comprised. In aspects, compositions provided by the invention are characterized as having one or more "components." Used here, uncontradicted, the term "components" refers to one or discrete compounds/molecules, or ingredients comprising such compound(s), which provide a specific function. For example, a "preservative component" is a component of a composition comprising one or more constituent compound(s)/molecule(s), which each alone or together provide(s) detectable or significant preservation effect(s) when present in effective amount(s). Here, the term "constituents" typically refers to compound(s)/molecule(s) of a component or composition. The term "agent" also can be used synonymously with "constituent, "ingredient," or "compound." The terms "ingredient", "ingredients," or "ingredient(s)" can refer to an individual compound/molecule (which may, or may not, be a constituent of a component) or a component of a composition. Terms such as "product" are sometimes used here in reference to compositions disclosed here. However, based on context, such terms can either refer to either formulation compositions disclosed here or other compositions comprising such formulation compositions, such as drug/device combinations, or components (as in the case of kits for preparing compositions).

Uncontradicted, herein, terms such as "pharmaceutical compound", "pharmaceutically acceptable compound", "ophthalmologically suitable compound", or other similar phrases incorporating the use of the term "compound" refer to a chemical or biological compound or substance, or a mixture or combination of two or more such compounds or substances, intended for use in the medical diagnosis, cure, treatment, or prevention, of one or more diseases, conditions, or pathologies. Uncontradicted, compounds in compositions are ophthalmologically suitable. Uncontradicted, the term "compound" can mean a compound or a molecule, which can be, where suitable, an ion, atom, or a collection of compounds. Uncontradicted, the term compound means a type of compound/molecule, which can be present in any suitable amount, rather than in a single instance/copy/molecule.

The term "effective," when used in reference to an excipient/component of a composition, refers to an excipient/component that is effective to perform an intended/referenced function when used under intended conditions (including being used in an effective amount an effective number of times over an effective period of use in a suitable environment/context/host), as reflected in, e.g., detectable or significant effect(s). An "effective amount" similarly means an amount that is effective to perform an intended/referenced function. Readers will understand that effectiveness is, accordingly, determined based on context. In respect of active pharmaceutical ingredient(s) (API(s)), effectiveness typically is evaluated based on, i.a., the ability to cause an intended effect (treatment or prevention of disease, symptom of disease, etc.) in a subject or a significant number of subjects (e.g., in a clinical study or in clinical studies) (i.e., in "subject(s)"). For example, an effective amount of a suspending agent is an amount that is capable of effectively suspending an effective amount of one or more other ingredient(s) in a composition and an effective amount of a buffer is an amount of a buffer that provides effective buffering with respect to an effective amount of ingredient(s) in a composition. Effective ingredients also are implicitly suitable ingredients. Similarly, an effective excipient is also an excipient that is suitable for ophthalmological use in terms of safety and maintaining effectiveness of associated API(s). Uncontradicted, ingredients are present in compositions in effective amounts. Uncontradicted, compound(s)/API(s) are present in compositions in therapeutically effective amount(s) and compositions (e.g., compositions in containers, compositions in methods, etc.) are also present in therapeutically effective amount(s). A "therapeutically effective amount" typically means an amount of a compound or composition that is effective to treat an aspect of an intended disease or condition in a significant number of subject(s), typically a sufficiently significant number of subject(s) to obtain regulatory authority approval for use of the product as a therapeutic agent/drug (e.g., by US FDA), when used as indicated (i.e., per an indicated dosing regimen over a suitable treatment period). In aspects, a therapeutically effective amount is demonstrated by at least one or at least two well controlled and adequate clinical studies in human subjects/patients (e.g., as would be considered sufficient for pharmaceutical approval).

A suitable excipient/component (e.g., a pharmaceutically acceptable excipient) typically means a pharmaceutically inactive component that is compatible with other ingredients of the formulation (does not cause such other components to be inactivated or unstable, react to form undesirable reactants, etc.), which is not detectably or significantly deleterious to the recipient of the composition, which is formulated in combination with the APIs of the composition, and which typically detectably or significantly imparts one or more characteristics to a composition/API, improves one or more characteristics of the composition/API (e.g., delivery, stability, form, distribution of APIs, chemical characteristics of the composition, etc.), or both. This concept of suitable "compatibility" is applicable to any combination of ingredients in a composition of the invention.

Many characteristics of compositions are provided here which are described relative to storage conditions. In aspects, products disclosed herein are adapted to be administered or are administered topically (e.g., as ophthalmic drops). Stability can be assessed under any suitable temperature and humidity conditions, such as those applied for the relevant type of product by FDA. In aspects, particular temperature and humidity conditions are provided. E.g., for topically applied ophthalmic products (e.g., drops) such conditions can be about 25° C. and about 40% relative humidity or about 40° C. and no more than about 25% relative humidity.

SUMMARY OF THE INVENTION

The inventions described and claimed herein have many attributes and aspects including, but not limited to, those set forth in, e.g., described or referenced in, this Summary. This Summary of the Invention ("Summary") is not intended to be all-inclusive, and the scope of the invention is not limited to or by the aspects, features, elements, or embodiments provided in this Summary, which is included for illustrative purposes only and not restriction. Any of the aspects described under this section can be combined with any other aspect described in this section or with any other aspect of this disclosure.

The invention described herein provides, among other things, pharmacologically acceptable and ophthalmologically suitable compositions for use in treating ophthalmic diseases or related conditions. In aspects, the invention provides pharmaceutically acceptable and ophthalmologically suitable compositions including effective amounts of carbonic anhydrase inhibitor(s) and alpha-2-adrenergic agonist(s). In facets, such compositions further comprise a penetration enhancer component, which comprises one or more penetration enhancer compound(s)/molecule(s). In aspects, the invention provides fixed dose compositions comprising effective amounts of brimonidine compound(s) and brinzolamide compound(s) that are capable of being administered once or twice per day for the treatment of elevated intraocular pressure, but which provide similar efficacy to a similar or substantially identical product, such as the only currently FDA approved and on-market brinzolamide/brimonidine tartrate ophthalmic suspension. In facets, the invention provides compositions which are capable of being administered at a frequency that results in providing a lower total dose of both brinzolamide and brimonidine compound(s) to a recipient, but nonetheless are as or more effective in IOP control as such similar or substantially identical products.

In specific embodiments, the invention provides pharmaceutically acceptable and ophthalmologically suitable compositions comprising brinzolamide compound in an amount of between about 0.1 wt. %-about 10 wt. % of the composition and a brimonidine compound in an amount of between about 0.01 wt. %-about 0.5 wt. % of the composition. In aspects, the brimonidine compound is brimonidine tartrate. In aspects, compositions further comprise an effective amount of a borate-polyol complex. In aspects, the total of one or more borate-polyol complexes present in composition make(s) up about 0.5 wt. %-about 6 wt. % of the composition. In aspects, compositions further comprise an effective penetration enhancer component.

In certain facets, the invention provides pharmaceutically acceptable and ophthalmologically suitable compositions comprising: (a) a brinzolamide compound in an amount of between about 0.1 wt. %-about 10 wt. % of the composition; (b) a brimonidine compound in an amount of between about 0.01 wt. %-about 0.5 wt. % of the composition; (c) one or more borate-polyol complexes, wherein the total of the one or more borate-polyol complexes are present in an amount of between about 0.5 wt. %-about 6 wt. % of the composition; and (d) benzalkonium chloride in an amount between 0.005-about 0.02 wt. % of the composition. In aspects, the brimonidine compound is brimonidine tartrate.

The invention provides a composition comprising any of the active ingredient(s) and optionally other ingredient(s)/component(s) described above in this section, wherein the composition, when administered to a subject, once or twice per 24-hour period, demonstrates bioequivalence to; or demonstrate detectably or significantly improved pharmacokinetic properties or clinical results over; a similar or substantially identical reference product administered three times per day. In aspects, the reference product is an FDA approved reference product including brinzolamide and brimonidine for ophthalmologic application(s). In aspects, the FDA reference product is the currently FDA approved and marketed version of Simbrinza® (ALCON) (the details of which are described below). In aspects, bioequivalence is determined by the performance of an FDA-approved clinical endpoint study. In aspects, bioequivalence is determined by the performance of a clinical endpoint study performed substantially in accordance with FDA guidance/recommendations, except with respect to frequency of administration of the composition and the reference product. In aspects, the invention provides improved brinzolamide and brimonidine ophthalmic composition demonstrating greater bioavailability, tolerability, retention time, patient compliance, and reduced dosing frequency over that of reference product(s).

In embodiments, the invention provides methods of treating ocular hypertension or elevated intraocular pressure (IOP), comprising administration of a pharmaceutically acceptable and ophthalmologically suitable composition comprising a brinzolamide compound in an amount of between about 0.1 wt. %-about 10 wt. % of the composition and a brimonidine compound in an amount of between about 0.01 wt. %-about 0.5 wt. % of the composition. In aspects, the brimonidine compound is brimonidine tartrate. In aspects, compositions further comprise at least one borate-polyol complex, wherein the total amount of borate-polyol complex(es) represents between about 0.5 wt. %-about 6 wt. % of the composition. In aspects, compositions further comprise a penetration enhancer component. In aspects, the method comprises administration of such compositions once or twice per day. In aspects, such a method demonstrates bioequivalence to, or demonstrates detectably or significantly improved pharmacokinetic properties over, a similar method comprising use of a reference product administered three times per day, such as an FDA approved reference product, e.g., Simbrinza®, In aspects, the elevated IOP treated by the method is associated with patient(s) diagnosed with or suffering from glaucoma. In aspects such glaucoma is open-angle glaucoma.

In other embodiments, the invention provides methods of treating irritation of the cornea, irritation of ocular tissue adjacent the cornea, or dry eye, comprising administration of a pharmaceutically acceptable and ophthalmologically suitable composition comprising a brinzolamide compound in an amount of between about 0.1 wt. %-about 10 wt. % of the composition and a brimonidine compound in an amount of between about 0.01 wt. %-about 0.5 wt. % of the composition. In aspects, the brimonidine compound is brimonidine tartrate. In aspects, compositions further comprise at least one borate-polyol complex, wherein the total of amount of borate-polyol complex(es) represents between about 0.5 wt. %-about 6 wt. % of the composition. In aspects, compositions further comprise a penetration enhancer component. In aspects, the method comprises administration of such compositions once or twice per day. In aspects, such a method demonstrates bioequivalence to, or demonstrates detectably or significantly improved pharmacokinetic properties over, a similar method comprising use of a reference product administered three times per day, such as an FDA approved reference product, e.g., Simbrinza®. In aspects, compositions comprise an effective amount of benzalkonium chloride which detectably or significantly increases the penetration of one or more of the active pharmaceutical ingredients of the composition.

According to aspects, the invention provides methods of treating a condition such, e.g., elevated IOP, such as IOP associated with glaucoma, e.g., open-angle glaucoma, irritation of the cornea, irritation of ocular tissue adjacent the cornea, dry eye, or any combination thereof with compositions of the invention wherein the method results in a detectable or significant reduction in one or more adverse events compared to a reference product, e.g., an FDA approved reference product, e.g., Simbrinza®, or a composition comprising the same amount of brimonidine compound, the same amount of brinzolamide compound, and 0.003 wt. % benzalkonium chloride. In aspects, compositions comprise an effective amount of benzalkonium chloride which detectably or significantly increases the penetration of one or more of the active pharmaceutical ingredients of the composition.

In certain embodiments, the invention further provides methods (e.g., a process) of making compositions such as those described here, as well as kits for storing and distributing compositions, components of compositions, and optionally other material(s) (e.g., devices for delivery of compositions) an end-user/health care provider.

DETAILED DESCRIPTION OF THE INVENTION

For convenience, both combinations of elements/steps and individual elements/steps may be described in this section of this disclosure. Despite the inclusion of passages focused on specific elements/steps, any aspect, facet, embodiment, or other description of particular step(s) or element(s) can be applied to any general description of the compositions/methods of the invention, or any other recited element(s)/step(s) thereof, which are provided in any part of this disclosure.

Compositions

In aspects, the invention provides compositions comprising one or more carbonic anhydrase inhibitors (CAIs), one or more alpha-2-adrenergic agonists, a preservation component, a penetration enhancement component, and a carrier. In aspects, compositions are designed for ophthalmic delivery. In aspects, compositions are formulated as a suspension in the form of drops suitable for administration to a mammalian eye. In aspects, compositions can comprise one or more additional actives or excipients. In aspects, compositions comprise one or more advantageous or surprising properties. For example, some compositions of the invention are as effective or more effective when administered once or twice a day to a subject as a reference composition administered three times a day that is substantially similar or identical to the composition in most respects, or generally all respects (e.g., in terms of ingredients, API amount, and other characteristics).

Carbonic Anhydrase Inhibitor (CAI)

In aspects, compositions provided by the invention comprise one or more compounds characterizable as a carbonic anhydrase inhibitor (CAI). In aspects, the one or more CAIs can comprise any pharmaceutically acceptable and ophthalmologically suitable CAI suitable for topical administration to a mammalian eye. In aspects, the one or more CAI(s) can comprise any pharmaceutically acceptable and ophthalmologically suitable CAI suitable for topical administration which is capable of detectably or significantly reducing elevated intraocular pressure (IOP) in a recipient eye, such as, e.g., the eye of a patient diagnosed with or suffering from open-angle glaucoma or ocular hypertension. In aspects, the CAI is further characterizable as a non-bacteriostatic sulfonamide derivative.

In aspects, the one or more CAIs can be selected from a group comprising, e.g., brinzolamide compounds, e.g., brinzolamide acetazolamide, methazolamide, dorzolamide, diclofenamide, ethoxzolamide, zonisamide, etc. In specific aspects, the one or more CAIs is a brinzolamide compound.

Brinzolamide Compounds

According to aspects, compositions provided by the invention comprise one or more brinzolamide compounds. Brinzolamide is a carbonic anhydrase inhibitor (CAI), chemically known as (R)-(+)-4-Ethylamino-2-(3-methoxypropyl)-3,4-dihydro-2H-thieno [3,2-e]-1,2-thiazine-6-sulfonamide-1,1-dioxide. The empirical formula of brinzolamide is $C_{12}H_{21}N_3O_5S_3$, and the compound has the following chemical structure:

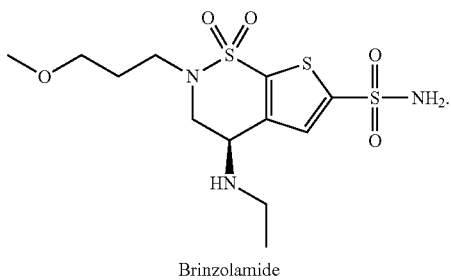 [SMILES: CCN[C@H]1CN(CCCOC)S(=O)(=O)c2sc(S(N)(=O)=O)cc21]

Brinzolamide

In aspects, compositions can comprise any pharmaceutically acceptable and ophthalmologically suitable brinzolamide compound(s), including the base compound brinzolamide or any pharmaceutically acceptable enantiomer(s), pharmaceutically acceptable salt(s), pharmaceutically acceptable derivative(s), pharmaceutically acceptable polymorph(s), pharmaceutically acceptable prodrug(s) thereof, or a combination of any or all thereof.

In aspects, compositions at least generally comprise, at least substantially comprise, or at least essentially only comprise the R-isomer of brinzolamide. In aspects, compositions comprise a detectable or significant amount of the S-isomer of brinzolamide. In aspects, compositions lack any significant amount of, are essentially free of, or are free of, the S-isomer of brinzolamide.

In aspects, compositions comprise one or more salts of brinzolamide, such as, e.g., brinzolamide maleate, or brinzolamide with tartaric acid (e.g., chiral tartaric acid such as di-p-tolyl-D-tartaric acid (DTPA)).

In aspects, compositions comprise one or more derivatives of brinzolamide, such as, e.g., N-desethyl brinzolamide, brinzolamide-related compound B, or, for example, compounds disclosed in U.S. Pat. No. 10,485,876 (GRAYBUG VISION INC).

In aspects, compositions comprise one or more prodrugs of brinzolamide, such as, e.g., one or more prodrugs of brinzolamide disclosed by IKUTA, et. al., in "Creation of nano eye-drops and effective drug delivery to the interior of the eye," in Scientific Reports (NATURE), published online on Mar. 14, 2017.

In certain aspects, compositions at least generally comprise, at least substantially comprise, or at least essentially consist of (or consist of), brinzolamide base. As noted elsewhere, herein the term "brinzolamide" or "brinzolamide compound" should be interpreted to mean brinzolamide base or any pharmaceutically acceptable and ophthalmologically suitable brinzolamide compound disclosed in this section (or an equivalent).

In aspects, compositions provided by the invention can comprise any pharmaceutically acceptable and ophthalmologically suitable amount of a brinzolamide compound. In aspects, compositions can comprise between about 0.1 wt. % to about 10 wt. % of a brinzolamide compound, such as, e.g., between about 0.1-about 9 wt. %, ~0.1-~8 wt. %, ~0.1-~7 wt. %, ~0.1-~6 wt. %, or ~0.1-~5 wt. %, such as for example ~0.2-~10 wt. %, ~0.4-~10 wt. %, ~0.6-~10 wt. %, ~0.8-~10 wt. %, ~1-~10 wt. %, or, e.g., ~0.2-~8 wt. %, ~0.4-~6 wt. %, ~0.6-~4 wt. %, ~0.8-~2 wt. %, or, e.g., about 1 wt. % of brinzolamide compound(s).

Alpha-2-Adrenergic Agonist

In aspects, compositions provided by the invention comprise one or more compounds characterizable as an alpha agonist. In aspects, compositions comprise one or more alpha-2-adrenergic agonists (also referred to as alpha-2-agonists). In aspects, one or more alpha-2-adrenergic agonists/alpha-2-agonists can comprise any pharmaceutically acceptable and ophthalmologically suitable alpha-2-adrenergic agonists/alpha-2-agonist suitable for topical administration to a mammalian eye. In aspects, the one or more alpha-2-adrenergic agonist(s)/alpha-2-agonists can comprise any pharmaceutically acceptable and ophthalmologically suitable alpha-2-adrenergic agonist/alpha-2-agonist suitable for topical administration which is capable of detectably or significantly reducing elevated IOP in a recipient eye, such as, e.g., the eye of a patient diagnosed with or suffering from open-angle glaucoma or ocular hypertension. In aspects, the alpha-2-adrenergic agonist/alpha-2-agonist is further characterizable as a 2-imidazoline derivative, a quinoxaline derivative, or both.

In aspects, the alpha-2-adrenergic agonists/alpha-2-agonists of compositions provided by the invention can be selected from a group comprising brimonidine compounds, clonidine, apraclonidine, dexmedetomidine, fadolmidine, etc. In specific aspects, the one or more alpha-2-adrenergic agonists/alpha-2-agonists is a brimonidine compound.

Brimonidine Compounds

According to aspects, compositions provided by the invention comprise one or more brimonidine compounds. In aspects, compositions can comprise any pharmaceutically acceptable and ophthalmologically suitable brimonidine compound(s), including the base compound brimonidine, or a pharmaceutically acceptable enantiomer(s), pharmaceutically acceptable salt(s), pharmaceutically acceptable derivative(s), pharmaceutically acceptable polymorph(s), or pharmaceutically acceptable prodrug(s) thereof, or a combination of any or all thereof.

In aspects, compositions at least generally comprise, at least substantially comprise, or at least essentially comprise/consist of one or more salts of brimonidine, such as, e.g., brimonidine tartrate, or those disclosed in, e.g., U.S. Pat. No. 10,220,043 (KOWA).

In aspects, compositions comprise one or more derivatives of brimonidine, such as, e.g., one or more derivatives of brimonidine disclosed in U.S. Pat. No. 6,294,563.

In aspects, compositions comprise one or more prodrugs of brimonidine, such as, e.g., one or more sulfonyl prodrugs of brimonidine, such as those described in, e.g., CA2603069.

In aspects, compositions at least generally comprise, at least substantially comprise, or at least essentially comprise, a salt of brimonidine. As used herein the term "brimonidine" or "brimonidine compound" should be interpreted to mean a brimonidine salt or any pharmaceutically acceptable and ophthalmologically suitable brimonidine compound disclosed in this section (or an equivalent thereof). In aspects, compositions at least generally comprise, at least substantially comprise, or at least essentially comprise (i.e., consist essentially of or consist of) brimonidine tartrate.

Brimonidine Tartrate

According to aspects, compositions provided by the invention comprise brimonidine tartrate. Brimonidine tartrate is a relatively selective alpha-2-adrenergic agonist. Brimonidine tartrate is chemically known as 5-bromo-6-(2-imidazolidinylideneamino) quinoxaline L-tartrate. The empirical formula of brimonidine tartrate is $C_{11}H_{10}BrN_5$—$C_4H_6O_6$, and the compound has the following chemical structure:

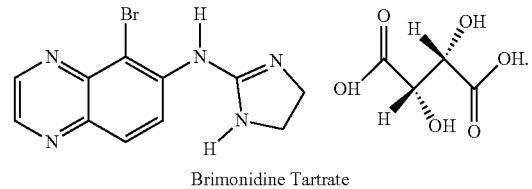

Brimonidine Tartrate

In aspects, compositions provided by the invention can comprise any pharmaceutically acceptable and ophthalmologically suitable amount of a brimonidine compound, e.g., a brimonidine salt, such as, e.g., brimonidine tartrate. In aspects, compositions can comprise between about 0.01 wt. % to about 0.5 wt. % of a brimonidine compound, such as, e.g., between about 0.01-about 0.45 wt. %, ~0.01 to (-) ~0.4 wt. %, ~0.01-~0.35 wt. %, ~0.01-~0.3 wt. %, ~0.01-~0.25 wt. %, or ~0.01-~0.2 wt. %, such as between ~0.02-~0.5 wt. %, ~0.04-~0.5 wt. %, ~0.06-~0.5 wt. %, ~0.08-~0.5 wt. %, ~0.1-~0.5 wt. %, ~0.12-~0.5 wt. %, ~0.14-~0.5 wt. %, ~0.16-~0.5 wt. %, ~0.18-~0.5 wt. %, or ~0.2-~0.5 wt. %, e.g., ~0.02-~0.45 wt. %, ~0.04-~0.4 wt. %, ~0.06-~0.35 wt. %, ~0.08-~0.3 wt. %, ~0.1-~0.25 wt. %, ~0.15-~0.25 wt. %, or, e.g., ~0.2 wt. % of a brimonidine compound, such as a brimonidine salt, e.g., brimonidine tartrate. In aspects, compositions comprise, e.g., about 0.5-3 mg, e.g., about 0.75-2 mg, such as about 1-1.75 mg, e.g., about 1.2-1.5 mg or about 1.25-1.45 mg of brimonidine. In aspects, a brimonidine compound is a salt of brimonidine, which, in aspects, is present in an amount that is approximately equivalent or equivalent to such an amount of free/free base brimonidine. For example, in aspects, compositions comprise about 2 mg of brimonidine tartrate, equivalent to about 1.32 mg of free base brimonidine compound. As another example of the application of this principle, compositions can, e.g., comprise about 0.75-0.76 (e.g., about 0.758) mg to about 4.5 mg (e.g., 4.545 mg) brimonidine tartrate. Readers can readily similarly calculate other amounts of a brimonidine salt compound provided by such disclosure depending on the salt form used in the applicable composition.

Brinzolamide & Brimonidine Combinations

In aspects, compositions provided by the invention comprise a pharmaceutically acceptable and ophthalmologically suitable CAI and a pharmaceutically acceptable and ophthalmologically suitable alpha-2-adrenergic agonist in combination with one another (within a single composition). Such combination compositions can be referred to as "fixed dosage" combination products. The term "fixed dose" (AKA, "fixed-dose") is understood in the art as referring to a combination of two or more active ingredients (API(s)) within a single form of pharmaceutical administration, and does not necessarily impart any limitation on the relationship of dose(s) of such active ingredients, etc. See, e.g., Goodman et al. Expert Review of Pharmacoeconomics & Outcomes Research, 20:1, 1-26.

In aspects, compositions provided by the invention comprise a pharmaceutically acceptable and ophthalmologically suitable fixed-dose combination of a brinzolamide compound and a brimonidine compound. In aspects, the brimonidine compound is brimonidine tartrate. In aspects, compositions comprise about 0.1 wt. % to about 10 wt. % of a brinzolamide compound, such as, e.g., ~0.2-~8 wt. %, ~0.4-~6 wt. %, ~0.6-~4 wt. %, ~0.8-~2 wt. %, or, e.g., about 1 wt. % of a brinzolamide compound in combination with about 0.01 wt. % to about 0.5 wt. % of a brimonidine compound, such as, e.g., ~0.02-~0.45 wt. %, ~0.04-~0.4 wt. %, ~0.06-~0.35 wt. %, ~0.08-~0.3 wt. %, ~0.1-~0.25 wt. %, ~0.15-~0.25 wt. %, or, e.g., ~0.2 wt. % of a brimonidine compound, such as a brimonidine salt, e.g., brimonidine tartrate. In aspects, compositions comprise about 1 wt. % of a brinzolamide compound, e.g., free base brinzolamide, and about 0.2 wt. % of a brimonidine compound, such as a brimonidine salt, e.g., brimonidine tartrate.

Preservative

In aspects, compositions provided by the invention comprise a preservative component comprising one or more ophthalmologically suitable preservation agent(s)/constituent(s) ("preservatives"). In alternative aspects, compositions provided by the invention do not comprise a preservative, such that the composition(s) provided by the invention are characterizable as "preservative free." In aspects, compositions lack any significant amount of any agent that is solely/mostly characterizable as a preservative or that is at all characterized as a preservative. In aspects, compositions are generally free, substantially free, or essentially free of any preservative(s).

Uncontradicted, any aspect described herein as being "free" of a component/element simultaneously implicitly provides a corresponding disclosure of a component/composition including a "low" amount of the referenced ingredient/component in question (a low amount meaning (1) less than 5%, less than 2%, less than 1%, less than 0.5%, less than 0.2%, less than 0.1%, less than 0.05%, less than 0.02%, or less than 0.01% of the composition on a weight basis, volume basis, or compound number/molar basis or (2) an amount that is less than 50%, such as less than 20%, less than 10%, less than 5%, or less than 1% of the typical amount of the element/composition in corresponding compositions, methods, etc., in the art or in leading products in the art, such as in Simbrinza®.

In aspects, compositions provided by the invention comprise a preservative component comprising one or more preservatives which, either alone or in combination, provide detectable or significant preservative effect. In aspects, the preservative component detectably or significantly inhibits microbial growth sufficient to provide stability and suitability for use for a period of ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or more (e.g., about 3-36 months, about 6-36 months, about 4-36 months, about 18-36 months, about 12-24 months, about 6-24 months, or about 12-36 months) or more, when stored at about 25° C. and about 40% relative humidity or at about 40° C. and about 25% relative humidity.

In aspects, one or more compounds of a composition providing a detectable or significant preservative effect can also provide one or more additional detectable or significant effects, such as chelation effect, buffering effect, penetration enhancement effect, etc.

In aspects, a "preservative" is a compound which detectably or significantly enhance stability of the composition(s), such as the stability of the one or more brinzolamide compounds, one or more brimonidine compounds, or both, reduces the number(s)/amount(s) of detectable/significant impurities over the course of a storage under room temperature or accelerated storage conditions, detectably or significantly reduce antimicrobial activity (e.g., within the composition), or any combination of any or all thereof. In aspects, compositions comprise a preservative component which provides for compositions which retain at least 90% of the one or more brinzolamide compounds and at least 90% of the one or more brimonidine compounds when stored at about 25° C.+/−2° C. and about 40% relative humidity, at about 40° C. and not more than 25% relative humidity, or both.

In aspects, the invention provides composition(s) comprising ophthalmologically suitable preservative(s) that are effective (e.g., agents capable of demonstrating one or more of the characteristics of a preservative described above in the context of a composition of the invention) at a pH range of between, e.g., ~4.0-~9.5, such as between ~5.0-~9.0, e.g., or, e.g., ~5.5-~8.5. In aspects, a preservative does not detectably or significantly negatively impact any other component of the formulation, such as, e.g., they do not detectably or significantly reduce the efficacy or functionality of any one or more brinzolamide compounds, brimonidine compound (e.g., reduce efficacy in treating IOP), or any other API or excipient present in the composition.

In aspects, compositions provided by the invention comprise any pharmaceutically acceptable and ophthalmologically suitable preservative. In aspects, compositions provided by the invention comprise any pharmaceutically acceptable and ophthalmologically suitable preservative capable of detectably or significantly inhibiting microbial growth. Exemplary preservatives include, e.g., quaternary ammonium salts such as benzalkonium chloride (sometimes abbreviated herein as BKC, and which is often abbreviated in the art as BAC, BAK, or BZK) and benzethonium chloride; hydrogen peroxide; sorbic acid; biquanides; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; thiomersal (e.g., stabilized thimerosal), and others such as, e.g., benzoic acid, benzyl paraben, bronopol, butyl paraben, cetrimide, cetylpryidinium chloride, chlorocresol, chloroxylenol, cresol, ethyl alcohol, ethyl paraben, ethylparaben, glycerin, hexetidine, imidurea, isobutyl paraben, metacresol, phenol, phenoxyethanol, phenylethyl alcohol, phenylmucuric nitrate, p-hydroxybenzoic acid esters, polyhexamethylene biguanide, potassium sorbate, propyl paraben, propylene glycol, sodium benzoate, sodium perborate, sodium propionate, sodium citrate, and the like, or any ophthalmologically acceptable salts thereof, or combinations of any ≥2 of such compounds, or equivalents thereof.

Borate/Boric Acid

In aspects, one constituent of a preservative component is one or more borate compounds. The term "borate" as used herein, refer to boric acid, salts of boric acid and other pharmaceutically acceptable borates, or combinations thereof. In aspects, borate includes boric acid, sodium borate, potassium borate, calcium borate, magnesium borate, manganese borate and other such borate salts. In aspects, compositions provided by the invention comprise boric acid.

In aspects, borate, when present in compositions provided by the invention in combination with one or more polyol compounds (e.g., mannitol, sorbitol, glycerol and propylene glycol, and the like), forms a detectable or significant quantity of a borate-polyol complex. In aspects, a borate-polyol complex is capable of providing a detectable or significant preservative effect(s), such as preservative effect(s) described in this section (or an equivalent).

Polyols

In aspects, one constituent of a preservative component is one or more polyol compounds. The term "polyol" as used herein, refers to any compound having at least two adjacent —OH groups. In aspects, the OH groups in polyols are not in trans configuration relative to each other. In aspects, a polyol compound can be linear, circular, substituted, unsubstituted, or mixtures thereof. In aspects, compositions comprise at least one polyol capable of forming a complex with one or more borate compounds. In aspects, a significant amount of any such complex-forming compound(s) in a composition will form a complex and maintain the complex under typical storage conditions. In aspects, most of at least one type of such complex-forming compounds, generally all of such complex-forming compounds, or at least substantially all of at least one type of such compounds will form such a complex.

In aspects, polyol(s), when present in compositions provided by the invention in combination with one or more borate compounds (e.g., boric acid), form a detectable or significant quantity of a borate-polyol complex (or a plurality of complexes when two or more different borate compounds or two or more different polyol compounds are present). In aspects, as described above, a borate-polyol complex is capable of providing a detectable or significant preservative effect(s), such as any of the preservative effect(s) described herein.

In aspects, exemplary polyols include, e.g., sugars, sugar alcohols, sugar acids, uronic acids, etc. In aspects, compositions provided by the invention comprise polyols characterizable as sugars, sugar alcohols and sugar acids. In aspects, compositions comprise polyols such as, e.g., mannitol, glycerin, propylene glycol and sorbitol. In aspects, compositions comprise two or more polyol compounds, such as, e.g., 2, 3, or 4 or more polyol compounds. In aspects, compositions comprise 2 or more polyols in combination with boric acid. In aspects, compositions comprise mannitol, propylene glycol, or both mannitol and propylene glycol. In aspects, compositions comprise mannitol, propylene glycol, or both mannitol and propylene glycol, in addition to boric acid. In aspects, when present with a borate compound, mannitol, propylene glycol, or both mannitol and propylene glycol form a detectable or significant amount of borate-polyol complex(es).

Borate-Polyol Complexes

According to aspects, compositions comprise one or more borate-polyol complexes. In aspects, compositions comprise a single borate-polyol complex. In aspects, compositions comprise a plurality of borate-polyol complexes. In some aspects, compositions do not comprise a detectable or significant amount of borate-polyol complex(es). In aspects, compositions comprise an amount of benzalkonium chloride which is greater than about 0.005 wt. % of the composition. In aspects, compositions comprise an amount of benzalkonium chloride which is less than about 0.005 wt. %, such as, e.g., less than about 0.0045 wt. %, or less than about 0.004 wt. %, as in, e.g., about 0.0035 wt. % or 0.003 wt. % benzalkonium chloride. In aspects, compositions comprising benzalkonium chloride in an amount which is greater than or equal to 0.005 wt. % do not comprise a detectable or significant amount of borate-polyol complex(es) or components which form borate-polyol complex(es). In aspects, compositions comprising benzalkonium chloride in an amount which is less than about 0.005 wt. % comprise a detectable or significant amount of borate-polyol complex(es). In aspects, compositions comprise an amount of borate-polyol complexes which provides a detectable or significant preservation effect.

Borate compound(s) and polyol(s) can form, e.g., two types of borate-polyol complexes depending on whether two or four water molecules are released. When one borate ion complexes with one polyol molecule, a 1:1 species can be formed; when one borate ion complexes with 2 polyol molecules, a 1:2 species can be formed. In aspects, compositions comprise a borate-polyol complex derived from boric acid interacting with mannitol. In aspects, compositions comprise a borate-polyol complex derived from boric acid interacting with propylene glycol. In aspects, 1:1 borate-polyol species are detectably or significantly present in compositions provided by the invention. In aspects, 1:2 borate-polyol species are detectably or significantly present in compositions provided by the invention. In aspects, both 1:1 and 1:2 borate-polyol species are detectably or significantly present in compositions provided by the invention. In aspects, any pharmaceutically acceptable and ophthalmologically suitable borate-polyol complexes (such as those disclosed in, e.g., EP93911061B1 and US20030130207A1) can be present in compositions provided here.

In aspects, borate/polyol complex(es) present in compositions provide(s) detectable or significant preservation effect(s), e.g., preservation effect as described elsewhere herein.

In aspects, a preservative component of compositions provided by the invention comprises one or more of a pharmaceutically acceptable and ophthalmologically suitable borate-polyol complex. In aspects, such a complex results from the presence of both one or more borate compounds (e.g., boric acid) and one or more polyol compounds (e.g., mannitol, glycerin, propylene glycol, and sorbitol), such as two or more polyols, e.g., both mannitol and propylene glycol, in the composition.

In aspects, the borate-polyol complex is water-soluble. In aspects, borate-polyol complex(es) of the present invention are formed by the mixing of one or more borate compounds with one or more polyol(s) compounds in an aqueous solution. In aspects, such complexes are formed during the manufacturing process.

Uncontradicted, the term "borate-polyol complex" or "borate-polyol complexes" should be interpreted as encompassing any and all such complex(es) present in the composition, whether only one such complex is present or whether two or more such complexes are present.

In aspects, compositions can comprise borate-polyol complexes in combination with one or more other compounds providing detectable or significant preservative or disinfectant effect to meet preservation efficacy and disinfection standards/requirements known in the art, such as to ensure a composition is suitable for FDA approval.

Benzalkonium Chloride

In aspects, compositions can comprise one or more compounds capable of providing two or more effects when present in sufficient quantities. Such compounds can be characterized simultaneously as being two types of ingredients. For example, a compound might be characterized as a preservative and a penetration enhancer in a formulation.

In aspects, compositions can comprise one or more compounds capable of providing two or more effects when present in sufficient quantities; however, they are not present in such sufficient quantities in an applicable composition, such that one or more such effects is not detectable or significant in the applicable composition. E.g., a compound might be present in any amount that is sufficient to impart one effect, but that is too low to impart another effect that the compound is also known for in other contexts.

In aspects, compositions comprise one or more pharmaceutically acceptable and ophthalmologically suitable quaternary ammonium compounds in a sufficient amount to provide detectable or significant preservative effect(s), such as one or more preservative effects described in this section. In aspects, compositions comprise one or more quaternary ammonium salts. In aspects, compositions comprise benzalkonium chloride in an amount capable of providing detectable or significant preservative effect(s). In aspects, any BKC in compositions is not present in sufficient amount to be considered a solubilizer in such a composition or, e.g., does not detectably or significantly contribute to the solubilizer of an active ingredient of the composition, although BKC can, in other contexts, as a solubilizer. In some such aspects, any solubilizer in the composition will impart significantly greater solubilization effects than any BKC in the composition; any BKC in the composition will not impact a significant solubilization effect; or both statements will be true with respect to the composition.

In aspects, compositions comprise one or more pharmaceutically acceptable and ophthalmologically suitable quaternary ammonium compounds, such as one or more quaternary ammonium salts, which provide 1, 2, 3 or more functions. For example, compositions can comprise benzalkonium chloride in an amount sufficient to provide both preservation effect(s) and penetration effect(s) (such penetration effect(s) described elsewhere herein). In aspects, compositions comprise one or more pharmaceutically acceptable and ophthalmologically suitable quaternary ammonium compounds, such as one or more quaternary ammonium salts (e.g., benzalkonium chloride), in an amount capable of providing only a single function, such as, e.g., penetration effect(s) without preservation effect(s). In aspects, BKC is present in an amount that is sufficient to provide both preservation effect(s) and penetration enhancer effect(s) but does not provide significant solubilizer effect(s).

Sodium Chlorite

In aspects, a penetration enhancer component of a composition comprises sodium chlorite (Purite), wherein the sodium chlorite is present in composition in an amount representing at least about 0.005 wt. % of the composition, such as, e.g., ≥0.0055 wt. %, ≥0.006 wt. %, ≥0.0065 wt. %, or ≥0.007 wt. % of the composition. In aspects, sodium chlorite is present in the composition in an amount which is less than about 0.3 wt. %, such as ≤~0.28 wt. %, ≤~0.26 wt. %, ≤~0.24 wt. %, ≤~0.22 wt. %, or ≤~0.2 wt. % of the composition. In aspects, sodium chlorite is present in the composition in an amount of between about 0.005 wt. % to about 0.2 wt. % of the composition, such as, e.g., between ~0.005-~0.15 wt. %, ~0.005-~0.15 wt. %, ~0.005-~0.1 wt. %, ~0.005-~0.05 wt. %, ~0.005-~0.01 wt. %, ~0.005-~0.009 wt. %, or ~0.005-~0.008 wt. %, e.g., ~0.0055-~0.2 wt. %, ~0.006-~0.2 wt. %, ~0.0065-~0.2 wt. %, ~0.007-~0.2 wt. %, such as, for example, between ~0.0055-~0.15 wt. %, ~0.006-~0.1 wt. %, ~0.0065-~0.05 wt. %, ~0.0065-~0.01 wt. %, ~0.0065-~0.009 wt. %, ~0.0065-~0.008 wt. %, ~0.0065-~0.0075 wt. %, or, e.g., about 0.007 wt. % of the composition. In aspects, sodium chlorite can provide detectable or significant preservation effect in addition to, or alternative to, any penetration enhancement effect.

Preservative Amount

In aspects, compositions provided by the invention comprises one or more preservatives in anti-microbially effective amount(s) which can detectably or significantly inhibit microbial growth. In aspects, an "antimicrobial effective amount" of a preservative is determined by performing preservative efficacy tests or antimicrobial effectiveness tests known in the art. In aspects, such tests are described in, e.g., chapter 51 of the United States Pharmacopoeia 29-National Formulary 24 (USP 29-NF 24). In aspects, composition(s) provided by the invention comprise one or more preservatives in an amount within the concentration ranges described in one or more standard reference books such as the most recent edition of Remington's Pharmaceutical Sciences, Handbook of Pharmaceutical Excipients (e.g., $5^{th}$ ed. or $6^{th}$ ed.), or Handbook of Pharmaceutical Excipients (e.g., $9^{th}$ ed., Sheskey et al. (ISBN 9780 85711 375 7) (2020)).

In aspects, compositions comprise a preservative component wherein the preservative component is present in the composition in an amount of between about 0.5 wt. % to about 6.2/6.25 wt. %, such as, e.g., between ~0.6-~6.2 wt. %, ~0.8-~6.2 wt. %, ~1-~6.2 wt. %, ~1.2-~6.2 wt. %, ~1.4-~6.2 wt. %, ~1.6-~6.2 wt. %, ~1.8-~6.2 wt. %, ~2-~6.2 wt. %, e.g., ~0.5-~6 wt. %, ~0.5-~5.5 wt. %, ~0.5-~5 wt. %, ~0.5-~4.5 wt. %, ~0.5-~4 wt. %, ~0.5-~3.5 wt. %, ~0.5-~3 wt. %, ~0.5-~2.5 wt. %, ~0.5-~2 wt. %, such as, for example, between ~0.6-~6 wt. %, ~0.7-~5 wt. %, ~0.8-~4 wt. %, ~0.9-~3 wt. %, ~1-~2 wt. %, such as, for example between about 1.007-about 2.007 wt. % of the composition. In aspects, a preservative component of a composition comprises borate compound-polyol compound complex(es).

In aspects, a preservative component comprises one or more quaternary ammonium compounds, such as, e.g., a quaternary ammonium salt such as benzalkonium chloride. In aspects, compositions comprise benzalkonium chloride and borate-polyol complexes together, including BKC in an amount described in this paragraph.

In aspects, compositions comprise a preservative component comprising at least one borate compound, such as, e.g., boric acid, wherein the at least one borate compound is present in the composition in an amount representing between about 0.1 wt. % to about 0.5 wt. % of the composition, such as, e.g., between ~0.1-~0.4 wt. %, or ~0.1-~0.3 wt. %, e.g., ~0.2-~0.5 wt. %, ~0.3-~0.5 wt. %, such as for example ~0.2-~0.4 wt. %, or ~0.3 wt. % of the composition. In aspects, a preservative component of a composition comprises a single borate compound. In aspects, the borate compound is boric acid.

In aspects, compositions comprise a preservative component comprising one or more polyol compounds, wherein the polyol compound(s) are present in the composition in an amount representing between about 0.6 wt. % to about 2.2 wt. % of the composition, such as, e.g., between ~0.8-~2.2 wt. %, ~0.7-~2.2 wt. %, ~0.8-~2.2 wt. %, ~0.9-~2.2 wt. %, or ~1-~2.2 wt. %, e.g., ~0.6-~2.2 wt. %, ~0.6-~2 wt. %, ~0.6-~1.8 wt. %, ~0.6-~1.6 wt. %, ~0.6-~1.4 wt. %, ~0.6-~1.2 wt. %, or ~0.6-~1.1 wt. %, such as for example between ~0.7-~1.8 wt. %, ~0.8-~1.4 wt. %, ~0.9-~1.2 wt. %, or ~1 wt. %, such as about 1.05 wt. %. In aspects, a preservative component comprises 2 or more polyol compounds present together in an amount described in this paragraph. In aspects, a preservative component comprises mannitol and propylene glycol, which together are present in an amount described in this paragraph. In some aspects, the total polyols of a composition can comprise between about 0.5 wt. to about 3 wt. % of a composition, such as, e.g., ~0.75-~3 wt. %, ~1-~3 wt. %, ~1.25-~3 wt. %, ~1.5-~3 wt. %, ~1.75-~3 wt. %, or ~2-~3 wt. %, e.g., ~0.5-~2.75 wt. %, ~0.5-~2.5 wt. %, ~0.5-~2.25 wt. %, or ~0.5-~2 wt. %, e.g., ~1-~2 wt. % of the composition.

In aspects, compositions comprise a preservative component comprising mannitol, wherein mannitol is present in the composition in an amount representing between about 0.1 wt. % to about 1 wt. % of the composition, such as, e.g., between ~0.15-~1 wt. %, ~0.2-~1 wt. %, ~0.25-~1 wt. %, ~0.3-~1 wt. %, e.g., ~0.1-~0.8 wt. %, ~0.1-~0.6 wt. %, ~0.1-~0.5 wt. %, ~0.1-~0.4 wt. %, ~0.1-~0.3 wt. %, such as, e.g., between ~0.15-~0.8 wt. %, ~0.2-~0.6 wt. %, ~0.25-~0.4 wt. %, ~0.25-~0.35 wt. %, or, e.g., about 0.3 wt. % of the composition.

In aspects, compositions comprise a preservative component comprising propylene glycol, wherein propylene glycol is present in the composition in an amount representing between about 0.5 wt. % to about 1.2 wt. %, such as, e.g., between ~0.55-~1.2 wt. %, ~0.6-~1.2 wt. %, ~0.65-~1.2 wt. %, ~0.7-~1.2 wt. %, or ~0.75-~1.2 wt. %, e.g., ~0.5-~1.1 wt. %, ~0.5-~1 wt. %, ~0.5-~0.9 wt. %, or ~0.5-~0.8 wt. %, such as, e.g., ~0.55-~1.1 wt. %, ~0.6-~1 wt. %, ~0.65-~0.9 wt. %, ~0.7-~0.8 wt. %, or, e.g., about 0.75 wt. % of the composition.

In aspects, compositions comprise a preservative component comprising borate-polyol complex(es), wherein borate-polyol complex(es) are present in the composition in an amount representing between about 0.5 wt. % to about 6 wt. %, such as, e.g., between ~0.75-~5 wt. %, ~0.1-~5 wt. %, ~1.25-~5 wt. %, ~1.5-~5 wt. %, ~1.75-~5 wt. %, ~2-~5 wt. %, e.g., ~0.5-~5 wt. %, ~0.5-~4 wt. %, ~0.5-~3 wt. %, ~0.5-~2 wt. %, ~0.5-~1 wt. %, such as, for example, between about ~0.6-~5 wt. %, ~0.7-~4 wt. %, ~0.8-~3 wt. %, ~0.9-~2.5 wt. %, or, e.g., between about 1-about 2 wt. % of the composition.

In aspects, compositions comprise a preservative component comprising at least one quaternary ammonium compound, wherein the quaternary ammonium compound(s) are present in the composition in an amount of between about 0.005 wt. % to about 0.2 wt. % of the composition, such as, e.g., between ~0.005-~0.15 wt. %, ~0.005-~0.15 wt. %, ~0.005-~0.1 wt. %, ~0.005-~0.05 wt. %, ~0.005-~0.01 wt. %, ~0.005-~0.009 wt. %, or ~0.005-~0.0.008 wt. %, e.g., ~0.0055-~0.2 wt. %, ~0.006-~0.2 wt. %, ~0.0065-~0.2 wt. %, ~0.007-~0.0.2 wt. %, such as, for example, between about ~0.0055-~0.15 wt. %, ~0.006-~0.1 wt. %, ~0.0065-~0.05 wt. %, ~0.0065-~0.01 wt. %, ~0.0065-~0.009 wt. %, ~0.0065-~0.008 wt. %, ~0.0065-~0.0075 wt. %, or, e.g., about 0.007 wt. % of the composition. In certain aspects, compositions comprise less than 0.005 wt. % (but an at least detectable amount) of quaternary ammonium compound(s), such as quaternary ammonium salts, e.g., benzalkonium chloride, such as, e.g., benzalkonium chloride can be present in compositions in an amount of ~0.003-0.2 wt. %, or, e.g., <0.005 wt. %. In aspects, similar or equivalent amounts of sodium chlorite (Purite) can be used.

Preservative Means

In this and any other ingredient aspect of the invention, the invention also can be characterized as comprising a "means" for carrying out the referenced function associated with the ingredient/component/compound such as, here, preserving composition(s) of the invention. In such a respect, any known equivalents of such named agents can also be, e.g., are, incorporated into compositions or methods of the invention. As with other sections similar described herein, any of the components of the invention can be, where suitable, described as means (e.g., the above-described preservation agents/compounds or components can be described as active pharmaceutical ingredient (API) preservation means or means for preserving the active pharmaceutical ingredient(s) of the composition.

Penetration Enhancer

In aspects, compositions provided by the invention comprise a penetration enhancer component (penetration component) comprising one or more ophthalmologically suitable penetration enhancing agent(s)/constituent(s) ("penetration enhancers"). In alternative aspects, compositions provided by the invention do not comprise a penetration enhancer, such that the composition(s) provided by the invention are characterizable as "penetration enhancer free." In aspects, compositions lack any significant amount of any agent that is solely/mostly characterizable as a penetration enhancer or that is at all characterized as a penetration enhancer.

In aspects, compositions provided by the invention comprise a penetration enhancer component comprising one or more penetration enhancers which, either alone or in combination, provide detectable or significant enhanced (e.g., increased) penetration of one or more brinzolamide compounds, one or more brimonidine compounds, or both brinzolamide compound(s) and brimonidine compound(s) into ocular tissue over the same composition lacking such a penetration enhancer component.

In aspects, a penetration enhancer component of a composition detectably or significantly increases the amount of one or more brinzolamide compounds capable of penetrating ocular tissue in a given time period, such as, e.g., by at least about 0.1%, ≥~0.2%, ≥~0.4%, ≥~0.6%, ≥~0.8%, ≥~1%, ≥~3%, ≥~5%, ≥~7%, ≥~10%, ≥~15%, or ≥~20%, such as ≥~25%, ≥~50%, ≥~75%, or ≥~100% or any other significant amount. Time periods in this and similar aspects can mean, e.g., ≥0.5 days, ≥1 day, ≥3 days, ≥5 days, ≥1 week, ≥2 weeks, ≥1 month, ≥3 months, ≥6 months, etc. In aspects, such percentage increases occur over following a dosage regimen for such a period of time, according to methods described herein.

In aspects, a penetration enhancer component of a composition detectably or significantly increases the amount of one or more brimonidine compounds, e.g., brimonidine tartrate, capable of penetrating ocular tissue in a given time period, such as, e.g., by at least about 0.1%, ≥~0.2%, ≥~0.4%, ≥~0.6%, ≥~0.8%, ≥~1%, ≥~3%, ≥~5%, ≥~7%, ≥~10%, ≥~15%, or ≥~20%, such as ≥~25%, ≥~50%, ≥~75%, or ≥100% or any other significant amount.

In aspects, a penetration enhancer component of a composition detectably or significantly increases the amount of one or more brinzolamide compounds and one or more brimonidine compounds, e.g., brimonidine tartrate, capable of penetrating ocular tissue in a given time period, such as, e.g., by at least about 0.1%, ≥~0.2%, ≥~0.4%, ≥~0.6%, ≥~0.8%, ≥~1%, ≥~3%, ≥~5%, ≥~7%, ≥~10%, ≥~15%, or ≥~20%, such as ≥~25%, ≥~50%, ≥~75%, or ≥~100% or any other significant amount.

In aspects, a penetration enhancer component of a composition detectably or significantly increases the rate of penetration of ocular tissue of one or more brinzolamide compounds, such as, e.g., increasing the rate of penetration by at least about 0.1%, ≥~0.2%, ≥~0.4%, ≥~0.6%, ≥~0.8%, ≥~1%, ≥~3%, ≥~5%, ≥~7%, ≥~10%, ≥~15%, or ≥~20%, such as ≥~25%, ≥~50%, ≥~75%, or ≥~100% or any other significant amount.

In aspects, a penetration enhancer component of a composition detectably or significantly increases the rate of penetration of ocular tissue of one or more brimonidine compounds, such as, e.g., increasing the rate of penetration by at least about 0.1%, ≥~0.2%, ≥~0.4%, ≥~0.6%, ≥~0.8%, ≥~1%, ≥~3%, ≥~5%, ≥~7%, ≥~10%, ≥~15%, or ≥~20%, such as ≥~25%, ≥~50%, ≥~75%, or ≥~100% or any other significant amount.

In aspects, a penetration enhancer component of a composition detectably or significantly increases the rate of penetration of ocular tissue of one or more brinzolamide compounds and one or more brimonidine compounds, such as, e.g., increasing the rate of penetration by at least about 0.1%, ≥~0.2%, ≥~0.4%, ≥~0.6%, ≥~0.8%, ≥~1%, ≥~3%, ≥~5%, ≥~7%, ≥~10%, ≥~15%, or ≥~20%, such as ≥~25%, ≥~50%, ≥~75%, or ≥~100% or any other significant amount.

In aspects, one or more compounds of a composition providing a detectable or significant penetration enhancement effect can also provide one or more additional DOS effects, such as chelation effect, buffering effect, solubilization effect, preservative effect, etc. For example, in aspects, one or more penetration agents can provide both preservative and penetration enhancement effect. In aspects, one or more penetration agents can provide both solubilization and penetration enhancement effect(s).

In aspects, the invention provides composition(s) comprising ophthalmologically suitable penetration enhancer(s) effective (e.g., agents capable of demonstrating one or more of the characteristics of a penetration enhancement described above in the context of a composition of the invention) at pH range of between, e.g., ~4.0-~9.5, such as between ~5.0-~9.0, e.g., or, e.g., ~5.5-~8.5. In aspects, a penetration enhancer compound of the composition(s) herein does not detectably or significantly negatively impact any other component of the formulation, such as, e.g., they do not detectably or significantly reduce the efficacy or functionality of any one or more brinzolamide compounds, brimonidine compound (e.g., reduce efficacy in treating IOP), or any other API or excipient present in the composition.

In aspects, compositions provided by the invention comprise any pharmaceutically acceptable and ophthalmologically suitable penetration enhancer. In aspects, compositions provided by the invention comprise any pharmaceutically acceptable and ophthalmologically suitable penetration enhancer capable of detectably or significantly enhancing (increasing) the penetration of one or more brinzolamide compounds, one or more brimonidine compounds or both brinzolamide compound(s) and brimonidine compound(s) into ocular tissue.

In certain aspects, a penetration enhancer component comprises a penetration enhancer selected from a group comprising one or more of a water-soluble synthetic polymer (e.g., polyvinylpyrrolidone, polyvinyl alcohol), a polyoxyl castor oil (e.g., a cremophor), fatty acid esters including fatty acid ester derivatives (e.g., polysorbate 80 or myrj (ethylene glycol monostearate)), polyoxyethylene fatty ethers (e.g., brij), quaternary ammonium compounds, or compounds belonging to two or more such groups.

Exemplary penetration enhancers include, e.g., quaternary ammonium compound(s), such as, e.g., quaternary ammonium salts such as benzalkonium chloride, sodium chlorite, tyloxapol, a fatty acid ester including fatty acid ester derivatives, polyoxyethylene fatty ethers, polyoxyethylene sorbitan fatty acid esters, a polyoxyl castor oil (e.g., polyoxyl-35 castor oil), tocopheryl polyethylene glycol succinate (TPGS), poly-arginine, polyserine, tromethamine (tris), sesame seed oil or oils having similar compositions and functional characteristics suitable for ophthalmic use, etc. or any ophthalmologically suitable derivatives, e.g., salts thereof, or combinations of any two or more such compounds, or equivalents thereof. In aspects, a compound may belong to one or more such groups of penetration enhancer compounds described in this paragraph.

Penetration Enhancer Amount

In aspects, a penetration enhancement component of a composition provided by the invention can be present in any pharmaceutically acceptable and ophthalmologically suitable and effective amount. In aspects, a penetration enhancement component of a composition, comprising one or more constituents, is present in a composition in an amount representing between about 0.02 wt. % to about 0.7 wt. % of the composition, such as, e.g., between ~0.05-~0.7 wt. %, ~0.1-~0.7 wt. %, ~0.15-~0.7 wt. %, ~0.2-~0.7 wt. %, ~0.25-~0.7 wt. %, or ~0.3-~0.7 wt. %, e.g., between ~0.02-~0.65 wt. %, ~0.02-~0.6 wt. %, ~0.02-~0.55 wt. %, ~0.02-~0.5 wt. %, ~0.02-~0.45 wt. %, ~0.02-~0.4 wt. %, ~0.02-~0.35 wt. %, ~0.02-~0.3 wt. %, such as, for example, between ~0.022-~0.065 wt. %, ~0.024-~0.06 wt. %, ~0.026-~0.055 wt. %, ~0.028-~0.05 wt. %, ~0.028-~0.045 wt. %, ~0.028-~0.04 wt. %, such as, e.g., ~0.03 wt. %, as in about 0.032 wt. %.

Quaternary Ammonium Compounds

In aspects, a penetration enhancement component suitable for use in the present invention for increasing the penetration of one or more brinzolamide compounds, one or more brimonidine compounds, or both brinzolamide and brimonidine compounds (which, again, may provide additional functional activity) comprises quaternary ammonium compounds. In aspects, such quaternary ammonium compounds are pharmaceutically acceptable and ophthalmologically suitable quaternary ammonium salt(s).

Quaternary Ammonium Salts

In aspects, a penetration enhancement component can comprise one or more quaternary ammonium salts. Here, a quaternary ammonium salt is a quaternary ammonium compound in which organic radicals have been substituted for all four hydrogens of the original ammonium cation. Such compounds typically have a structure comprising a central nitrogen atom which is joined to four organic radicals and one acid radical. The organic radicals may be alkyl, aryl, or aralkyl, and the nitrogen can be part of a ring system. Examples of such compounds include Benzalkonium Chloride (e.g., CAS RN: 8001-54-5); Benzethonium Chloride CAS 121-54-0; Cetalkonium Chloride (e.g., CAS 122-18-9); Cetrimide (e.g., CAS 8044-71-1); Cetrimonium Bromide (e.g., CAS 57-09-0); Cetylpyridinium Chloride (e.g., CAS 123-03-5); and Stearalkonium Chloride (e.g., CAS 122-19-0), provided that typically the quaternary ammonium compound included in any formulation provided herein is of a nature and amount that is ophthalmologically safe and having the properties specified herein (e.g., in terms of brinzolamide compound, brimonidine compound, or both brinzolamide and brimonidine compound penetration enhancement).

In aspects, a penetration enhancer component can comprise benzalkonium chloride, benzethonium chloride, benzyltrimethylammonium chloride (also known as Triton B or trimethylbenzylammonium hydroxide), cetalkonium chloride, cetrimide, cetrimonium bromide, cetylpryidinium chloride, stearalkonium chloride, lauryltrimethylammonium chloride (also known as dodecyltrimethylammonium chloride), etc. In some embodiments, the ophthalmic formulations of the invention lack any quaternary ammonium salt.

Benzalkonium Chloride

In aspects, a penetration component of compositions provided by the invention comprises one or more quaternary ammonium compounds, such as, e.g., one or more quaternary ammonium salts, e.g., one or more benzalkonium chloride (BKC) compound(s). Benzalkonium chlorides may also be referred to as alkyl dimethyl benzyl ammonium chlorides (ADBAC), alkyl dimethyl (phenylmethyl) chlorides, or ammonium alkyl dimethyl benzyl chlorides. In aspects, BKC can serve as a penetration enhancer, preservative, solubilizer, or any combination thereof. That is, in aspects, BKC can provide a detectable or significant increase in the penetration, e.g., the bioavailability, of one or more ingredients of the composition(s) or both, can provide preservation qualities such as those described herein or in the art, or, e.g., can detectably or significantly improve upon the solubilization of any one or more APIs, such as any one or more brinzolamide compounds, any one or more brimonidine compounds, or both brinzolamide and brimonidine compounds. In aspects, the penetration enhancement component of compositions provided by the invention comprises benzalkonium chloride.

In aspects, a penetration enhancer component of a composition comprises benzalkonium chloride, wherein the benzalkonium chloride is present in composition in an amount representing at least about 0.005 wt. % of the composition, such as, e.g., ≥0.0055 wt. %, ≥0.006 wt. %, ≥0.0065 wt. %, or ≥0.007 wt. % of the composition. In aspects, benzalkonium chloride is present in the composition in an amount which is less than about 0.3 wt. %, such as ≤~0.28 wt. %, ≤~0.26 wt. %, ≤~0.24 wt. %, ≤~0.22 wt. %, or ≤~0.2 wt. % of the composition. In aspects, benzalkonium chloride is present in the composition in an amount of between about 0.005 wt. % to about 0.2 wt. % of the composition, such as, e.g., between ~0.005-~0.15 wt. %, ~0.005-~0.15 wt. %, ~0.005-~0.1 wt. %, ~0.005-~0.05 wt. %, ~0.005-~0.01 wt. %, ~0.005-~0.009 wt. %, or ~0.005-~0.0.008 wt. %, e.g., ~0.0055-~0.2 wt. %, ~0.006-~0.2 wt. %, ~0.0065-~0.2 wt. %, ~0.007-~0.0.2 wt. %, such as, for example, between about ~0.0055-~0.15 wt. %, ~0.006-~0.1 wt. %, ~0.0065-~0.05 wt. %, ~0.0065-~0.01 wt. %, ~0.0065-~0.009 wt. %, ~0.0065-~0.008 wt. %, ~0.0065-~0.0075 wt. %, or, e.g., about 0.007 wt. % of the composition. In certain aspects, benzalkonium chloride, as disclosed elsewhere, can be below 0.005 wt. %, such as, e.g., ~0.0045 wt. %, ~0.004 wt. %, ~0.0035 wt. %, or, e.g., about 0.003 wt. %. In some such aspects, compositions include one or more other agent(s) that provide one or more of the other functions performed by BKC, such as, e.g., penetration enhancement, preservation, or both. In aspects, one or more of such function(s) are performed by, e.g., tyloxapol (penetration effect), or, e.g., a borate-polyol complex (preservation effect).

In aspects, benzalkonium chloride is present in compositions provided by the invention, which is detectably or significantly higher than that provided in the FDA approved and presently on-market brinzolamide-brimonidine combination product (brinzolamide/brimonidine tartrate ophthalmic suspension) presently sold as Simbrinza® (comprising 0.003 wt. % benzalkonium chloride) (described further elsewhere). In aspects, compositions herein comprise an amount of benzalkonium chloride, which is detectably or significantly greater than 0.003 wt. % of the composition. In aspects, compositions herein comprise at least about 60% more, e.g., ≥~70%, ≥~80%, ≥~90%, ≥~100%, ≥~150%, ≥~200%, ≥~250%, ≥~300%, ≥~350%, ≥~400%, ≥~450%, ≥~500%, ≥~550%, or ≥~600% more benzalkonium chloride than that of the presently on-market brinzolamide/brimonidine tartrate ophthalmic suspension.

Tyloxapol

In aspects, a penetration enhancement component of a composition comprises tyloxapol, wherein the tyloxapol is present in a composition in an amount representing between about 0.015 wt. % to about 0.5 wt. % of the composition, such as, e.g., between ~0.01-~0.5 wt. %, ~0.015-~0.5 wt. %, ~0.02-~0.5 wt. %, or ~0.025-~0.5 wt. %, e.g., ~0.015-~0.45 wt. %, ~0.015-~0.4 wt. %, ~0.015-~0.35 wt. %, ~0.015-~0.3 wt. %, or ~0.015-~0.25 wt. %, such as, for example between ~0.016-~0.45 wt. %, ~0.018-~0.4 wt. %, ~0.02-~0.35 wt. %, ~0.022-~0.3 wt. %, such as, e.g., about 0.025 wt. % of the composition.

Polysorbates

In aspects, compounds suitable for use in the present invention for increasing the penetration of brinzolamide compound(s), brimonidine compound(s), or both brinzolamide and brimonidine compound(s) within ocular tissue, which may further provide additional functional activity (e.g., may provide surfactant activity, or, e.g., antimicrobial (e.g., preservative) activity) include but may not be limited to polyoxyethylene sorbitan fatty acid esters (e.g., polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65). In some aspects, the polyoxyethylene sorbitan fatty acid ester can be a polyoxyethylene sorbitan oleate/polyoxyethylene sorbitan mono-oleate ester (e.g., polysorbate 80). In some aspects, characteristics of such a polyoxyethylene sorbitan fatty acid ester may be such that in specific concentrations the compound becomes unsuitable for ocular applications such as those described herein, as may be the case with, for example, polysorbate 20, as negative effects on ocular cells are possible. Hence in aspects, polysorbate 60, polysorbate 65, or polysorbate 80 may be more suitable for the formulations described herein.

According to certain embodiments, a penetration enhancer can be characterized as a nonionic surfactant and emulsifier, non-irritating to ocular tissue, and capable of increasing the penetration of brinzolamide compound(s), brimonidine compound(s), or both brinzolamide and brimonidine compound(s) within ocular tissue, including any such compound modified in such a way that does not lead to a detectable or significant difference with respect to some, most, or generally all such characteristics with respect to an amount of polysorbate 80 that achieves a statistically similar level of penetration of the brinzolamide compound(s), brimonidine compound(s), or both brinzolamide and brimonidine compound(s). In aspects such an ingredient/component can be characterized as clear in aqueous solution. In certain specific aspects, a penetration enhancer can be a polyoxyethylene sorbitan fatty acid ester making up at least about 0.2%, at least about 0.5%, at least about 0.85%, or at least about 1% of the composition, such as between about 0.1- about 3% of the composition, such as between about 0.15- about 2.5%, or for example such as making up between about 0.2-2% of the formulation, e.g., between about 0.5%- about 1.5% of the formulation. In aspects, the polyoxyethylene sorbitan fatty acid ester is polysorbate 80.

Penetration Enhancer Means

In this and any other ingredient aspect of the invention, the invention also can be characterized as comprising a "means" for enhancing the penetration into ocular tissue of one or more API(s) of the composition (e.g., one or more brinzolamide compounds, one or more brimonidine compounds, or both brinzolamide and brimonidine compounds. In such a respect, any known equivalents of such named agents can also be, e.g., are, incorporated into compositions or methods of the invention. As with other sections similar described herein, any of the components of the invention can be, where suitable, described as means (e.g., the above-described preservation agents/compounds or components can be described as active pharmaceutical ingredient (API) penetration enhancer means or means for increasing the penetration into ocular tissue of one or more active pharmaceutical ingredient(s) of the composition.

Ratios of Components

Provided in Table 1 are exemplary amounts of exemplary ingredients, which in aspects are present in compositions provided by the invention, along with exemplary ratios between them:

TABLE 1

Exemplary Ingredients and Ratios

| Compound Description | Exemplary Compound | Exemplary Amount (wt. %) |
| --- | --- | --- |
| Borate compound | Boric acid | 0.1-0.5 |
| Polyol | Mannitol | 0.1-1 |
| Polyol | Propylene glycol | 0.5-1.2 |
| Polyols, total | Mannitol + Propylene glycol | 0.6-2.2 |
| Borate-polyol complex | Borate-Polyol Complex (Boric acid-Mannitol; Boric acid-Propylene glycol) | 0.5-6 |
| APIs, total (Brinzolamide compound(s) + Brimonidine compound(s) | Brinzolamide (free) + brimonidine tartrate | 0.11-10.5 |
| Quaternary ammonium compound | Quaternary ammonium salt, e.g., benzalkonium chloride | 0.005-0.2 |

| Ratio | Exemplary Ratio Range | Exemplary Ratio(s) |
| --- | --- | --- |
| Boric acid:Mannitol | 1:0.2-1:10 | 1:1 |
| Boric acid:Propylene glycol | 1:1-1:12 | 1:2.5 |
| Borate:Polyols (total) | 1:1.2-1:22 | 1:3.5 |
| Borate-polyol complex:APIs (total) | 1:0.01-1:21 | 1:0.6-1:1.2 |
| Borate-polyol complex: Benzalkonium chloride | 1:0.4-1:1200 | 1:140-1:300 |
| Mannitol:Benzalkonium chloride | 1:2-1:200 | 1:43 |
| Propylene glycol:Benzalkonium chloride | 1:0.1-1:240 | 1:0.009 |
| Benzalkonium chloride:APIs (total) | 1:0.55-1:2100 | 1:171 |

*Note:
ratios in Table 1 represent the ratios of each respective ingredient's percentage by weight of the of the composition.

In further aspects, compositions provided by the invention comprise a molar ratio of a borate compound to polyol compound(s) present in the composition of between about 1:0.1 to about 1:10, such as, e.g., ~1:0.1-~1:8.5, ~1:0.1-~1:8, ~1:0.1-~1:7.5, ~1:0.1-~1:7, ~1:0.1-~1:6.5, ~1:0.1-~1:6, ~1:0.1-~1:5.5, ~1:0.1-~1:5, ~1:0.1-~1:4.5, ~1:0.1-~1:4:1:0.1-~1:3.5, ~1:0.1-~1:3, or ~1:0.1-~1:2.5, e.g., ~1:0.12-~1:10, ~1:0.14-~1:10, ~1:0.16-~1:10, ~1:0.18-~1:10, ~1:0.2-~1:10, ~1:0.22-~1:10, ~1:0.24-~1:10, such as, for example, between about 1:0.12-about 1:9, ~1:0.14-~1:8, ~1:0.16-~1:7, ~1:0.18-~1:6, ~1:0.2-~1:5, ~1:0.22-~1:4, ~1:0.24-~1:3, or, e.g., between about 1:0.25 and about 1:2.5.

In aspects, the invention provides compositions, wherein the ratio of the brimonidine compound to the brinzolamide compound in the composition is between about 10:1-about 1:5.

In aspects, the invention provides compositions, wherein the ratio of the brimonidine compound to the brinzolamide compound in the composition is about 5:1.

For example, in one aspect, the invention provides a pharmaceutically acceptable and ophthalmologically suitable composition comprising one or more brinzolamide compounds in an amount of about 0.1 wt. % to about 10 wt. %, one or more brimonidine compounds in an amount of about 0.01 wt. % to about 0.5 wt. %, one or more borate-polyol complexes in an amount of about 0.5 to 6 wt. %, and one or more quaternary ammonium compounds, e.g., a quaternary ammonium salt, such as, for example, benzalkonium chloride, wherein the benzalkonium chloride concentration is greater than 0.005 wt. % but less than 0.02% wt. %.

In certain aspects, compositions comprise benzalkonium chloride in an amount greater than about 0.005 wt. % and wherein the composition does not comprise a detectable or significant amount of borate-polyol complex(es).

In certain aspects, compositions can comprise benzalkonium chloride in an amount of less than about 0.005 wt. %. In aspects, benzalkonium chloride is present in an amount of between about 0.003-about 0.2 wt. %. In aspects wherein the benzalkonium chloride is below 0.005 wt. %, the ratio of borate-polyol complex to benzalkonium chloride can be, for example, between, e.g., ~1:0.0005-~1:0.4; the ratio of mannitol to benzalkonium chloride can be between, e.g., ~1:0.003-~1:2; the ratio of propylene glycol to benzalkonium can be between, e.g., ~1:0.0025-~1:0.4; and the ratio of benzalkonium chloride to the total APIs can be between, e.g., 1:0.55-1:3500.

In another specific embodiment, the invention provides a pharmaceutically acceptable and ophthalmologically suitable composition comprising brinzolamide in an amount of about 0.1 wt. %, brimonidine tartrate in an amount of about 0.2 wt. %, and one or more pharmaceutically acceptable excipients selected from boric acid in an amount of about 0.3 wt. %, propylene glycol in an amount of about 0.75 wt. %, tyloxapol in an amount of about 0.025 wt. %, one or more carbomers in an amount of about 0.4 wt. % by weight, mannitol in an amount of about 0.3 wt. %, sodium chloride in an amount of about 0.025 wt. %, and water, wherein the benzalkonium chloride concentration is greater than 0.005 wt. % but less than 0.02 wt. %.

Additional Active Ingredients (or Lack Thereof)

As noted above, in aspects, compositions provided by the invention comprise two or more APIs. In aspects, compositions herein comprise at least one CAI and at least one alpha-2-adrenergic agonist compounds. In aspects, compositions comprise no detectable or significant amount of any additional active pharmaceutical ingredient than such APIs. In aspects, compositions comprise no detectable or significant amount of any APIs other than brinzolamide compound(s) and brimonidine compound(s). In aspects, compositions include only one type of each of such compound.

In certain aspects, compositions provided by the invention comprise at least one CAI, at least one alpha-2-adrenergic agonist, and an effective and suitable amount of at least one more additional pharmaceutically acceptable and ophthalmologically suitable API. In aspects, such additional API(s) are not CAI(s), not alpha-2-adrenergic agonis(s) or are not either thereof.

According to aspects, compositions of the invention can comprise one or more additional ophthalmologically suitable APIs (in addition to the CAI (e.g., brinzolamide) compound(s) and the alpha-2-adrenergic agonist (e.g., brimonidine, such as brimonidine tartrate) compound(s)), such additional API(s) being present in any amount effective for carrying out intended effects, typically including treatment of one or more conditions relating to the eye. In aspects, an additional API can be present in an amount effective in detectably or significantly increasing the efficacy of the CAI compound(s), detectably or significantly increasing the efficacy of the alpha-2-adrenergic agonist compound(s), or detectably or significantly increasing the therapeutic usefulness or clinical efficacy of the composition, e.g., demonstrating a detectable or significant beneficial effect in the recipient of the composition. In aspects, the one or more additional APIs can provide a detectable or significant, e.g., clinically significant effect, such as, e.g., intraocular pressure reducing activity, antimicrobial activity, anti-inflammatory activity, or activity associated with any one or more ophthalmic conditions or symptoms related to or associated with glaucoma, elevated intraocular pressure, or both.

In aspects, composition(s) provided by the invention can comprise one or more additional APIs wherein the one or more additional APIs are stable within the composition(s) at a pH of between, e.g., ~5.0-~9.0, such as between ~6.0-~9.0, e.g., ~6.5-~8.5, for a period of at least 2 weeks post-manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or more.

In aspects, any ophthalmologically suitable and pharmaceutically acceptable API can be used. In aspects, any one or more additional APIs of the composition(s) provided by the invention do not detectably or significantly negatively impact any other component of the formulation, such as, e.g., they do not detectably or significantly reduce the efficacy of any one or more brinzolamide compound(s), any one or more brimonidine compound(s), or reduce any functional effect (e.g., intraocular pressure reduction effect of brinzolamide compound(s), brimonidine compound(s) or both), of any other API or excipient present in the composition.

In aspects, APIs present in a composition provided by the invention in addition to the one or more CAI(s) and one or more alpha-2-adrenergic agonist(s), can be any one or more of, e.g., antineoplastic agent, anti-allergic agent, glaucoma-treating agent, intraocular pressure reducing agent, antimicrobial agent, anti-inflammatory agent, etc., such as any ophthalmologically suitable compound which imparts a benefit to the eye of the recipient. In aspects, compositions provided by the invention can comprise one or more pharmaceutically acceptable and ophthalmological anti-microbial agents, e.g., an antibacterial, a synthetic antibacterial, an antifungal, a synthetic antifungal, wherein the anti-microbial agent is present in an amount effective in detectably or significantly treating, preventing, or inhibiting development of or progression of a microbial growth, e.g., a bacterial growth or a fungal growth.

In aspects, one or more additional active pharmaceutical ingredients can provide a detectable or significant increase in anti-inflammatory strength, effect, or activity of the composition. In aspects, the one or more additional APIs can provide a detectable or significant increase in the microbial inhibition or killing strength or activity of the composition (e.g., increasing the number of microbial species killed in significant number, significantly increasing the number of microbes killed in a significant number of subjects, etc.).

In one aspect, the invention provides compositions comprising one or more antimicrobials, e.g., one or more antibiotics. In certain aspects, suitable antibacterial/antibiotics can be any ophthalmologically suitable antibacterial/antibiotic. In aspects, such an antibiotic can be a quinolone antibiotic, such as those described in, e.g., US patent application number 17, 458,447. In aspects, suitable antibacterial/ antibiotics for combination therapy are, for example, aminoglycosides for example amikacin, apramycin, arbekacin, bambermycins, butirosin, dibekacin, dihydrostreptomycin, fortimicin(s), gentamicin, tobramycin, isepamicin, kanamycin, micronomicin, neomycin, neomycin undecylenate, netilmicin, paromomycin, ribostamycin, sisomicin, spectinomycin, streptomycin, trospectomycin; amphenicois for example azidamfenicol, chloramphenicol, florfenicol, thiamphenicol), ansamycins (e.g., rifamide, rifampin, rifamycin sv, rifapentine, rifaximin; beta-lactams for example carbacephems include loracarbef; carbapenems for example biapenem, imipenem, meropenem, panipenem; cephalosporins for example cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, ceifuzonam, cephacetrile sodium, cephalexin, cephaloglycin, cephaloridine, cephalosporin, cephalothin, cephapirin sodium, cephradine, pivcefalexin; cephamycins for example cefbuperazone, cefmetazole, cefininox, cefotetan, cefoxitin; monobactams for example aztreonam, carumonam, tigemonam), oxacephems, flomoxef, moxalactam; penicillins for example amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin and other like ritipenem; lincosamides for example clindamycin and lincomycin; macrolides for example azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin; polypeptides for example amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin and zinc bacitracin; tetracyclines for example apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline and, e.g., tetracycline, and pharmaceutically acceptable salts thereof, and mixtures thereof. In aspects, suitable synthetic antibacterials suitable for combination therapy are, for example, 2,4-diaminopyrimidines for example brodimoprim, tetroxoprim, trimethoprim; nitrofurans for example furaltadone, furazolium chloride, nifuradene, nifuratel, nifurfoline, nifurpirinol, nifurprazine, nifurtoinol, nitrofurantoin; quinolones (as mentioned previously) and analogs for example cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin; sulfonamides for example acetyl sulfamethoxypyrazine, benzylsulfamide, chloramine-b, chloramine-t, dichloramine-t, N2-Formylsulfisomidine, N4-β-d-Glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfarnerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, 4-sulfanilamidosalicylic acid, N4-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole; sulfones for example acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone; and others like clofoctol, hexedine, methenamine, methenamine anhydromethylene-citrate, methenamine hippurate, methenamine mandelate, methenamine sulfosalicylate, nitroxoline, taurolidine, and, e.g., xibornol, and any suitable pharmaceutically acceptable salts thereof, and any suitable mixtures of any thereof.

In general, any description of an additional API herein with respect to compositions implicitly provides support for the use of such additional API(s) in combination therapy methods, wherein such agents are administered/delivered separately to a subject, such as a patient, in combination with composition(s) of the invention (and vice versa). In aspects, antifungal agents suitable for combination compositions or combination therapy with compositions of the invention are, for example, polyenes e.g., amphotericin b, candicidin, dennostatin, filipin, fungichromin, hachimycin, hamycin, lucensomycin, mepartricin, natamycin, nystatin, pecilocin, perimycin, azaserine, griseofulvin, oligomycins, neomycin undecylenate, pyrrolnitrin, siccanin, tubercidin, and, e.g., viridin, and pharmaceutically acceptable salts thereof, and mixtures thereof. Examples of suitable synthetic antifungals include, e.g., allylamines for example butenafine, naftifine, terbinafine, imidazoles for example bifonazole, butoconazole, chlordantoin, chlormiidazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole; thiocarbamates for example tolciclate, tolindate, tolnaftate; triazoles for example fluconazole, itraconazole, saperconazole, terconazole and others like acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, and, e.g., zinc propionate, and pharmaceutically acceptable salts thereof, and mixtures thereof. In aspects, antineoplastic agents suitable for combination therapy are, for example, ophthalmologically suitable forms of mitomycin C or fluorouracil (5FU), or Intron A, or ophthalmologically suitable forms of methotrexate, cytarabine (Ara-C), thiotepa, chlorambucil, dacarbazine, or temozolamide, etc. In aspects, anti-allergic agents suitable for combination therapy or combination compositions are, for example, ophthalmologically suitable antihistamines (e.g., levocabastine, emedastine, bilastine, cetirizine, etc.), ophthalmologically suitable mast-cell stabilizers (e.g., cromolyn, nedocromil, etc.), ophthalmologically suitable dual-activity agents (providing both antihistamine and mast-cell inhibition activity, such as, e.g., olopatadine, bepotastine, alcaftadine, etc.), ophthalmologically suitable corticosteroids (e.g., loteprednol etabonate, loteprednol, mapracorat, prednisolone acetate, prednisolone phosphate, dexamethasone, etc.), ophthalmologically suitable prostaglandin analogs, such as, e.g., latanoprost, bimatoprost, travoprost, unoprostone, etc., ophthalmologically suitable non-steroidal anti-inflammatory drugs (such as, e.g., those disclosed above, or, e.g., specifically be, e.g., diclofenac sodium, nepafenac, etc.), ophthalmologically suitable decongestants (e.g., brimonidine, etc.), ophthalmologically suitable immunomodulators (e.g., cyclosporine A, tacrolimus, etc.) and others such as ophthalmologically suitable *cannabis* preparations, immunobiologicals, etc. In certain aspects, intraocular pressure-treating agents or glaucoma-treating agents suitable for combination therapy are, for example, beta blockers (e.g., nonselective beta blockers such as, e.g., timolol maleate, levobunolol, carteolol, metipranolol, etc. or, e.g., selective beta blockers such as, e.g., betaxolol, etc.), mimotics (e.g., pilocarpine, etc.), carbonic anhydrase inhibitors (e.g., dorzolamide, brinzolamide, etc.), sympathomimetics (e.g., epinephrine-like sympathomimetics such as, e.g., dipivefrin, etc. or, e.g., clonidine-like sympathomimetics such as, e.g., brimonidine, apraclonidine, etc.), etc. In certain aspects, antiviral agents suitable for combination therapy are, for example, idoxuridine (IDU), iododesoxycytidine (IDC), vidarabine (Ara-A), trifluridine (TFT), aciclovir, ganciclovir, trifluridine, idoxuridine, ophthalmologically suitable formulations of valganciclovir, foscarnet, etc. In aspects, anti-mycotic agents suitable for combination therapy are, for example, ophthalmologically suitable polyenes (e.g., amphotericin B (AMB), nystatin, nytamycin (NTM), etc.), ophthalmologically suitable azoles (e.g., imidazoles or triazoles, including, e.g., miconazole (MCZ), econazole (ECZ), ketoconazole (KCZ), itraconazole (ICZ), fluconazole), voriconazole, posaconazole (PCZ), etc.), ophthalmologically suitable pyrimidines (e.g., 5-fluorocystine (5-FC), flucytosine, etc.), ophthalmologically suitable echinocandins (e.g., caspofungin (CFG), micafungin (MFG), etc.), etc.

In aspects compositions can comprise any other additional pharmaceutically acceptable and ophthalmologically suitable API, such as, e.g., emadastine, tandospirone, roscovitine, bradykinin, or PDE4 inhibitor.

In aspects, compositions can comprise any one of such additional APIs described above or combinations of 2 or more thereof, such as, e.g., 2 or more, 3 or more, 4 or more, or 5 or more thereof.

Other Excipients

In aspects, compositions provided by the invention comprise and effective amount of one or more pharmaceutically acceptable and ophthalmologically suitable excipients. In aspects, such an excipient can be any excipient which provides a detectable or significant benefit to the composition, such as those described here.

According to specific aspects, compositions provided by the invention comprises benzalkonium chloride, which, e.g., provides detectable or significant penetration enhancement effect (e.g., penetration of ocular tissue) of a brinzolamide compound, a brimonidine compound, or both brinzolamide and brimonidine compounds, and further comprise one or more pharmaceutically acceptable excipients selected from the group consisting of thickening or viscosity-enhancing component, suspension component, tonicity component, preservation component, surfactant component, buffering component, pH-adjusting component, and, e.g., a carrier component (also sometimes referred to in the art as a vehicle).

Solubilizing Component & Solubilization Means

In aspects, compositions provided by the invention comprise an effective amount of a pharmaceutically acceptable and ophthalmologically suitable solubilizing component. In aspects, the solubilizing component comprises one or more solubilizing agents/constituents, which detectably or significantly increase the solubility of one or more APIs.

In aspects, compositions comprise at least one compound which may be characterizable in certain compositions in the art as a solubilizer, however in compositions provided by the invention do not provide an effective level of, a detectable level of, or a significant contribution to, the solubilization of an API.

In certain aspects, compositions lack, generally lack, or essentially lack, etc., a solubilization component, e.g., do not comprise an effective amount of, any solubilization component which detectably or significantly increases the solubility of any one or more APIs.

In aspects, compositions can comprise any pharmaceutically acceptable and ophthalmologically suitable compound characterizable as a solubilizer, such as, e.g., benzalkonium chloride, tyloxapol, polysorbate-80, tocopheryl polyethylene glycol succinate (TPGS), polyoxyl-35 castor oil, polyarginine, polyserine, tromethamine (tris), sesame seed oil, etc. or pharmaceutically acceptable derivatives thereof or combination(s) thereof.

In aspects, benzalkonium chloride is present in compositions of the present invention, providing detectable or significant penetration enhancement effect of one or more brinzolamide compounds, brimonidine compounds, or both brinzolamide and brimonidine compounds. In aspects, benzalkonium chloride is present in an amount greater than about 0.005 wt. %, such as, e.g., between ~0.005-~0.2 wt. %, e.g., about 0.007 wt. %. In aspects, the benzalkonium of a composition does not detectably or significantly increase the solubilization of a brinzolamide compound or a brimonidine compound. In aspects, any ingredient(s) that act as solubilizers/solubilizing means in a composition exhibit significantly greater solubilization effects with respect to brinzolamide, brimonidine, or both, than any BKC in the composition.

In aspects, tyloxapol is present in compositions of the present invention, providing detectable or significant penetration enhancement effect of one or more brinzolamide compounds, brimonidine compounds, or both brinzolamide and brimonidine compounds. In aspects, tyloxapol is present in compositions in an amount of between ~0.015-~0.5 wt. %, such as, e.g., about 0.025%; however, the tyloxapol does not detectably or significantly increase the solubilization of a brinzolamide compound or a brimonidine compound.

In aspects, the invention provides compositions comprising benzalkonium chloride and tyloxapol, which provide detectable or significant penetration enhancement effect of a brinzolamide compound, a brimonidine compound, or both a brinzolamide compound and a brimonidine compound, however, neither benzalkonium chloride nor tyloxapol provide detectable or significant solubilization effect for any brinzolamide compound, brimonidine compound, or both any brinzolamide or any brimonidine compound.

Solubilization Means

In this and any other ingredient aspect of the invention, the invention also can be characterized as comprising a "means" for detectably or significantly solubilizing APIs of the invention. In such a respect, any known equivalents of such named agents can also be, e.g., are, incorporated into compositions or methods of the invention. As with other sections similar described herein, any of the components of the invention can be, where suitable, described as means (e.g., the above-described solubilizer agents/compounds or components can be described as active pharmaceutical ingredient (API) solubilization means or means for detectably or significantly solubilizing the active pharmaceutical ingredient(s) of the composition).

Viscosity-Enhancement/Suspension Component & Viscosity-Enhancing Means

In aspects, compositions provided by the invention comprise an effective amount of a pharmaceutically acceptable and ophthalmologically suitable viscosity-enhancement component (viscosity-enhancing component) component. In aspects, the viscosity-enhancement component comprises one or more viscosity-enhancing agents/constituents which detectably or significantly increase the viscosity of the composition.

In aspects, compositions provided by the invention comprise an effective amount of a pharmaceutically acceptable and ophthalmologically suitable suspension component. In aspects, the suspension component comprises one or more suspension agents/constituents which detectably or significantly increase the length of time one or more compounds of the composition, e.g., a significant amount of one or more APIs, such as, e.g., a brinzolamide compound (e.g., at least most of the API(s)), is maintained in suspension without detectable or significant settling, clumping, agglomeration, aggregation, or the like.

In aspects, compositions comprise a component which provides both detectable or significant viscosity enhancement effect and suspension effect to the composition, such that, uncontradicted, the terms "viscosity-enhancement component" and "suspension component" are functionally synonymous.

In aspects, compositions can comprise any pharmaceutically acceptable and ophthalmologically suitable compound characterizable as a viscosity-enhancing agent, a suspension agent, or both, such as, e.g., a polymer containing hydrophilic groups such as monosaccharides, polysaccharides, ethylene oxide groups, hydroxyl groups, carboxylic acids, or other charged functional groups. Examples of suitable viscosity agents include carboxyvinyl polymer, xanthan gum, gelan gum, sodium carboxymethyl cellulose, hydroxypropylmethylcellulose, povidone, polyvinyl alcohol, polyethylene glycol, alginic acid, etc. or pharmaceutically acceptable derivatives thereof or combinations thereof. In aspects, a viscosity enhancer imparts an overall viscosity of, e.g., about 15-100 cps, such as about 20-80 cps, about 20-60 cps, or about 25-50 cps (e.g., measured at about 20 degrees C.). In aspects, some, most, generally all, essentially all, or all viscosity enhancers in a composition have a molecular weight of $\geq\sim10,000$ kDa, $\geq\sim25,000$ kDa, $\geq\sim30,000$ kDa, $\geq\sim35,000$ kDa, or $\geq\sim50,000$ kDa, such as $\geq\sim60,000$ kDa.

In aspects, a viscosity-enhancing component/suspension component of compositions provided by the invention comprise a carboxyvinyl polymer characterizable as having carboxylic acid functional groups. In aspects, such carboxyvinyl polymers comprise between about 2 to about 7 carbon atoms per functional group, such as, e.g., ~2, ~3, ~4, ~5, ~6, or ~7 carbon atoms per functional group. In aspects, polymers compositions comprise one or more of, e.g., polymers Carbopol 934P, 940, and 974P. In aspects, compositions comprise Carbopol 974P (carbomer 974P).

In aspects, a viscosity-enhancement component, suspension component, or components which provide both viscosity-enhancement are present in compositions provided by the invention in an amount representing at least about 0.05 wt. % of the composition, such as, e.g., $\geq0.06$ wt. %, $\geq0.07$ wt. %, $\geq0.08$ wt. %, $\geq0.09$ wt. %, $\geq0.1$ wt. %, $\geq0.11$ wt. %, $\geq0.12$ wt. %, $\geq0.13$ wt. %, $\geq0.14$ wt. %, $\geq0.15$ wt. %, $\geq0.16$ wt. %, $\geq0.17$ wt. %, $\geq0.19$ wt. %, or $\geq0.2$ wt. %, of the composition, such as, e.g., ~0.3 wt. % or more or ~0.4 wt. % or more. In aspects, the viscosity-enhancement/suspension component is a carbomer present in an amount representing about 0.4 wt. % of the composition. In aspects, the carbomer is Carbopol 974P (carbomer 974P).

In aspects, compositions comprise a sufficient amount of a viscosity enhancement component/suspension component to effectively maintain the composition as a composition for use as an ophthalmologically suitable suspension for a period of at least about 30 minutes after mixing, e.g., $\geq\sim1$ hour, $\geq\sim1.5$ hours, $\geq\sim2$ hours, $\geq\sim2.5$ hours, $\geq\sim3$ hours, $\geq\sim6$ hours, $\geq\sim9$ hours, $\geq\sim12$ hours, $\geq\sim14$ hours, $\geq\sim16$ hours, $\geq\sim18$ hours, $\geq\sim20$ hours, $\geq\sim24$ hours, $\geq\sim28$ hours, $\geq\sim32$ hours, $\geq\sim36$ hours, $\geq\sim40$ hours, $\geq\sim44$ hours, $\geq\sim48$ hours, $\geq\sim3$ days, $\geq\sim4$ days, $\geq\sim5$ days, $\geq\sim6$ days, $\geq\sim7$ days (1 week), $\geq\sim2$ weeks, $\geq\sim4$ weeks (1 month), $\geq\sim2$ months, $\geq\sim3$ months, $\geq\sim4$ months, $\geq\sim6$ months, or, e.g., $\geq\sim12$ months after mixing and the formation of an initial suspension.

Viscosity-Enhancement/Suspension Means

In this and any other ingredient aspect of the invention, the invention also can be characterized as comprising a "means" for effectively, detectably, or significantly increasing the viscosity of composition(s), increasing the durability of the suspension nature of compositions of the invention, or both. In such a respect, any known equivalents of such named agents can also be/are incorporated into compositions or methods of the invention. As with other sections similar described herein any of the components of the invention can be, where suitable, described as means (e.g., the above-described viscosity-enhancement/suspension agents/compounds or components can be described as active pharmaceutical ingredient (API) viscosity-enhancement/suspension means or means for effectively, detectably, or significantly increasing the viscosity of the composition or increasing the suspension of active pharmaceutical ingredient(s) of the composition).

Tonicity Component

In aspects, compositions provided by the invention comprise an effective amount of a pharmaceutically acceptable and ophthalmologically suitable tonicity component. In aspects, the tonicity component comprises one or more tonicity agents/constituents which detectably or significantly affect the tonicity of the composition(s).

In aspects, compositions can comprise any pharmaceutically acceptable and ophthalmologically suitable compound characterizable as a tonicity agent, such as, e.g., any compound capable of being used to adjust the composition of the formulation to a desired isotonic range.

According to aspects, one or more tonicity agents can be present in composition(s) of the invention which detectably or significantly reduce irritability or increase tolerability of the ophthalmic composition(s) over the same composition lacking such a tonicity agent or having a significantly different osmolality. In aspects, inclusion of a tonicity agent can provide a tonicity of the composition rendering a composition tolerable (e.g., lacking clinically significant irritation or damage) by a recipient/recipient eye when provided as a carrier composition or when the composition is provided as a combination composition.

Exemplary tonicity agents include, e.g., sodium chloride, glycerin, mannitol, sorbitol, other electrolytes, etc. or pharmaceutically acceptable derivatives thereof or a combination of any thereof.

In aspects, the invention provides compositions comprising a tonicity component wherein the tonicity component comprises sodium chloride, mannitol, or both sodium chloride and mannitol.

In aspects, the invention provides compositions comprising any amount of a tonicity component required to obtain a target isotonicity of a composition which renders the composition pharmaceutically acceptable and ophthalmologically suitable (e.g., does not render the composition as significantly or sufficiently irritating to a majority of users so as to deter its use).

In aspects, compositions comprise sodium chloride, wherein the sodium chloride is present in the composition in an amount of about 0.01 wt. % to about 0.04 wt. % of the composition, such as, e.g., ~0.015-~0.04 wt. %, ~0.02-~0.04 wt. %, or ~0.025-~0.04 wt. %, e.g., ~0.01-~0.035 wt. %, ~0.01-~0.03 wt. %, ~0.01-~0.025 wt. %, such as for example ~0.015-~0.035 wt. %, ~0.02-~0.03 wt. %, as in, e.g., about 0.025 wt. % of the composition.

In aspects, compositions comprise a preservative component comprising mannitol, wherein mannitol is present in the composition in an amount representing between about 0.1 wt. % to about 1 wt. % of the composition as described elsewhere, such as, e.g., between ~0.15-~0.8 wt. %, ~0.2-~0.6 wt. %, ~0.25-~0.4 wt. %, ~0.25-~0.35 wt. %, or, e.g., about 0.3 wt. % of the composition.

The tonicity agents are in the amount of about 0.01 wt. % to about 1.1 wt. % of the composition, such as, e.g., ~0.01-~1 wt. %, ~0.01-~0.8 wt. %, ~0.01-~0.6 wt. %, or ~0.01-~0.4 wt. %, e.g., ~0.05-~1.1 wt. %, ~0.1-~1.1 wt. %, ~0.15-~1.1 wt. %, ~0.2-~1.1 wt. %, ~0.25-~1.1 wt. %, ~0.3-~1.1 wt. %, such as, for example, ~0.05-~1 wt. %, ~0.1-~0.8 wt. %, ~0.15-~0.6 wt. %, ~0.2-~0.4 wt. %, e.g., ~0.3 wt. % or, e.g., ~0.325 wt. % of the composition.

Tonicity Means

In this and any other ingredient aspect of the invention, the invention also can be characterized as comprising a "means" for carrying out a stated function, here effectively establishing a target isotonicity of composition(s) of the invention. In such a respect, any known equivalents of such named agents can also be, e.g., are, incorporated into compositions or methods of the invention. As with other sections similar described herein, any of the components of the invention can be, where suitable, described as means (e.g., the above-described tonicity can be described as tonicity means or means for effectively establishing the isotonic nature of the composition).

Surfactant Component

In aspects, compositions comprise a pharmaceutically acceptable and ophthalmologically suitable surfactant component. In aspects, a surfactant component comprises one or more pharmaceutically acceptable and ophthalmologically suitable surfactant agent(s)/constituent(s). In alternative aspects, compositions provided by the invention do not comprise any component characterizable as a surfactant.

The term "surfactant" typically refers to a substance used in the ophthalmic compositions to DOS reduce surface tension of the composition(s), DOS increase surface spreading (e.g., wetting) or both. In aspects, a surfactant DOS improves dispersion of suspended particles within compositions herein over the dispersion of suspended particles in compositions lacking a surfactant. As noted, such agents are often characterized as or are closely related to agents described as solubilizers, dispersing agents, or both. Any agent exhibiting one or more of such characteristics can be present where desired/suitable.

According to aspects, one or more surfactants are present in composition(s) of the invention which detectably or significantly increase the spreading/wetting of the ophthalmic composition(s) over the same composition lacking such a surfactant or having a significantly different surface tension-related property.

In aspects, surfactant(s) of the composition(s) herein, like any other ingredient in relation to any other ingredient described here, do not detectably negatively impact any other component of the formulation, such as, e.g., they do not detectably or significantly reduce the efficacy of any one or more brinzolamide compounds, any one or more brimonidine compounds, or any other API or excipient present or which may be present in the composition.

In facets, any ophthalmologically suitable and pharmaceutically acceptable surfactant(s) are used in compositions. Exemplary surfactants(s) include, e.g., lecithin and lecithin derivatives including pure phospholipids such as, e.g., soya phosphatidyl choline) and mixed phospholipids, sodium cholate, and hydroxylated phospholipids/hydroxylated lecithin; glycerol fatty acid esters including polyglycerol fatty acid esters, polyglycerol polyricinoleate, hydrogenated castor oils and propylene glycol fatty acid esters (such as, e.g., polyoxyethyleneglycerol triricinoleate, Cremophor® EL (macrogol-1500-glyceroltriricinoleate), Cremophor® RH-40, and monobutyl glycerol); polysorbates such as polysorbate-80; sorbitan fatty acid esters including sorbitan monolaurate and sorbitan monooleate; polyoxyethylene sorbitan fatty acid esters including polyethylene glycol sorbitan monolaurate and polyethylene glycol sorbitan monooleate; etc., including propylene glycol, PEGs (e.g., PEG 200, PEG 400, PEG 3350, etc.), and cosurfactants such as alkanols (e.g., ethanol, propanol, butanol, etc.), alkane-diols (e.g., 1,2-propane diol, 1,2-butane diol, etc.), and alkane-polyols (glycerol, glucitol, polyethylene glycol, etc.), or derivatives thereof or combinations of any two or more of such compounds.

In aspects, compositions comprise one or more non-ionic surfactants. In aspects, a non-ionic surfactant can be, e.g., any ophthalmologically suitable non-ionic surfactant. In aspects, the non-ionic surfactant is, e.g., a polysorbate, a polyoxyl-ethylated castor oil (such as, e.g., Cremophor® EL, or e.g., Cremophor® RH-40), or, e.g., is a component comprising a combination thereof.

Surfactant Means

In this and any other ingredient aspect of the invention, the invention also can be characterized as comprising a "means" for providing effective, detectable, or significant surfactant activity/characteristics to composition(s) of the invention. In such a respect, any known equivalents of such named agents can also be, e.g., are, incorporated into compositions or methods of the invention. As with other sections similar described herein any of the components of the invention can be, where suitable, described as means (e.g., the above-described surfactant agents/compounds or components can be described as surfactant means or means for providing effective, detectable, or significant surfactant activity/characteristics to the composition).

Carrier Component

In aspects, compositions provided by the invention comprise an effective amount of a pharmaceutically acceptable and ophthalmologically suitable carrier component. In aspects, the carrier component comprises one or more carrying agents/constituents which serve as the carrier, also referred to in the art as the vehicle, for all constituents of the composition.

In aspects, compositions provided by the invention comprise an effective amount of a pharmaceutically acceptable and ophthalmologically suitable carrier component. In aspects, the carrier component comprises one or more carriers which provide effective delivery of the APIs and any excipient(s) as an ophthalmologically suitable composition. In aspects, a carrier is a fluid, e.g., a liquid, and, in aspects, a composition comprising a carrier is a liquid composition, such as a solution or suspension. In aspects, a carrier acts as a diluent.

In aspects any ophthalmologically suitable and pharmaceutically acceptable carrier can be used to form a composition or as a component of a composition. In aspects, exemplary carriers used in a composition described herein can comprise, e.g., a lipid carrier, a gel carrier, an oil-based carrier, an emulsion carrier, an emulsifier-containing carrier that forms an emulsion when mixed with other components, or, a solution carrier, e.g., an aqueous solution carrier. In aspects, the carrier is an aqueous carrier. In aspects, the carrier is mostly, generally only, essentially only, substantially only, or only composed of water, such as water for injection (WFI) (a sterile, solute-free preparation of distilled water). In alternative aspects, other pharmaceutically acceptable and ophthalmologically suitable aqueous carriers which do not adversely affect the stability of the composition(s) may be used, such as, e.g., deionized water.

In aspects, a carrier component is present in compositions provided by the invention in an amount representing at least about 50%, such as, e.g., ≥~55 wt. %, ≥~60 wt. %, ≥~65 wt. %, ≥~70 wt. %, ≥~75 wt. %, ≥~80 wt. %, ≥~85 wt. % ≥~90 wt. %, or, e.g., ≥~95 wt. % of the composition, such as, e.g., at least ~70 wt. %, at least ~75 wt. %, at least ~80 wt. %, at least ~85 wt. %, at least ~90 wt. %, or at least about 95 wt. % of the composition is the carrier, such as water. In aspects, ≥~70 wt. %, ≥~80 wt. %, ≥~90 wt. %, or, e.g., ≥~95 wt. % of the composition is water.

Carrier Means

In this and any other ingredient aspect of the invention, components of the invention also can be characterized as comprising a "means" for providing function(s), here effective, detectable, or significant carrier functionality for compounds of compositions, or effective, detectable, or significant carrier functionality to composition(s). In such a respect, any known equivalents of such named agents can also be, e.g., are, incorporated into compositions or methods of the invention. As with other sections similar described herein any of the components of the invention can be, where suitable, described as means (e.g., the above-described carrier agents/compounds/fluids (e.g., liquids) or components can be described as carrier means or means for providing effective, detectable, or significant carrier functionality/characteristics to the composition).

Chelation Component

In aspects, compositions provided by the invention comprise an effective amount of a pharmaceutically acceptable and ophthalmologically suitable chelation component. In aspects, the chelation component comprises one or more chelation agents/constituents which detectably or significantly affect the chelating property(ies) of the composition(s).

In aspects, compositions can comprise any pharmaceutically acceptable and ophthalmologically suitable compound characterizable as a chelating agent, such as, e.g., any compound capable of binding a detectable or significant amount of metal ion(s). In aspects, the chelating component detectably or significantly enhances preservative effectiveness by forming stable water-soluble complexes (chelates) with alkaline earth and heavy metal ions.

Exemplary suitable chelating agents include, e.g., sodium citrate, cromolyn, monomeric polyacids such as an EDTA compound, cyclohexanediamine tetraacetic acid (CDTA), hydroxyethylethylenediaminetriacetic acid (HEDTA), diethylenetriaminepentaacetic acid (DTPA), dimercaptopropane sulfonic acid (DMPS), dimercaptosuccinic acid (DMSA), aminotrimethylene phosphonic acid (ATP A); suitable and effective derivatives or analogs of any thereof, or other related compounds (as exemplified with respect to other variant compounds described above in connection with APIs) (or equivalents thereof); any ophthalmologically acceptable salts thereof, and/or combinations of any two or more such compounds. In other aspects, a chelating agent is a phosphate, such as, e.g., pyrophosphates, tripolyphosphates, and, hexametaphosphates; a chelating antibiotic such as chloroquine and tetracycline; a nitrogen-containing chelating agent containing two or more chelating nitrogen atoms within an imino group or in an aromatic ring (e.g., diimines, 2,2'-bipyridines, etc.); or for example a polyamine such as cyclam (1,4,7,11-tetraazacyclotetradecane), N—($C_1$-$C_{30}$ alkyl)-substituted cyclams (e.g., hexadecyclam, tetramethyl hexadecyl cyclam), diethylenetriamine (DETA), spermine, diethylnorspermine (DENSPM), diethylhomospermine (DEHOP), and deferoxamine (N'-[5-[[5-(acetylhydroxyamino) pentyl] amino]-1,4-dioxobutyl]hydroxy-amino]pentyl]-N'-(5-aminopentyl)-N-hydroxybutanediamide; also known as desferrioxamine B and DFO), or any pharmaceutically acceptable derivative thereof or combinations thereof.

In aspects, compositions comprise any pharmaceutically acceptable and ophthalmologically suitable amount of a chelating agent required to provide effective chelation properties to the composition. In aspects, compositions comprise a chelation component which represents about 0.001 wt. % to about 0.1 wt. % of the composition, such as, e.g., ~0.002-~0.1 wt. %, ~0.004-~0.1 wt. %, ~0.006-~0.1 wt. %, ~0.008-~0.1 wt. %, or ~0.01-~0.1 wt. %, e.g., ~0.001-~0.08 wt. %, ~0.001-~0.06 wt. %, ~0.001-~0.04 wt. %, ~0.001-~0.02 wt. %, such as, e.g., ~0.002-~0.08 wt. %, ~0.004-~0.06 wt. %, ~0.006-~0.04 wt. %, ~0.008-~0.02 wt. %, e.g., ~0.01 wt. % of the composition. In aspects, the chelation component comprises EDTA. In aspects, the chelation component comprises, generally consists of, consists essentially of, or is EDTA.

In aspects, compositions lack any component characterizable as a chelation component.

Chelation Means

In this and any other ingredient aspect of the invention, the invention also can be characterized as comprising a "means" for providing a recited function, here imparting/providing an effective, detectable, or significant chelation effect to composition(s) of the invention. In such a respect, any known equivalents of such named agents can also be, e.g., are, incorporated into compositions or methods of the invention. As with other sections similar described herein any of the components of the invention can be, where suitable, described as means (e.g., the above-described chelation agents/compounds or components can be described as chelation means or means for providing effective, detectable, or significant chelation activity/characteristics to the composition).

Buffer Component

In aspects, compositions provided by the invention comprise an effective amount of a pharmaceutically acceptable and ophthalmologically suitable buffer component. In aspects, the buffer component comprises one or more buffering agents/constituents which detectably or significantly affect the buffering capacity of the composition(s) (e.g., to maintain a pH of between about 4.0-about 7.5, e.g., between about over a storage period of at least ~1 month, ~2 months, ~3 months, ~6 months, ~9 months, ~12 months, ~14 months, ~16 months, ~18 months, ~20 months, ~22 months, ~24 months, ~28 months, ~32 months, ~36 months or longer).

In aspects, compositions can comprise any pharmaceutically acceptable and ophthalmologically suitable compound characterizable as a buffering agent.

In aspects, a buffer component of compositions is used to maintain the pH within a desirable range, such as, e.g., about 4.0-about 7.5, such as, e.g., ~4.5-~7.0, ~5.0-~7.0, or, e.g., ~6.5. Exemplary buffers include, e.g., salts of inorganic acids such as phosphate, borate, and organic acids such as citric acid monohydrate, etc. or pharmaceutically acceptable derivatives thereof or combinations thereof.

In aspects, compositions comprise a buffering component, wherein the buffering component comprises a borate compound, such as, e.g., boric acid, wherein the borate compound (boric acid) is present in the composition in an amount representing between about 0.1 wt. % to about 0.5 wt. % of the composition, such as, e.g., between ~0.1-~0.4 wt. %, or ~0.1-~0.3 wt. %, e.g., ~0.2-~0.5 wt. %, ~0.3-~0.5 wt. %, such as for example ~0.2-~0.4 wt. %, or ~0.3 wt. % of the composition. In aspects, a buffering component of a composition comprises a single borate compound. In aspects, the borate compound is boric acid.

In aspects, compositions comprise a buffer component comprising borate-polyol complex(es), wherein borate-polyol complex(es) are present in the composition in an amount representing between about 0.5 wt. % to about 6 wt. %, such as, e.g., between ~0.75-~5 wt. %, ~0.1-~5 wt. %, ~1.25-~5 wt. %, ~1.5-~5 wt. %, ~1.75-~5 wt. %, ~2-~5 wt. %, e.g., ~0.5-~5 wt. %, ~0.5-~4 wt. %, ~0.5-~3 wt. %, ~0.5-~2 wt. %, ~0.5-~1 wt. %, such as, for example, between about ~0.6-~5 wt. %, ~0.7-~4 wt. %, ~0.8-~3 wt. %, ~0.9-~2.5 wt. %, or, e.g., between about 1-about 2 wt. % of the composition.

Buffering Means

In this and any other ingredient aspect of the invention, the invention also can be characterized as comprising a "means" for providing effective, detectable, or significant buffering capacity to composition(s) of the invention. In such a respect, any known equivalents of such named agents can also be, e.g., are, incorporated into compositions or methods of the invention. As with other sections similar described herein any of the components of the invention can be, where suitable, described as means (e.g., the above-described buffering agents/compounds or components can be described as buffering means or means for providing effective, detectable, or significant buffering capacity/characteristics to the composition).

pH Adjustment Component

In aspects, compositions provided by the invention comprise an effective amount of a pharmaceutically acceptable and ophthalmologically suitable pH adjustment component. In aspects, the pH adjustment component comprises one or more pH adjusting agents/constituents which detectably or significantly affect the pH of the composition(s).

In aspects, compositions can comprise any pharmaceutically acceptable and ophthalmologically suitable compound characterizable as a pH adjusting agent, such as, e.g., any compound capable of being used to adjust the composition of the formulation to a desired pH range.

Herein, a "pH adjusting agent" is an acidifying or alkalizing agent used to significantly lower or raise the pH (potential hydrogen) of the composition to a target value. In aspects, a pH adjusting agent is an agent which, alone, is incapable of providing a buffering capacity of the composition. In aspects, a pH adjusting agent is not accompanied by a corresponding acid or base to provide a buffering capacity to the composition. In aspects, an acidifying pH adjusting agent is present to lower the pH, while an alkalizing agent is present to raise the pH to a target level. In aspects, an acidifying agent is characterizable as a strong acid. In aspects, an alkalizing agent is characterizable as a strong base. In aspects, a pH adjusting agent is added during the manufacturing process of the composition(s) to adjust the pH of the composition prior to final packaging.

In aspects, the invention provides compositions comprising any amount of a pH adjusting component required to obtain a target pH range of a composition which renders the composition pharmaceutically acceptable and ophthalmologically suitable (e.g., does not render the composition as significantly or sufficiently irritating to a majority of users so as to deter its use).

In aspects any ophthalmologically suitable and pharmaceutically acceptable pH adjusting agent is used. In aspects, exemplary pH adjusting agent(s) in a composition comprise any suitable pH adjusting agents commonly used and known in the art, such as, e.g., an acid such as a strong acid or, e.g., a base such as a strong base. In aspects, a pH adjusting agent is, e.g., a mineral acid such as sodium hydroxide hydrochloric acid (HCl) or sodium hydroxide (NaOH), such as, for example, ~1N HCl or ~1N NaOH (1N being the concentration of the agent added to the composition(s) to adjust the pH of the composition(s)).

In aspects, one or more pH adjusting agent(s) can be present in the compositions provided by the invention in an amount effective in providing the target pH. In aspects, such an amount can be considered a "trace amount," e.g., less than –0.005 w/v. %, <0.004 w/v. %, <~0.003 w/v. %, <0.002 w/v. %, e.g., <~0.001 w/v. %. In aspects, such an amount can be an amount representing between about 0-about 0.01 w/v. %. In aspects, one or more pH adjusting agent(s) can be present in the compositions provided by the invent ion in an amount effective in providing the target pH, such amounts representing between about 0-about 0.1%, such as, e.g., about 0.01%, ~0.02%, ~0.03%, ~0.04%, ~0.05%, ~0.06%, ~0.07%, ~0.08%, or, e.g., ~0.09%.

pH Adjusting Means

In this and any other ingredient aspect of the invention, the invention also can be characterized as comprising a "means" for effectively rendering composition(s) of the invention as having a pharmaceutically acceptable and ophthalmologically suitable pH. In such a respect, any known equivalents of such named agents can also be, e.g., are, incorporated into compositions or methods of the invention. As with other sections similar described herein any of the components of the invention can be, where suitable, described as means for performing function(s) (e.g., the above-described pH adjusting agents/compounds or components can be described as pH adjusting means or means for effectively establishing a suitable target pH of the composition).

Antioxidant Component

In aspects, compositions provided by the invention comprise an effective amount of a pharmaceutically acceptable and ophthalmologically suitable antioxidant component. In aspects, the antioxidant component comprises one or more antioxidant agents/constituents which provide detectable or significant antioxidant protection of one or more composition constituents, detectably or significantly improves the stability of one or more composition constituents, or detectably or significantly reduces impurities detected at time points 2 weeks, 1 month, 2 months, or 3 months after manufacturing, or any combination thereof.

In aspects, compositions can comprise any pharmaceutically acceptable and ophthalmologically suitable compound characterizable as an antioxidant. In alternative aspects, compositions provided by the invention do not comprise any component characterizable as an antioxidant.

An "antioxidant" is typically understood as referring to a substance that preferentially reacts with oxygen, thereby detectably or significantly protecting other components of a composition to which it is added from premature degradation due to oxidation (e.g., protecting APIs or other compounds known to be detectably/significantly susceptible to oxidation).

According to aspects, one or more antioxidant compounds can be present in composition(s) of the invention which detectably or significantly improve API or other constituent stability or reduce the amount of impurities, such as, e.g., providing for a composition which is stable under room temperature storage conditions, e.g., retains at least 95% of the one or more brinzolamide compounds and at least 95% of the one or more brimonidine compounds when stored at about 25° C.+/−2° C. and about 40% relative humidity or under accelerated conditions of about 40° C.+/−2° C. and about 25% relative humidity for at least about one month such as ≥~2 months or such as ≥~3 months, ≥~4 months, ≥~5 months, or, e.g., ~6 months.

For example, composition(s) provided by the invention can comprise one or more antioxidant agents which detectably improve the stability of the one or more composition constituents, reduces the amount of impurities (e.g., reduce impurity formation over periods of storage), enhances preservative effectiveness, or any or all thereof, at a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or for even longer periods (e.g., ~3-24, ~3-18, ~3-12, ~3-36, ~4-12, ~4-24, ~4-36, ~6-12, ~6-18, ~6-24, or ~6-36 months).

In aspects, the invention provides composition(s) comprising one or more pharmaceutically acceptable and ophthalmologically suitable antioxidant agents effective at pH range of between, e.g., ~4.0-~7.5, such as between ~5.0-~7.0, e.g., ~5.5-~7.0, or, e.g., ~6.0-~7.0. In aspects, antioxidant compound(s) of the composition(s) herein do not detectably or significantly negatively impact any other component of the composition, such as, e.g., they do not detectably or significantly reduce the efficacy of any one or more brinzolamide compounds, brimonidine compounds (e.g., reduce intraocular pressure reducing effect), or any other API or excipient present in the composition.

In aspects any ophthalmologically suitable and pharmaceutically acceptable antioxidant can be used in methods of the invention/incorporated in compositions of the invention, in any suitably effective amount(s). In aspects, exemplary antioxidant(s) in a composition described herein can comprise, e.g., sodium ascorbate, ascorbic acid, thiamine, pyridoxine, histidine, cysteine, glutathione, sodium bisulphite, sodium sulphite, sodium metabisulphite, sodium thiosulphite, sodium formaldehyde sulphoxylate, acetylcysteine, cysteine, thioglycerol, thioglycollic acid, thiolactic acid, thieurea, dihithreitol, propyl gallate, butylated hydroxyanisole, butylated hydroxytoluene, tertiary butyl hydroquinone, ascorbyl palmitate, nordihydroguaiaretic acid and alpha-tocopherol, any ophthalmologically acceptable salts thereof, or combinations of any two or more such compounds.

In aspects, one or more antioxidant compound(s)/agent(s) can be present in the compositions provided by the invention in an amount representing between about 0.001 w/v. %-about 2 w/v. % of the composition, such as, e.g., ~0.001 w/v. %-~1.8 w/v. %, ~0.001 w/v. %-1.6 w/v. %, ~0.001 w/v. %-~1.4 w/v. %, ~0.001 w/v. %-~1.2 w/v. %, ~0.08 w/v. %-~1 w/v. %, or. e.g., ~0.05-~1 w/v. % of the composition.

Antioxidant Means

In this and any other ingredient aspect of the invention, the invention also can be characterized as comprising a "means" for providing function(s), here such functions including effective, detectable, or significant antioxidant protection of one or more compounds of the composition(s). In such a respect, any known equivalents of such named agents can also be, e.g., are, incorporated into compositions or methods of the invention. As with other sections similar described herein any of the components of the invention can be, where suitable, described as means (e.g., the above-described antioxidant agents/compounds or components can be described as antioxidant means or means for effective, detectable, or significant antioxidant protection of one or more compounds of the composition).

Examples of Compositions

In aspects, the invention provides a composition in the form of a suspension comprising: (a) a brinzolamide compound in an amount of between about 0.1-about 10 wt. % of the composition; (b) a brimonidine compound in an amount of between about 0.01-about 0.5 wt. % of the composition; (c) boric acid in an amount of between about 0.1-about 0.5 wt. % of the composition; (d) a viscosity-enhancing component in an amount of between about 0.1-about 0.7 wt. % of the composition; (e) one or more polyols capable of forming a borate-polyol complex in an amount of between about 0.6-about 2.2 wt. % of the composition; (f) a tonicity component in an amount of between about 0.1-about 0.5 wt. % of the composition; (g) a penetration enhancer component in a total amount of between about 0.02-0.07 wt. % of the composition; and (h) a carrier.

In aspects, the invention provides a pharmaceutically acceptable and ophthalmologically suitable composition comprising: (a) a brinzolamide compound in an amount of between about 0.1 wt. %-about 10 wt. % of the composition; (b) a brimonidine compound (e.g., brimonidine tartrate) in an amount of between about 0.01 wt. %-about 0.5 wt. % of the composition; and (c) one or more borate-polyol complexes, wherein the total of the one or more borate-polyol complexes are present in an amount of between about 0.5 wt. %-about 6 wt. % of the composition; and (d) benzalkonium chloride in an amount between 0.005-about 0.02 wt. % of the composition.

Additional Means/Steps for Performing Functions

In aspects, compositions provided by the invention comprise one or more means for performing one or more specific functions and methods of the invention include steps for performing functions. In general, any element described herein as a "means" for performing a function can also, wherever suitable, serve as a "step for" performing a function in the context of methods of the invention, and vice versa. E.g., a component described herein as a means for preserving a composition also simultaneously and implicitly supports a method of making such a composition comprising a step of preserving a composition and a kit comprising a means for delivering a composition implicitly and simultaneously provides a step for delivering the composition comprising the use of such delivery means.

In one aspect, compositions provided by the invention comprise means for solubilization, such means for solubilization detectably or significantly improving the solubility of one or more composition constituents ("solubilization means"). Support for chelation means can be found in, e.g., the section entitled, "Solubilizing Component & Solubilization Means."

In one aspect, compositions provided by the invention comprise means for modifying the viscosity of the composition(s) the suspension characteristics of the composition, or both, ("viscosity-enhancement/suspension means"). Support for viscosity-enhancement/suspension means can be found in, e.g., the section entitled, "Viscosity-Enhancement/Suspension Component & Viscosity-enhancing Means."

In one aspect, compositions provided by the invention comprise means for providing a suitable tonicity of the composition(s), providing a suitable osmolality of the composition(s), e.g., means for providing composition(s) which do not cause detectable or significant ocular irritation due to tonicity when provided according to instructions ("tonicity means"). Support for tonicity means can be found in, e.g., the section entitled, "Tonicity Component."

In one aspect, compositions provided by the invention comprise means for modifying the surface tension of the compositions which in aspects provides means for increasing the spreading, e.g., the wetting, of the ophthalmic compositions ("surfactant means"). Support for surfactant means can be found in, e.g., the section entitled, "Surfactant Component."

In one aspect, compositions provided by the invention comprise means for delivering, e.g., carrying in deliverable form, constituents of the compositions ("carrier means"). Support for carrier means can be found in, e.g., the section entitled, "Carrier Component."

In one aspect, compositions provided by the invention comprise means for binding metal ions ("chelation means"). Support for chelation means can be found in, e.g., the section entitled, "Chelation Component."

In aspects, compositions provided by the invention comprise means for buffering the addition of, or buffering the presence of (if/when such compositions are placed into an environment having or compositions develop or are exposed to), elements or compositions of a different pH or which are capable of otherwise detectably or significantly modifying the pH of the compositions ("buffering means"). Exemplary buffering means are described in, e.g., the section entitled, "Buffer Component."

In one aspect, compositions provided by the invention comprise means for adjusting the pH of the composition(s), providing a suitable or target pH of the composition(s) of between about, e.g., ~4.0-~7.5, such as, e.g., ~6.0-~7.0 ("pH adjusting means"). Support for pH adjusting means can be found in, e.g., the section entitled, "pH Adjustment Component."

In one aspect, compositions comprise means for preserving the composition(s), e.g., detectably or significantly inhibit microbial growth, detectably or significantly reducing the number of impurities or detectably or significantly improving the stability of the compositions such that compositions remain safe and suitable for administration after storage of at least about 1 month, e.g., ~2 months, or e.g., ~3 months or more after manufacturing at about 25° C. and about 40% relative humidity, about 40° C. and no more than 25% relative humidity, or both for about 1-3 months or more ("preservation means"). Support for preservation means can be found in, e.g., the sections entitled, "Preservative," and "Preservative Amount."

In one aspect, compositions provided by the invention comprise means for increasing the penetration of one or more compounds of the compositions, e.g., increasing the access of one or more compounds of the composition to deeper layers or regions of ocular tissue ("penetration means"). Support for penetration means can be found in, e.g., the section entitled, "Penetration Enhancer and Penetration Enhancer Amount."

Composition Characteristics

Related Compositions/Comparisons

In aspects, compositions provided by the invention are characterizable by their comparison to one or more similar, reference products. In aspects, a reference product is the present FDA approved/US on market brinzolamide/brimonidine tartrate ophthalmic suspension sold under the trademark Simbrinza® (ALCON LABORATORIES, INC., initial US FDA approval in 2013). "Simbrinza" or "approved brinzolamide/brimonidine tartrate ophthalmic suspension" here means the pharmaceutical product approved by FDA under NDA #204251 and the trademark Simbrinza® and sold under such registered trademark in the United States prior to the submission of this disclosure, e.g., as of Oct. 1, 2014, Oct. 1, 2015, Oct. 1 2016, Oct. 1, 2017, Oct. 1, 2018, Oct. 1, 2019, or, e.g., Oct. 1, 2020, Dec. 1, 2020, Feb. 1, 2021, Apr. 1, 2021, Jun. 1, 2021, Aug. 1, 2021, or as of Oct. 1, 2021, or another product sold under the same NDA. In aspects, a reference product is the pharmaceutical product approved by FDA under NDA #204251 or a substantial similar product, such as a product that contains most, generally all, or all the same ingredients, in most, generally all, or all cases in the same amounts, or which otherwise is approved under an amendment to the NDA without the requirement of any significant new clinical trial for FDA approval.

The composition of Simbrinza/approved brinzolamide/brimonidine tartrate ophthalmic suspension is provided below in Table 2. Herein, "Simbrinza®" (e.g., reference thereto) should be interpreted as referencing a product approved by the FDA under NDA #204251 as of Apr. 19, 2013.

TABLE 2

Simbrinza ® (1% brinzolamide/0.2% brimonidine tartrate ophthalmic suspension)

| Ingredient | Amount |
|---|---|
| Brinzolamide | 1% (10 mg/mL) |
| Brimonidine tartrate | 0.2% (2 mg/mL) (equivalent to 1.32 mg as brimonidine free base) |
| Benzalkonium chloride (preservative) | 0.003% (0.03 mg) |
| Inactive Ingredients: | |
| Propylene glycol, carbomer 974P, boric acid, mannitol, sodium chloride, tyloxapol, and purified water (hydrochloric acid and/or sodium hydroxide may be added to adjust pH) | |

In one aspect, the invention provides compositions that exhibit statistically similar (or improved) ophthalmological effect(s) as a reference product according to Table A of U.S. Pat. No. 9,044,484. In one aspect, the invention provides compositions that exhibit statistically similar (or improved) ophthalmological effect(s) as a reference product according to Table A of U.S. Pat. No. 9,044,484 except with respect to the therapeutic agent(s) (e.g., with respect to the amount of brimonidine compound, e.g., brimonidine tartrate.

In one aspect, the invention provides compositions that exhibit statistically similar (or improved) ophthalmological effect(s) as a similar reference product when administered less frequently than the similar reference product. In this context, a "similar reference product" is a product that contains the same amount of active pharmaceutical ingredient(s) as the composition and ingredients that are either the same as, or that do not result in a significant difference in terms of effect as, the ingredients in the composition, except with respect to the penetration enhancer component. For example, a similar reference product can comprise a different preservative than the composition, in a different amount than the composition, but which still results in statistically similar preservation effects as the preservative component of the composition. For example, a composition can exhibit statistically similar (or better) efficacy in, e.g., reducing IOP, than a similar reference product, although the reference product is administered three times per day and the composition is only administered once a day or twice per day. In aspects, a similar reference product is Simbrinza®.

In another aspect, the invention provides compositions that exhibit statistically similar (or improved) ophthalmological effect(s) as a similar reference product when administered less frequently than a substantially identical reference product. A "substantially identical" reference product has the same amount of API(s) and the same amount and type of every other excipient in the composition, other than in respect of the penetration enhancer component. In aspects, a substantially identical reference product is Simbrinza®.

In aspects, a composition provided by the invention which is similar (as described in the preceding paragraph) to a reference product, e.g., an FDA approved reference product, e.g., Simbrinza®, demonstrates bioequivalence to such a product, e.g., as determined by an appropriately conducted clinical endpoint study as required/recommended by the US FDA as a test to prove or support bioequivalence. In aspects, a composition provided by the invention which is similar to a reference product, e.g., an FDA approved reference product, e.g., Simbrinza® has a bioavailability of brinzolamide compound(s) and brimonidine compound(s) which is equivalent to or greater than that of the brinzolamide and brimonidine compounds in such a product. In aspects, a composition provided by the invention which is similar to a reference product, e.g., an FDA approved reference product, e.g., Simbrinza® demonstrates at least 1, such as 2, 3, or more pharmacokinetic performance characteristics of brinzolamide, brimonidine, or both, which is equivalent to or detectably or significantly better than, that of the brinzolamide compound, brimonidine compound, or both in such a product.

In aspects, a composition provided by the invention which is substantially identical to a reference product, e.g., an FDA approved reference product, e.g., Simbrinza® has a bioavailability of brinzolamide compound(s) and brimonidine compound(s) which is equivalent to or greater than that of the brinzolamide and brimonidine compounds in such a product. In aspects, a composition provided by the invention which is substantially identical to a reference product, e.g., an FDA approved reference product, e.g., Simbrinza® demonstrates at least 1, such as 2, 3, or more pharmacokinetic performance characteristics of brinzolamide, brimonidine, or both, which is equivalent to or detectably or significantly better than, that of the brinzolamide compound, brimonidine compound, or both in such products.

pK Parameters

In aspects, the invention provides compositions which are characterizable in relation to standard reference product(s). In aspects, the invention provides compositions which are characterizable in reference to the United States Food and Drug Administration (FDA) approved product Simbrinza® (see Table 2).

In aspects, compositions herein demonstrate bioequivalence with Simbrinza® when used to treat the same condition for the same period of time when administered as one drop twice per day to an effected eye.

In aspects, compositions herein demonstrate bioequivalence with Simbrinza® when used to treat the same condition for the same period of time when administered as one drop once per day to an affected eye.

Stated alternatively, compositions herein demonstrate bioequivalence with Simbrinza® when used to treat the same condition for the same period of time when administered in a dose which less than 67% of, e.g., <65%, <60%, <55%, <50%, <45%, <40%, or <35%, such as, e.g., as much as about 33% of, that of Simbrinza®.

Here, uncontradicted, the term "bioequivalence" is interpreted in the manner the term is used by US FDA, typically meaning the absence of a significant difference in the rate and extent to which the active ingredient or active moiety in pharmaceutical equivalents or pharmaceutical alternatives becomes available at the site of drug action when administered at the same molar dose under similar conditions in an appropriately designed study.

In aspects, bioequivalence of compositions provided by the invention with Simbrinza® is established by the performance of at least one clinical endpoint study. In aspects, the at least one clinical endpoint study is any clinical endpoint study approved by the FDA suitable and sufficient for demonstrating bioequivalence of a topically applied ophthalmic suspension comprising brinzolamide and brimonidine tartrate. In aspects, bioequivalence with Simbrinza® is established according to US FDA guidance for the establishment of bioequivalent ophthalmic compositions (see (a)

"Draft Guidance on Brinzolamide", Recommended April 2014; Revised December 2014, March 2015, May 2019, published by the US Food and Drug Administration, and (b) "Draft Guidance on Brimonidine Tartrate; Brinzolamide", Recommended December 2014; Revised March 2015, May 2019, published by the US Food and Drug Administration).

In aspects, compositions herein are tested (e.g., evaluated or assessed) in a randomized (1:1), double-masked, parallel, two-arm, in-vivo bioequivalence study with defined clinical endpoint(s) to establish bioequivalence with Simbrinza®. In aspects, the bioequivalence study is performed on male and female subjects diagnosed with chronic open angle glaucoma or ocular hypertension in both eyes (a "clinical endpoint study").

In aspects, a clinical endpoint study performed to demonstrate bioequivalence of compositions of the invention with Simbrinza® comprise the administration of test compositions and Simbrinza(a) wherein the reference formulation is applied as one drop in both eyes three times daily, and the test compositions are applied as one drop in both eyes two times or one time daily (e.g., a study demonstrating bioequivalence of compositions with a twice-daily administration protocol and a study demonstrating bioequivalence of compositions with a once-daily administration protocol, or a study demonstrating both). In aspects, time points comprise time points selected from, e.g., approximately 8:00 AM, 4:00 PM, and 10:00 PM for 42 days (6 weeks). In aspects such time points may be different. In aspects, time points are established in conjunction with FDA guidance. In aspects, a clinical endpoint study performed to demonstrate bioequivalence of compositions of the invention with Simbrinza® comprise the administration of test compositions as one drop in both eyes twice daily while the reference formulation Simbrinza® is administered three times daily. In aspects, a clinical endpoint study performed to demonstrate bioequivalence of compositions of the invention with Simbrinza® comprise the administration of test compositions as one drop in both eyes once daily while the reference formulation Simbrinza® is administered three times daily. In aspects, a clinical endpoint study is a clinical endpoint study performed substantially in accordance with FDA guidance. In aspects, a clinical endpoint study is a clinical endpoint study performed substantially in accordance with FDA guidance wherein the clinical endpoint study varies from FDA guidance with respect to the number of administrations (dosing frequency) of the test composition, the times at which such doses are administered, or both.

In aspects, compositions of the invention demonstrate a mean difference in intraocular pressure measured in both eyes between the two treatment groups at four time points of a clinical endpoint study. In aspects, the four time points are, e.g., approximately 8:00 AM (hour 0, prior to a morning administration of a single drop of composition) and 10:00 AM (hour 2) at day 14 and day 42 post-administration.

In aspects, compositions provided by the invention have limits of each two-sided 95% confidence interval of the treatment difference (test-reference) for mean intraocular pressure (IOP) of both eyes (continuous variable), at all four follow-up points (e.g., at approximately 8:00 AM (hour 0, prior to morning administration) and 10:00 AM (hour 2) at day 14 (week 2) and day 42 (week 6), which is ±1.5 mmHg using the per-protocol (PP) population for the majority of time points measured. In aspects, compositions demonstrate limits of each two-sided 95% confidence interval of the treatment difference (test-reference) for mean IOP of both eyes at all four follow-up points which is ±~1.5 mmHg, ±~1.4 mmHg, ±~1.3 mmHg, ±~1.2 mmHg, ±~1.1 mmHg, ±~1 mmHg, ±~0.9 mmHg, ±~0.8 mmHg, ±~0.7 mmHg, ±~0.6 mmHg, ±~0.5 mmHg, ±~0.4 mmHg, ±~0.3 mmHg, ±~0.2 mmHg, or, e.g., ±~0.1 mmHg. In aspects, such results are obtained when compositions provided by the invention are administered twice per day compared to the administration of Simbrinza® three times per day. In aspects, such results are obtained when compositions provided by the invention are administered once per day compared to the administration of Simbrinza® three times per day.

In aspects, compositions provided by the invention provide bioequivalent or detectably or significantly improved pharmacokinetic properties when administered one time or two times per 24-hour period compared to the same one or more pharmacokinetic properties of a composition comprising the same amount of brinzolamide and the same amount of brimonidine administered three times per 24-hour period. In aspects, such a reference product is Simbrinza®. In aspects, such a reference product has a detectably or significantly lower amount of a penetration enhancement component. In aspects, such a reference product has a detectably or significantly lower amount of benzalkonium chloride. In aspects, such a reference product has an amount of benzalkonium chloride which is, e.g., as low as about 1.5% of that of the compositions provided by the invention. In aspects, such a reference product has an amount of benzalkonium chloride which is about 60% of that of the compositions provided by the invention. In aspects, such a reference product has an amount of benzalkonium chloride which is, e.g., between about 1.5%-about 60% of that of the compositions provided by the invention, such as, e.g., ~1.5-~55%, or ~1.5-~50%, or ~1.5-~45%, e.g., 5%-~60%, 10%-~60%, 15%-~60%, 20%-~60%, 25%-~60%, 30%-~60%, 35%-~60%, or 40%-~60%, such as ~5-~55%, ~10-~50%, ~20-~45%, ~30-~45%, ~35-~45%, or, e.g., between about 40-~45% of that of the compositions provided by the invention, such as, e.g., ~42-43% of that of the compositions provided by the invention.

In aspects, the invention provides compositions which demonstrate equivalent or detectably or significantly improved bioavailability when administered as one drop twice per day over the bioavailability of a composition comprising the same amount of brinzolamide and the same amount of brimonidine when administered as one drop three times per day.

In aspects, the invention provides compositions which demonstrate equivalent or detectably or significantly improved bioavailability when administered as one drop once per day over the bioavailability of a composition comprising the same amount of brinzolamide and the same amount of brimonidine when administered as one drop three times per day.

In aspects, the invention provides compositions which demonstrate one or more equivalent or detectably or significantly improved pharmacokinetic property(ies) when administered as one drop twice per day over the bioavailability of a composition comprising the same amount of brinzolamide and the same amount of brimonidine when administered as one drop three times per day.

In aspects, the invention provides compositions which demonstrate one or more equivalent or detectably or significantly improved pharmacokinetic property(ies) when administered as one drop once per day over the bioavailability of a composition comprising the same amount of brinzolamide and the same amount of brimonidine when administered as one drop three times per day.

In aspects, the invention provides compositions which demonstrate equivalent or detectably or significantly improved bioavailability when administered as one drop once per day over the bioavailability of a composition comprising the same amount of brinzolamide and the same amount of brimonidine when administered as one drop three times per day, with fewer adverse events than a reference product containing 0.003% of benzalkonium chloride.

In any of the above-described aspects, the product compared to the composition can be a similar product or substantially identical product, as described elsewhere (e.g., in the latter case a product that is identical in most, generally all, or all respects in terms of ingredients except for in terms of the penetration enhancer component of the composition).

In aspects, the invention provides compositions which, when administered no more than twice, such as two times or once, per 24-hour period (per day or daily) which demonstrate a bioequivalent effect to that of a reference product. In aspects, the reference product is a product comprising the same amount of a brinzolamide compound and the same amount of a brimonidine compound. In aspects, a reference product is an FDA approved reference product, such as, e.g., Simbrinza®. In aspects, a bioequivalent effect is an effect which would lead the governing body, such as, e.g., would lead the FDA, to conclude that the two compositions are bioequivalent or, e.g., that the two compositions exhibit significantly similar clinical results in a clinical study. In aspects, such a clinical study is a study performed in accordance with FDA guidance.

In one aspect, the invention provides compositions comprising a pharmaceutically acceptable and ophthalmologically suitable composition comprising a pharmaceutically acceptable and ophthalmologically suitable brinzolamide compound in an amount of about 0.1 wt. %-about 10 wt. % of the composition; and a pharmaceutically acceptable and ophthalmologically suitable brimonidine compound in an amount of about 0.01 wt. %-about 0.5 wt. % of the composition, wherein an effective daily dose of the composition is bioequivalent to a daily dose of a similar or substantially identical reference composition/product that comprises about 125%-500%, such as about 133%-400%, e.g., about 150%-350% of about 200% to about 300% of the amount of the brinzolamide compound(s) in the composition, the brimonidine compound(s) in the composition, or both (e.g., about 200% to about 300% of the amount of the brimonidine compound in the composition). Bioequivalence in this context can be determined by methods described elsewhere herein, e.g., performance of an FDA approved study or a study that is suitable for submission to FDA in connection with obtaining regulatory approval for the lower daily dose composition. In aspects, the reference product differs from the composition in terms of amount of penetration enhancer (s), presence of polyol:borate complexes, or both. In aspects, the daily dose of the composition is an amount that is effective for once-a-day administration. In aspects, the daily dose of the composition is an amount that is effective for twice-daily administration. In aspects, a reference product must be administered to subject(s) at least 1.5× as many times, such as must be administered 2× as many times, 3× as many times, or more than 3× as many times (e.g., 4× as many times) as the composition in order to deliver a bioequivalent effect or an effective daily dose of the active ingredients contained therein.

pH

In aspects, compositions of the invention have a pH of about 4 to about 7.5, such as, e.g., ~4-~7.4, ~4-~7.3, ~4-~7.2, ~4-~7.1, ~4-~7, ~4-~6.9, ~4-~6.8, ~4-~6.7, ~4-~6.6, or ~4-~6.5, e.g., ~4.2-~7.5, ~4.4-~7.5, ~4.6-~7.5, ~4.8-~7.5, ~5-~7.5, ~5.2-~7.5, ~5.4-~7.5, ~5.6-~7.5, ~58-~7.5, ~6-~7.5, ~6.2-~7.5, or ~6.4-~7.5, such as, e.g., ~4.5-~7, or ~5-~6.5.

Osmolality

In aspects, compositions of the invention have an osmolality of about 200 to about 450 mOsm/kg, such as, e.g., ~225-450 mOsm/kg, ~250-450 mOsm/kg, ~275-450 mOsm/kg, ~300-450 mOsm/kg, ~325-450 mOsm/kg, ~350-450 mOsm/kg, ~375-450 mOsm/kg, ~400-450 mOsm/kg, or ~425-450 mOsm/kg, e.g., ~200-~425 mOsm/kg, ~200-~400 mOsm/kg, ~200-~375 mOsm/kg, ~200-~350 mOsm/kg, ~200-~325 mOsm/kg, ~200-~300 mOsm/kg, ~200-~275 mOsm/kg, ~200-~250 mOsm/kg, or ~200-~225 mOsm/kg, such as, e.g., ~225-~425, ~250-~400, or ~275-~375 mOsm/kg.

In aspects, compositions have an osmolality which is suitable for topical administration to a mammalian eye which does not cause significant irritation the majority of patients as determined by an appropriately conducted and controlled clinical trial.

Stability

Compositions of the invention can be, in aspects, characterized on the basis of physical stability, chemical stability, or both.

In aspects, compositions exhibit sufficient physical and chemical integrity to maintain at least ~95%, ~96%, ~97%, or at least ~98% of the amount of any included API(s) and to maintain total impurities below 0.5% (e.g., below pharmaceutically acceptable level) to allow storage at a convenient temperature, such as between about 2° C. and about 50° C., for a commercially reasonable period of time, such as, e.g., at least about 1 month, such as at least about 2 months, or at least about 3 months or more, e.g. typically for at least about 4, ~5, ~6, ~7, ~8, ~9, ~10, ~11, ~12, ~18, ~24, ~30, or, e.g., ~36 months, when stored in its original packaging.

The term "physical stability" typically refers to maintenance of color, dissolved oxygen level, head space oxygen level, particulate matter, etc. Relevant to suspensions, physical stability can refer to no detectable or significant increase in coagulation, flocculation, caking, clumping, etc. In aspects, physical stability for suspensions means no detectable or significant flocculation, coagulation, or clumping, etc., or at least no sustained flocculation, coagulation, clumping, etc. (e.g., flocculation, coagulation, clumping, etc., that is not reduced to below visual detection levels upon routine agitation such as about 0.5-5, 0.3-3, 0.25-2, 0.25-1.5, 0.25-1, 0.5-1, or 0.25-2.5 minutes of manual shaking).

The term "chemical stability" typically refers to formation of drug-related impurities in terms of total impurity, single maximum individual impurity, and maximum individual unknown impurity, or to the reduction in API due to undesired reactions. For the purpose of the compositions provided by the invention described here. In aspects, chemical stability also includes maintenance of pH of the finished formulation.

The terms "impurity" or "impurities" refer to undesired substance(s) in a composition which may be present in a composition immediately following manufacturing (e.g., at initial quality control testing composition following manufacturing, prior to storage) or which may be formed after a certain period of shelf life of a composition. Impurities may be formed via degradation of one or more components of the composition. Sources of degradation can include, e.g., oxidation, light, ultraviolet light, moisture, heat, changes in pH, and composition component interactions.

In aspects, compositions provided by the invention are stable compositions such that CAI compounds of the composition, alpha-2-adrenergic agonist compounds of the composition, or both CAI and alpha-2-adrenergic agonist compounds of the composition (e.g., brinzolamide and brimonidine tartrate) are present in an amount of at least 98%, such as ≥~98.2%, ≥~98.4%, ≥~98.6%, ≥~98.8%, ≥~99%, ≥~99.2%, ≥~99.4%, ≥~99.6%, ≥~99.8%, or even ~100% for a period of at least about 1 month (e.g., ~2, ~3, ~4, ~5, ~6 months or more such as ≥12, ≥18, or ≥24 months) when stored at relevant conditions, such as, e.g., at about 25° C. and about 40% relative humidity, at about 40° C. and not more than 25% relative humidity, or both for 3 months.

In aspects, compositions provided by the invention are capable of maintaining a level of total impurities of less than about 0.5%, such as less than ~0.4%, <~0.3%, <~0.2%, or, e.g., <0.1% or less than that quantifiable by the limits of detection of impurity detection equipment used in such an analysis, for a period of at least about 1 month or, e.g., ≥~2 months, ≥~3, ≥~4, ≥~5, or ≥~6 months or more when stored at relevant conditions, such as FDA stability testing conditions, such as, e.g., at about 25° C. and about 40% relative humidity, at about 40° C. and not more than 25% relative humidity, or both for 3 months.

In aspects, compositions herein retain at least about 85 w/w. % of the potency of CAI compound(s) of the composition, alpha-2-adrenergic agonist compound(s) of the composition, or both CAI and alpha-2-adrenergic agonist compounds of the composition (e.g., brinzolamide and brimonidine tartrate), or other incorporated API of the composition, or all thereof, e.g., ≥~86 w/w. %, ≥~87 w/w. %, ≥~88 w/w. %, ≥~89 w/w. %, ≥~90 w/w. %, ≥~91 w/w. %, ≥~92 w/w. %, ≥~93 w/w. %, ≥~94 w/w. %, ≥~95 w/w. %, ≥~96 w/w. %, ≥~97 w/w. %, ≥~98 w/w. %, ≥~99 w/w. %, or even, e.g., 100 w/w. % of the activity of any API for at least about 1 month, such as, e.g., ≥~6 weeks, ≥~2 months, ≥~10 weeks, ≥~3 months, ≥~4 months, ≥~5 months, ≥~6 months, ≥~7 months, ≥~8 months, ≥~9 months, ≥~10 months, ≥~1 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months or more (under relevant conditions, such as those described above or elsewhere herein).

In aspects, the invention provides compositions comprising about 01 to about 10 wt. % of a brinzolamide compound, about 0.01 to about 0.5 wt. % of brimonidine tartrate and about 0.005-about 0.02 wt. % of benzalkonium chloride, wherein the composition comprises a detectably or significantly greater stability (as measured by a standard FDA stability testing protocol) of the brimonidine compound, the brinzolamide compound, or both the brimonidine compound and the brinzolamide compound than that of an FDA approved reference product composition comprising the same amount of brimonidine compound, the same amount of brinzolamide compound, and 0.003 wt. % of benzalkonium chloride.

In aspects, such compositions provide a detectably or significantly longer shelf life than that of an FDA approved reference product composition comprising the same amount of brinzolamide compound, the same amount of brimonidine compound, and 0.003 wt. % of benzalkonium chloride. In aspects, such a shelf life is, e.g., at least about 1%, ≥2%, ≥3%, ≥5%, ≥10%, ≥15%, or, e.g., ≥20% percent longer than that of the FDA approved reference product (e.g., Simbrinza®).

In aspects, the invention provides compositions comprising about 01 to about 10 wt. % of a brinzolamide compound, about 0.01 to about 0.5 wt. % of brimonidine tartrate and about 0.005-about 0.02 wt. % of benzalkonium chloride, wherein the composition comprises a detectably or significantly greater stability (as measured by a standard FDA stability testing protocol) of the brimonidine compound, the brinzolamide compound, or both the brimonidine compound and the brinzolamide compound than that of the same composition lacking a borate-polyol complex.

In aspects, such compositions provide a detectably or significantly longer shelf life than that of an FDA approved reference product composition comprising the same amount of brinzolamide compound, the same amount of brimonidine compound, and 0.003 wt. % of benzalkonium chloride. In aspects, such a shelf life is, e.g., at least about 1%, ≥2%, ≥3%, ≥5%, ≥10%, ≥15%, or, e.g., ≥20% percent longer than that of the same composition lacking a borate-polyol complex.

Here, the term "shelf life" refers to the amount of time the composition is stored without loss of potency and/or loss of a suitable dissolution profile, such as, e.g., loss of suitable suspension of any suspended API. In aspects, shelf life refers to the amount of time the compositions effectively maintain brinzolamide in suspension, such that the consistency of the composition is at least generally, substantially, or effectively uniform, e.g., at least about 90%, e.g., ≥~91%, ≥~92%, ≥~93%, ≥~94%, ≥~95%, ≥~96%, ≥~97%, ≥~98%, ≥~99%, or, e.g., even about 100% of the composition has a relative ratio of any single component to any other single component of no more than 1.1:1, such as no more than ~~1.09:1, 1.08:1, 1.07:1, 1.06:1, 1.05:1, 1.04:1, 1.03:1, 1.02:1, 1.01:1 or, e.g., about 1:1. In aspects, shelf life refers to a period of time wherein neither the carbonic anhydrase inhibitor compounds nor the alpha-2-adrenergic compounds of the composition lose more than about 10%, such as, e.g., ≤~9%, ≤~8%, ≤~7%, ≤~6%, ≤~5%, ≤~4%, ≤~3%, ≤~2%, or, e.g., ≤~1%, of their potency while in storage after manufacturing and prior to use.

In aspects, compositions provided by the invention provide a shelf life of at least about 3 months, such as, e.g., ≥~4 months, ≥~6 months, ≥~8 months, ≥~10 months, ≥~12 months, ≥~16 months, ≥~20 months, ≥~24 months, ≥~30 months, ≥~36 months, ≥~42 months, or ≥~48 months, when stored under standard home/user storage conditions (e.g., at about room temperature (20 30° C.) and 30-70% relative humidity).

Particle Size

In aspects, compositions provided by the invention comprise particles in suspension. In aspects, the particles in suspension have an average diameter in any direction of less than 5 µm, such as, e.g., <~4.5 µm, <~4 µm, <~3.5 µm, <~3 µm, <~2.5 µm, <~2 µm, <~1.5 µm, <~1 µm, or even less, such as <~0.5 µm, e.g., between about 0.5 µm-about 3 µm, as in between ~0.5-~2.5 µm, ~0.5-~2 µm, ~1.5-~2.5 µm, or ~0.5-~1 µm, such as, e.g., ~1-~3 µm, ~0.5-~1.5 µm, or, e.g., ~2-~2.5 µm. In aspects, compositions are designed for delivery as drops (e.g., via standard eye-drop administration methods known in the art) and comprise a particle size of less than about 5 µm, such as, e.g., <~4.5 µm, <~4 µm, <~3.5 µm, <~3 µm, <~2.5 µm, or, e.g., <~2 µm, such as between about 2-about 3 µm. In aspects, particles in suspension comprise brinzolamide.

In aspects, compositions comprising particles with an average size less than 5 µm, mostly comprising particles of less than 5 µm perform detectably or significantly better in terms of maintaining uniform size and/or shape characteristics, e.g., in the case of relatively uniform sized and sufficiently small particle compositions, over periods of time, such as those described elsewhere (e.g., >1 month, >2 months, >3 months, >6 months, >1 year, >18 months, or >2 years when maintained under typical FDA stability testing conditions, as described elsewhere or known in the art). In aspects, particles can be defined by an absolute, typical, or average size or shape.

In one aspect, the particle size of particles in suspension in compositions herein cannot detectably or significantly block trabecular meshwork of the eye, e.g., cannot detectably or significantly restrict flow of aqueous humor out of the eye. That is, in aspects, particle size of particles, and particle size of any two or more agglomerated particles, is sufficiently small so as to allow at least about 80%, >~82%, >~84%, >~86%, >~88%, >~90%, >~90%, >~92%, >~94%, >~96%, >~98%, >~99%, >~99.5%, >~99.75%, or, e.g., ~100% of unrestricted aqueous humor flow through the trabecular meshwork of the eye.

As stated elsewhere herein, in aspects, most, generally all, substantially all, or all agglomeration of particles, e.g., any flocculation of particles, is resolved by shaking the compositions for a minimum of about 10 seconds, such as, e.g., at least about ~12 seconds, ~14 seconds, ~16 seconds, ~18 seconds, ~20 seconds, ~22 seconds, ~24 seconds, ~26 seconds, ~28 seconds, ~30 seconds, such as, e.g., at least about ~35 seconds, ~40 seconds, ~45 seconds, ~50 seconds, ~55 seconds, or, e.g., ~60 seconds. In aspects, most, generally all, substantially all, or all flocculation is resolved by shaking for less than about 60 seconds, such as by shaking for <~55 seconds, <~50 seconds, <~45 seconds, <~40 seconds, <~35 seconds, <~30 seconds, <~25 seconds, <~20 seconds, <~15 seconds, <~10 seconds, or, e.g., by shaking for less than about 5 seconds. In aspects, shaking for such period(s) of time results in less than about 40%, <~35%, <~30%, <~25%, <~20%, <~15%, <~10%, or, e.g., <~5% of the particles of the composition being flocculated, or, e.g., results in no detectably or significant particle flocculation.

In one aspect, particles of composition(s) herein can be characterized as being mostly, generally, or substantially uniform in size, shape, or both, for example having mostly, generally, or substantially the same maximum diameter in any single direction, or for example being mostly, generally, or substantially spherical or other shape.

Average Diameter or Maximum Dimension Size of Particles

One possible way to characterize compositions of the invention is the average maximum size of the particles in any one dimension or the maximum average diameter in the case of particles that are spheroid or spherical in shape. It is to be understood that these concepts can be interchanged herein such that the description of any aspect with respect to a maximum average diameter, as applied to a spheroid particle for example, is to be understood as providing corresponding support for a non-spheroid particle having an average maximum size in any one dimension of a corresponding size.

In one aspect, at least about 50%, at least about 70%, at least about 80%, at least about 90%, at least about 95%, at least about 99%, or about 100% of the particles in the composition have a maximum diameter (or average maximum dimension) of less than about 5 μm, such as, e.g., ≤~4.5 μm, ≤~4 μm, ≤~3.5 μm, ≤~3 μm, ≤~2.5 μm, ≤~2 μm, ≤~1.5 μm, ≤~1 μm, or, e.g., even ≤~0.5 μm. In one aspect, the size of at least about 75%, at least about 85%, at least about 92.5%, or at least about 97.5% of the particles of the composition, or more, such as about 100% of the particles of the composition, are between about 0.5-about 1.5 μm in compositions provided by injection and between about 2-about 3 μm in compositions provided by drops.

Size Distribution of Particles and Methods of Production

Compositions of the invention also can be characterized on the basis of the size distribution of particles in the composition. In this respect it is worth noting that many compositions of the invention will comprise particles that vary in size due to differences that arise in the manufacturing process, handling, or for similar reasons. In aspects, compositions with relatively uniform sizes can offer advantageous properties including in aiding in injectability of the composition, aiding in the suspension characteristics of the compositions, etc.

In aspects, particles of the compositions provided by the invention are relatively uniform in size. The relative uniformity in particle size of the suspended particles of the compositions herein can be characterized by describing the coefficient of variation in particle size in the composition. E.g., in aspects, the maximum particle diameter coefficient of variation (CV) of particles of the composition is less than about 75%, <~70%, <~65%, <~60%, <~55%, <~50%, <~45%, <~40%, <~35%, <~30%, <~25%, <~20%, <~15%, <~12.5%, <~10%, or less than about 7.5%, e.g., <~7%, <~6%, or <~5%.

In aspects, particles of the compositions described herein can have a size distribution such that ≥~20%, such as ≥~22%, ≥~24%, ≥~26%, ≥~28%, ≥~30%, ≥~32%, ~34%, ≥~36%, ≥~38%, ≥~40%, ≥~42%, ≥~44%, ≥~46% ≥~48% or ≥~50%, such as ≥~52%, ≥~54%, ≥~56%, ≥~58%, ≥~60%, ≥~62%, ≥~64%, ≥66%, ≥~68%, ≥~70%, ≥~72%, ≥~74%, ≥~76%, ≥~78%, or ≥~80% of the particles of the composition have a maximum particle diameter that is within about 75%, ~70%, ~65%, ~60%, ~65%, ~50%, ~48%, ~46%, ~44%, ~42%, ~40%, ~38%, ~36%, ~34%, ~32%, ~30%, ~28%, ~26%, ~24%, ~22%, ~20%, ~18%, ~16%, ~14%, ~12%, or, e.g., within ~10% of the average particle diameter of the particles in the composition. According to specific embodiments, at least about 65% of the particles of the composition have a maximum particle diameter that is within 35% of the average particle diameter of the particles in the composition. According to alternative specific embodiments, at least about 70% of the particles of the composition have a maximum particle diameter that is within about 33% of the average particle diameter of the particles in the composition. According to yet further embodiments, at least 33% of the particles have a maximum diameter that is within about 15% of the average particle diameter of particles in the composition. In yet another embodiment, at least about 40% of the particles have a maximum diameter that is within about 20% of the average particle diameter of the particles in the composition.

According to certain embodiments, less than about 50%, such as, <~40%, <~30%, <~20%, <~10%, or, e.g., <~5% of the particles of compositions herein have an average maximum dimension/diameter that is above 5 μm. According to certain embodiments, less than about 50%, such as, <~40%, <~30%, <~20%, <~10%, or, e.g., <~5% of the particles of compositions herein have an average maximum dimension/diameter that is below 0.1 μm. According to certain embodiments, compositions designed for injection comprise less than about 50%, such as, <~40%, <~30%, <~20%, <~10%, or, e.g., <~5% of the particles having have an average maximum dimension/diameter that is above 2 μm or below 0.1 μm. According to certain embodiments, compositions designed for administration by drops comprise less than about 50%, such as, <~40%, <~30%, <~20%, <~10%, or, e.g., <~5% of the particles having have an average maximum dimension/diameter that is above 4 µm or below 1 µm.

In some aspects, the particles of the inventive compositions can alternatively be described by their size relative to one another. According to certain embodiments, the particles in suspension within compositions herein have an average maximum diameter which is less than about 5 µm and greater than about 0.1 µm, and at least about 85%, ≥~90%, ≥~95%, or more (e.g., ≥~97.5% or >~99%) of the particles in suspension have an average maximum diameter that is within about 75%, ~80%, ~85%, ~90%, or within about ~95% or more of the average maximum diameter of at least about 75%, ~80%, ~85%, ~90%, or ~95% or more of the other particles in suspension.

In aspects, suspended particles of the compositions provided herein can also or alternatively be characterizable based on the shape of some, most, largely all, substantially all, or all of the particles in the composition. In aspects, particles of the invention can have any suitable shape. For example, the particles can have a "pollen" shape, a squircle shape, a disc shape, or other shape. In a typical aspect the particles have a relatively spherical or spheroid shape. The uniformity of shape of particles can be determined by comparison of the dimensions of the particles. In one aspect, the composition materially comprises, predominately comprises, largely consists of, substantially consists of, consists essentially of, or consists of particles having a relatively similar proportion in most dimensions, in at least 65% of dimensions, at least 75% of dimensions, at least 90% of dimensions, or in all dimensions. Dimensions in this respect means dimensions in all planes of the particles' three-dimensional shapes. E.g., at least about 50%, at least about 70%, at least about 85%, at least about 95%, or at least about 100% of the particles in aspects can be characterizable as having the same shape.

In aspects, particles will also have the same size, such that the proportions described above can be 1:1 or about 1:1. For example, where most, largely all, nearly all, or all of the particles in the composition are spherical/spheroid less than about 10% of particles can typically have a maximum diameter that is more than 40% greater than the average diameter of particles in the composition or less than about 40% of the average diameter of particles in the composition. For example, <~10%, <~9%, <~8%, <~7%, <~6%, <~5%, <~4%, <~3%, <~2%, or <~1%, such as <~0.9%, <~0.8%, <~0.7%, <~0.6%, <~0.5%, <~0.4%, <~0.3%, <~0.2%, <~0.1%, <~0.05%, or less than about 0.01% of particles have a maximum diameter that is more than about 40%, such as more about 42%, >~44%, >~46%, >~48%, >~50%, >~52%, >~54%, >~56%, >~58%, or >~60%, for example >~62%, >~64%, >~66%, >~68%, >~70%, >~72%, >~74%, >~76%, >~78%, >~80%, >~82%, >~84%, >~86%, >~88%, or more than about 90%, for example >~92%, >~94%, >~96%, >~98%, or more than approximately 99% larger or smaller than the average diameter of particles in the composition. According to one embodiment, less than 1% of particles have a maximum diameter that is more than 66% greater than the average diameter of particles in the composition or less than about 66% of the average diameter of particles in the composition. According to one embodiment, less than about 10% of the particles have a maximum diameter more than 50% greater or less than about 50% less than the average diameter of particles in the composition.

In one exemplary aspect, the invention provides compositions in which the diameter of at least about 80% of the particles of the composition can vary by no more than about 5% in any direction. That is, for example, >~80%, for example >~82%, >~84%, >~86%, >~88%, or for example >~90%, >~92%, >~94%, >~94%, >~96%, >~98%, >~99% or at least approximately 99.5% of the particles of the present invention vary by no more than about 15%, for example vary by <~14%, <~13%, <~12%, <~11%, <~10%, <~9%, <~8%, <~7%, <~6%, <~5%, <~4%, or even less, for example <~3%, <~2% or vary by no more than 1% in any direction, conferring a mostly spherical shape to the particles. According to specific embodiments, at least about 80% of the particles of the composition vary by no more than 15% in any direction. According to more specific embodiments, at least about 90% of the particles of the composition vary by no more than about 5% in any direction. According to one embodiment, at least about 80% of the particles of the composition vary by no more than about 2% in any direction, and according to yet further specific embodiments, at least about 85% of the particles of the present invention vary by no more than about 1% in any direction.

In another aspect, the invention provides particles wherein the diameter (or average maximum dimension, average dimension, and/or average minimum dimension) of at least 80% of the particles of the composition (e.g., at least about 90% of the particles or at least about 95% of the particles) varies by no more than 15% in any direction. In more particular aspects at least about 85%, at least about 85%, or at least about 99% of the particles have diameters that vary by 5% or less with respect to the average diameter of the particles in the composition. In still more precise aspects, at least about 50%, at least about 60%, at least about 70%, at least about 85%, or at least about 95% of the particles can have diameters that are within about 2% of the average particle diameter or even within ~1% of the average particle diameter.

Administered Form & Dosing

Compositions provided by the invention can be provided in any form which is suitable for topical ophthalmic administration to a mammalian eye. In aspects, compositions are provided in the form of a suspension, dispersion, or solution.

In aspects, compositions provided by the invention are characterizable as suspensions. In aspects, a suitable suspension is a suspension which at least significantly increases the particle suspension of one or more active pharmaceutical ingredients (e.g., a brinzolamide compound), such that most, generally all, substantially all, or all particles of the composition are mostly, generally, or completely suspended for at least about 75%, >~80%, >~85%, >~90%, >95%, or, e.g., about 100% of the time the product is being applied or administered or, e.g., such that the uniformity of the composition does not change over a period of at least about 5 minutes, such as, e.g., >~10 minutes, >~20 minutes, >~30 minutes, >~40 minutes, >~50 minutes, >~1 hour, >~3 hours, >~6 hours, >~12 hours, >~18 hours, >~24 hours, >~2 days, >~3 days, >~4 days, >~5 days, >~6 days, >~1 week, >~2 weeks, >~3 weeks, >~1 month, >~2 months, >~3 months, >~4 months, >~5 months, >~6 months, >~1 year, >~1.5 years, >~2 years, >~2.5 years, or, e.g., >~3 years or more.

In aspects, a suitable suspension is a suspension in which, if such a lack of uniformity of the composition changes such that administration of the composition may become unsuitable (e.g., there is a detectable level of agglomeration or flocculation of particles), most, generally all, substantially all, or all agglomeration of particles, e.g., any flocculation of particles, is resolved by shaking the compositions for a minimum of about 10 seconds, such as, e.g., at least about ~12 seconds, ~14 seconds, ~16 seconds, ~18 seconds, ~20 seconds, ~22 seconds, ~24 seconds, ~26 seconds, ~28 seconds, ~30 seconds, such as, e.g., at least about ~35 seconds, ~40 seconds, ~45 seconds, ~50 seconds, ~55 seconds, or, e.g., ~60 seconds. In aspects, most, generally all, substantially all, or all flocculation is resolved by shaking for less than about 60 seconds, such as by shaking for <~55 seconds, <~50 seconds, <~45 seconds, <~40 seconds, <~35 seconds, <~30 seconds, <~25 seconds, <~20 seconds, <~15 seconds, <~10 seconds, or, e.g., by shaking for less than about 5 seconds. In aspects, shaking for such period(s) of time results in less than about 40%, <~35%, <~30%, <~25%, <~20%, <~15%, <~10%, or, e.g., <~5% of the particles of the composition being flocculated, or, e.g., results in no detectable or significant particle flocculation.

In aspects, the invention provides compositions which are administered topically, such as, e.g., as drops. In aspects, compositions are provided in ready-to-use form, such as, e.g., prepackaged in dropper bottle(s) as is described elsewhere herein. In aspects, compositions are in the form of a suspension and are provided administered as drops to a mammalian eye in need of or benefitting from treatment therewith.

In aspects, compositions herein are administered by the application of 1-3 drops one to three times per day to a mammalian eye in need of or benefitting from treatment therewith. In aspects, the composition is administered by the application of 1-3 drops one to two times per day to a mammalian eye. In aspects, the composition is administered by the application of 1-3 drops once per day to a mammalian eye (e.g., the eye of a human patient, such as a human patient diagnosed with one or more conditions treatable by administration of the composition).

In aspects, the invention provides the compositions described herein which provide a reduction in the total amount of brinzolamide compound administered per 24-hour period, total amount of brimonidine compound administered per 24-hour period, total amount of brinzolamide compound and total amount of brimonidine compound administered per 24-hour period, the frequency of dosing per 24-hour period, or any combination thereof compared to an FDA approved reference product. In aspects, such an FDA approved reference product is Simbrinza®. In aspects, compositions provide an effective daily dose when administered once or twice per day to a reference composition administered three times per day (e.g., a similar or substantially equivalent reference compositions, e.g., an FDA approved reference product, such as, e.g., Simbrinza®). In aspects, an effective daily dose of the composition is bioequivalent to a daily dose of a similar or substantially identical product that provides about 30%, ~40%, ~50%, ~60%, ~70%, ~80%, ~90%, ~100%, ~125%, ~150%, ~175%, ~200%, ~225%, ~250%, ~275%, or ~300% or more of the amount of brinzolamide compound in the composition. In aspects, an effective daily dose of the composition is bioequivalent to a daily dose of a similar or substantially identical product that provides about 30%, ~40%, ~50%, ~60%, ~70%, ~80%, ~90%, ~100%, ~125%, ~150%, ~175%, ~200%, ~225%, ~250%, ~275%, or ~300% or more of the amount of brimonidine compound in the composition. In aspects, an effective daily dose of the composition is bioequivalent to a daily dose of a similar or substantially identical product that provides about 30%, ~40%, ~50%, ~60%, ~70%, ~80%, ~90%, ~100%, ~125%, ~150%, ~175%, ~200%, ~225%, ~250%, ~275%, or ~300% or more of the amount of brinzolamide compound and brimonidine compound in the composition.

In aspects, an effective daily dose of the composition is bioequivalent to a daily dose of a similar or substantially identical product that provides about 30%, ~40%, ~50%, ~60%, ~70%, ~80%, ~90%, ~100%, ~125%, ~150%, ~175%, ~200%, ~225%, ~250%, ~275%, or ~300% or more of the amount of brinzolamide compound in the composition.

In aspects, an effective daily dose of the composition is bioequivalent to a daily dose of a similar or substantially identical product comprising less than about 90% of the amount of benzalkonium chloride, such as less than ~80%, ~70%, ~60%, ~50%, ~40%, ~30%, ~20%, ~10%, ~5%, ~4%, ~3%, ~2%, or even a similar or substantially identical product comprising less than 1% of the amount of benzalkonium chloride.

In aspects, the invention provides pharmaceutically acceptable and ophthalmologically suitable compositions which provide an effective daily dose of less than or equal to about 30 mg per day of brinzolamide, such as less than about 28 mg/day, ≤~26 mg/day, ≤~24 mg/day, ≤~22 mg/day, and commonly less than or equal to ~20 mg/day, such as ≤~18 mg/day, ≤~16 mg/day, ≤~14 mg/day, ≤~12 mg/day, and in specific aspects ≤~10 mg/day, such as, e.g., 5-8 mg/day, ≤~6 mg/day, or ≤~4 mg/day. In aspects, the invention provides pharmaceutically acceptable and ophthalmologically suitable compositions which provide an effective daily dose of brinzolamide, however the effective daily dose is not greater than about 30 mg/day, such as, e.g., between about 1 mg to about 30 mg per day, ~2 mg-~29 mg/day, ~3 mg-~28 mg/day, ~4 mg-~27 mg/day, ~5 mg-~26 mg/day, ~6 mg-~25 mg/day, ~7 mg-~24 mg/day, ~8 mg-~23 mg/day, ~9 mg-~22 mg/day, ~10 mg-~21 mg/day, or, e.g., such as, e.g., ~5-~15 mg/day, ~15-~25 mg/day, or, e.g., ~10-~20 mg/day.

In aspects, the invention provides pharmaceutically acceptable and ophthalmologically suitable compositions which provide an effective daily dose of less than or equal to about 6 mg per day of brimonidine tartrate, such as less than about 5.5 mg/day, ~5 mg/day, ≤~4.5 mg/day, or commonly ≤~4 mg/day, such as ≤~3.5 mg/day, 5-3 mg/day, 5-2.5 mg/day, or in specific aspects ≤~2 mg/day, such as, e.g., ≤~1.5 mg/day, or ≤~1 mg/day. In aspects, the invention provides pharmaceutically acceptable and ophthalmologically suitable compositions which provide an effective daily dose of brimonidine tartrate, however the effective daily dose is not greater than about 6 mg/day, such as, e.g., between about 1 mg to about 6 mg per day, ~1-~5 mg/day, ~1-~4 mg/day, ~1-~3 mg/day, ~1-~2 mg/day, or, e.g., ~2-~6 mg/day, ~2-~5 mg/day, ~2-~4 mg/day, or, e.g., ~2-~3 mg/day.

In aspects, the invention provides pharmaceutically acceptable and ophthalmologically suitable compositions which provide an effective daily dose of each of brinzolamide and brimonidine, wherein the effective daily dose is less than or equal to ~20 mg/day brinzolamide and ≤~4 mg/day brimonidine tartrate.

In aspects, the invention provides pharmaceutically acceptable and ophthalmologically suitable compositions which provide an effective daily dose of each of brinzolamide and brimonidine, wherein the effective daily dose is less than or equal to ~10 mg/day brinzolamide and ≤~2 mg/day brimonidine tartrate.

In aspects, the effective daily dose is a daily dose effective in demonstrating a detectable or significant clinically relevant effect in treating ocular hypertension or elevated intraocular pressure, such as, e.g., elevated intraocular pressure in patients with glaucoma, e.g., open-angle glaucoma or ocular hypertension or both.

Target Conditions & Related Outcomes

Target Conditions

In aspects, the invention provides compositions as described herein wherein the composition is administered to a mammalian eye to treat elevated intraocular pressure (IOP).

In aspects, the invention provides compositions as described herein wherein the composition is administered to a mammalian eye to treat elevated intraocular pressure (IOP) in a patient diagnosed with or suffering from glaucoma.

In aspects, the invention provides compositions as described herein wherein the composition is administered to a mammalian eye to treat elevated intraocular pressure (IOP) in a patient diagnosed with or suffering from open-angle glaucoma. In any case where "mammalian eye" is used to describe an aspect, such disclosure implicitly provides support for a related aspect wherein the mammalian eye is an eye of a human patient, such as a patient diagnosed with having or being at risk of developing one or more conditions treatable by a composition.

In aspects, the invention provides compositions as described herein wherein the composition is administered to a mammalian eye to treat patients diagnosed with or suffering from irritation of the cornea.

In aspects, the invention provides compositions as described herein wherein the composition is administered to a mammalian eye to treat patients diagnosed with or suffering from irritation of ocular tissue adjacent to the cornea.

In aspects, the invention provides compositions as described herein wherein the composition is administered to a mammalian eye to treat patients diagnosed with or suffering from dry eye(s).

In aspects, the invention provides compositions as described herein wherein the composition is administered to a mammalian eye to treat patients diagnosed with or suffering from a plurality of the above-described conditions.

Related Outcomes

In aspects, compositions provided by the invention detectably or significantly reduce intraocular pressure ("IOP"), e.g., when administered in a dose of 1-3 drops 1-3 times per day, such as 1-2 drops administered twice per day, 1 drop administered twice per day, 1-2 drops administered once per day, or 1 drop administered once per day. In aspects, compositions provided by the invention detectably or significantly reduce IOP when administered no more than 3 times per day (i.e., per 24-hour period). In aspects, compositions provided by the invention detectably or significantly reduce IOP when administered no more than 2 times per day (24-hour period). In aspects, compositions provided by the invention detectably or significantly reduce IOP when administered no more than 1 time per day (24-hour period).

In aspects, compositions provided by the invention detectably or significantly reduce IOP when administered via a dosing regimen which provides a detectable or significant reduction in the total amount (e.g., total mg amount) of brinzolamide compound administered per day compared to an FDA approved reference product, e.g., Simbrinza®.

In aspects, compositions provided by the invention detectably or significantly reduce IOP when administered via a dosing regimen which provides a detectable or significant reduction in the total amount (e.g., total mg amount) of brimonidine compound (e.g., brimonidine tartrate) administered per day compared to an FDA approved reference product, e.g., Simbrinza®.

In aspects, compositions provided by the invention detectably or significantly reduce IOP when administered via a dosing regimen which provides a detectable or significant reduction in the total amount (e.g., total mg amount) of brinzolamide compound and brimonidine compound (e.g., brimonidine tartrate) administered per day compared to an FDA approved reference product, e.g., Simbrinza®.

In aspects, compositions provided by the invention detectably or significantly reduce IOP when administered via a dosing regimen which provides a less frequent dosing regimen compared to an FDA approved reference product, e.g., Simbrinza®, such as a dosing schedule requiring ⅔ or ⅓ of the doses required by an FDA approved reference product, e.g., Simbrinza®.

In aspects, topical ocular administration of compositions provided by the invention to a mammalian result in detectable or significant vasoconstriction in scleral vessels in a measurably, e.g., detectably or significantly, shorter period of time than that attained by an FDA approved reference product, e.g., Simbrinza®.

In aspects, topical ocular administration of compositions provided by the invention to a mammalian result in detectable or significant reduction in the flux of blood through the anterior portion of the eye in a measurably, e.g., detectably or significantly, shorter period of time than that attained by an FDA approved reference product, e.g., Simbrinza®.

In aspects, 1 drop twice per day administration, or 1 drop once per day administration, of compositions provided by the invention results in detectably or significantly fewer adverse events than that of an FDA approved reference product (e.g., Simbrinza®) comprising the same amount of brinzolamide compound, the same amount of brimonidine compound, and 0.003 wt. % of benzalkonium chloride administered as one drop three times per day. Such adverse events are described elsewhere herein.

Methods of Use

In aspects, compositions provided by the invention are used to treat conditions wherein the cornea or adjacent ocular tissues are irritated, or conditions requiring frequent application of a composition, such as in the treatment of dry eye patients, treatment of glaucoma (e.g., open-angle glaucoma), or ocular hypertension. In aspects, the invention provides methods of treating any one or more of elevated IOP, such as elevated IOP associated with glaucoma or, e.g., more specifically, open-angle glaucoma, irritation of the cornea, irritation of ocular tissue adjacent the cornea, dry eye, or any combination thereof. Methods also can be employed (and compositions can be useful in) the treatment of any other disease, condition, etc., which is associated with the combination of the active ingredients of the compositions.

In aspects, the invention provides methods of treating any one or more of elevated IOP, such as elevated IOP associated with glaucoma or, e.g., more specifically, open-angle glaucoma, irritation of the cornea, irritation of ocular tissue adjacent the cornea, dry eye, or any combination thereof with a composition described herein.

In aspects, the invention provides methods for establishing and maintaining an acceptable intraocular pressure level in recipient eye(s) comprising repeat administration of compositions herein. In aspects, the invention provides methods for maintaining an acceptable intraocular pressure level in recipient eye(s) comprising repeat administration of compositions herein. In aspects, the invention provides methods for maintaining an acceptable intraocular pressure level in recipient eye(s) comprising the chronic administration of composition(s) herein, e.g., wherein the method comprises repeating the administration of compositions herein over the course of about 1 month, ~2 months, ~6 months, ~12 months, ~24 months, ~36 months, ~48 months, ~5 years, ~10 years, ~20 years ~30 years, ~40 years, ~50 years or longer, such as, e.g., over the course of the remaining lifetime of a patient diagnosed with elevated intraocular pressure, such as, e.g., elevated IOP associated with glaucoma, e.g., open-angle glaucoma.

In aspects, methods provided by the invention comprise administration of compositions in which 1-3 drops are administered 1-3 times per day, e.g., 1-2 drops 1-3 times per day, 1 drop 1-3 times per day, 1-2 drops 1-3 times per day, or 1 drop 1-3 times per day, such as 1 drop 1-2 times per day, or 1 drop once per day.

In aspects, the invention provides methods of achieving at least bioequivalence, or, e.g., improved effect, over that of an FDA approved reference product requiring a one drop 3 times per day dosing schedule (e.g., Simbrinza®), when administered as one drop twice per day as determined by an FDA approved clinical endpoint study.

In aspects, the invention provides methods of achieving at least bioequivalence, or, e.g., improved effect, over that of an FDA approved reference product requiring a one drop 3 times per day dosing schedule (e.g., Simbrinza®), when administered as one drop once per day as determined by an FDA approved clinical endpoint study.

In aspects, the invention provides a method of using a composition comprising the same amount of a brinzolamide compound, the same amount of a brimonidine compound (e.g., brimonidine tartrate), and a detectably or significantly higher amount of a penetration agent (e.g., benzalkonium chloride) to obtain bioequivalence with an FDA approved reference product (e.g., Simbrinza® when administered at a dosing frequency which is at least ⅔ that of the FDA approved reference product (e.g., Simbrinza®).

In aspects, the invention provides a method of using a composition comprising the same amount of a brinzolamide compound, the same amount of a brimonidine compound (e.g., brimonidine tartrate), and a detectably or significantly higher amount of a penetration agent (e.g., benzalkonium chloride) to obtain bioequivalence with an FDA approved reference product (e.g., Simbrinza® when administered at a dosing frequency which is ⅓ that of the FDA approved reference product (e.g., Simbrinza®).

In aspects, the invention provides a method of achieving a clinically relevant reduction in ocular hypertension by administration of a composition described herein which is attained by administration of such a composition via a dosing regimen that is ⅔ or ⅓ that of an FDA approved reference product (e.g., Simbrinza®). In aspects, detection of such a clinically relevant reduction in ocular hypertension is achieved in a detectably or significantly shorter time period than that of an FDA approved reference product (e.g., Simbrinza®), lasts a detectably or significantly longer period of time that that of an FDA approved reference product (e.g., Simbrinza®), or is both achieved in a detectably or significantly shorter time period and lasts a detectably or significantly longer period of time than that of an FDA approved reference product (e.g., Simbrinza®).

In aspects, a peak ocular hypotensive effect of brinzolamide in compositions provided by the invention occurs within 3 hours of administration, such as, e.g., within ~2.75 hours, ~2.5 hours, ~2.25 hours, or ~2 hours or less of administration.

In aspects, clinically relevant hypotensive effect of brinzolamide, brimonidine tartrate, or both in compositions provided by the invention lasts a detectably or significantly longer period of time that that provided by an FDA approved reference product (e.g., Simbrinza®).

In aspects, the invention provides methods of administering a composition described herein wherein the method results in a detectable or significant reduction in one or more adverse events compared to an FDA approved reference product (e.g., Simbrinza®) when administered to treat the same condition. Surprisingly, compositions herein provide a safe and effective tool for lowering intraocular pressure. One advantage of compositions herein is the provision of safe and effective compositions which demonstrate efficacy in lowering intraocular pressure. In aspects, one advantage of the compositions herein is their safety and efficacy in lowering intraocular pressure when administered once or twice per day compared to a reference product administered three times per day. In aspects, one advantage of the compositions herein is their safety and efficacy in lowering intraocular pressure when providing a lower daily dose of actives (e.g., an effective daily dose which is, e.g., ⅔ or ⅓ of the actives) of a reference product. In aspects, a reference product is an FDA approved reference product. In aspects, the reference product is Simbrinza®. In aspects, methods provide detectably or significantly greater bioavailability or penetration of API(s) in ocular tissue with detectably or significantly fewer adverse events than an FDA approved reference product. In aspects, such adverse events include, e.g., sedation, ocular hyperemia, visual disturbance, ocular burning, foreign body sensation, eye pain, blepharitis, cataract, superficial punctate keratitis, eyelid erythema, ocular irritation, eye discharge, tearing, photophobia, allergic conjunctivitis, asthenopia, conjunctival edema, conjunctival hemorrhage, and intraocular inflammation.

According to one exemplary aspect, the invention provides a method of treating intraocular pressure, or ocular hypertension (elevated intraocular pressure (IOP), comprising administration of a pharmaceutically acceptable and ophthalmologically suitable composition comprising (a) a brinzolamide compound in an amount of between about 0.1 wt. %-about 10 wt. % of the composition; (b) a brimonidine compound (e.g., brimonidine tartrate) in an amount of between about 0.01 wt. %-about 0.5 wt. % of the composition; and (c) one or more borate-polyol complexes, wherein the total of the one or more borate-polyol complexes are present in an amount of between about 0.5 wt. %-about 6 wt. % of the composition, wherein the method results in bioequivalent or detectably or significantly improved pharmacokinetic properties when administered one time or two times per 24-hour period compared to the same one or more pharmacokinetic properties of a composition comprising the same amount of brinzolamide and the same amount of brimonidine administered three times per 24-hour period. In aspects, the IOP is associated with glaucoma. In aspects, the glaucoma is open-angle glaucoma. In this and any similarly described aspects, the comparator product can be a similar reference product or substantially identical reference product, as described elsewhere (e.g., being the same in most or generally all ingredients, except for, e.g., in respect of the penetration enhancer component).

In another exemplary aspect, the invention provides a method of treating intraocular pressure, or ocular hypertension (elevated intraocular pressure (IOP), comprising administration of a pharmaceutically acceptable and ophthalmologically suitable composition comprising: (a) a brinzolamide compound in an amount of between about 0.1 wt. %-about 10 wt. % of the composition; (b) a brimonidine compound (e.g., brimonidine tartrate) in an amount of between about 0.01 wt. %-about 0.5 wt. % of the composition; and (c) one or more borate-polyol complexes, wherein the total of the one or more borate-polyol complexes are present in an amount of between about 0.5 wt. %-about 6 wt. % of the composition; and (d) benzalkonium chloride in an amount between 0.005-about 0.02 wt. % of the composition. In aspects, the IOP is associated with glaucoma. In aspects, the glaucoma is open-angle glaucoma.

In a further exemplary aspect, the invention provides a method of treating irritation of the cornea, irritation of ocular tissue adjacent the cornea, or dry eye, comprising administration of a pharmaceutically acceptable and ophthalmologically suitable composition comprising (a) a brinzolamide compound in an amount of between about 0.1 wt. %-about 10 wt. % of the composition; (b) a brimonidine compound (e.g., brimonidine tartrate) in an amount of between about 0.01 wt. %-about 0.5 wt. % of the composition; and (c) one or more borate-polyol complexes, wherein the total of the one or more borate-polyol complexes are present in an amount of between about 0.5 wt. %-about 6 wt. % of the composition, wherein the method results in bioequivalent or detectably or significantly improved pharmacokinetic properties when administered one time or two times per 24-hour period compared to the same one or more pharmacokinetic properties of a composition comprising the same amount of brinzolamide and the same amount of brimonidine administered three times per 24-hour period.

In yet a further exemplary aspect, the invention provides a method of treating irritation of the cornea, irritation of ocular tissue adjacent the cornea, or dry eye, comprising administration of a pharmaceutically acceptable and ophthalmologically suitable composition comprising: (a) a brinzolamide compound in an amount of between about 0.1 wt. %-about 10 wt. % of the composition; (b) a brimonidine compound (e.g., brimonidine tartrate) in an amount of between about 0.01 wt. %-about 0.5 wt. % of the composition; and (c) one or more borate-polyol complexes, wherein the total of the one or more borate-polyol complexes are present in an amount of between about 0.5 wt. %-about 6 wt. % of the composition; and (d) benzalkonium chloride in an amount between 0.005-about 0.02 wt. % of the composition.

In one aspect, the invention provides a method comprising administration of a pharmaceutically acceptable and ophthalmologically suitable composition comprising a pharmaceutically acceptable and ophthalmologically suitable brinzolamide compound in an amount of about 0.1 wt. %-about 10 wt. % of the composition; and a pharmaceutically acceptable and ophthalmologically suitable brimonidine compound in an amount of about 0.01 wt. %-about 0.5 wt. % of the composition, wherein performing the method results in an effective daily dose of the composition which is bioequivalent to a daily dose of a similar or substantially identical product that comprises about 200% to about 300% of the amount of the brinzolamide compound in the composition and about 200% to about 300% of the amount of the brimonidine compound in the composition.

In aspects, the invention provides a method of topically administering any one or more of the above-described compositions to an eye, which can be, e.g., a suspension, comprising effective amounts of brinzolamide, brimonidine, and optionally, e.g., one or more other agents, such as a penetration enhancer, e.g., an effective amount of BKC, such as to physiologically change a condition of the eye, induce/promote/cause a detectable or significant physiological effect, etc.

Process for Manufacturing

In aspects, the invention provides methods (processes) for manufacturing compositions described herein.

In aspects, the process for manufacturing compositions described herein comprise multiple parts, such as 1, 2, or 3 or more parts, wherein each part can be completed, at least in part, independently from one or more other parts. As used here, a "part" of a manufacturing process means one or more steps which can be performed independently of, such as for example in aspects, in parallel with, one or more separate steps of the manufacturing process.

In aspects, the process for manufacturing compositions described herein comprise 1 or more, such as, e.g., ≥2 or ≥3 sterilization steps. In aspects, when 2 or more sterilization steps are utilized, 2 or more of the sterilization steps can utilize the same sterilization technology. In aspects, when 2 or more sterilization steps are utilized, 2 or more of the sterilization steps can utilize different technologies. For example, in aspects, the manufacturing process comprises at least 2 sterilization steps. In aspects, the manufacturing process comprises at least 2 sterilization steps comprising sterile filtering at least one component of the composition (e.g., a solution representing a portion of a final composition). In aspects, the manufacturing process comprises at least 2 sterilization steps comprising at least one sterilization step utilizing sterile filtration and at least one sterilization step utilizing heat (e.g., comprising use of an autoclave).

In aspects, the process for manufacturing compositions of the invention can be characterized as having at least two parts. In aspects, a first part comprises the solubilization of all composition components except for a solubilizer or at least one constituent of a solubilizer component, at least 2 active ingredients, or both a solubilizer or at least 1 constituent of a solubilizer component and at least 2 active ingredients. In aspects, the at least 1 solubilizer comprises tyloxapol, polysorbate-80, tocopherol polyethylene glycol succinate (TPGS), polyoxyl-35 castor oil, poly-arginine, polyserine, tromethamine (tris), sesame seed oil alone or in any combination thereof. In aspects, at least one active ingredient is a carbonic anhydrase inhibitor (CAI). In aspects, the at least one CAI is a brinzolamide compound. In aspects, the brinzolamide compound is brinzolamide. In aspects, at least one active ingredient is an alpha-2-adrenergic agonist. In aspects, the at least one alpha-2-adrenergic agonist is a brimonidine compound. In aspects, the brimonidine compound is a salt of brimonidine. In aspects, the salt of brimonidine is brimonidine tartrate.

In aspects, a second part of the manufacturing process comprises the creation of a mixture of one or more ingredients having a density higher (e.g., significantly greater) than that of water suspended in liquid (e.g., the creation of a "slurry"). In aspects, the slurry is a slurry containing one or more active ingredients. In aspects, the one or more active ingredients forming a slurry comprises a carbonic anhydrase inhibitor (CAI). In aspects, the at least one CAI is a brinzolamide compound. In aspects, the brinzolamide compound is brinzolamide. In aspects, the one or more active ingredients forming a slurry is an alpha-2-adrenergic agonist. In aspects, the at least one alpha-2-adrenergic agonist is a brimonidine compound. In aspects, the brimonidine compound is a salt of brimonidine. In aspects, the salt of brimonidine is brimonidine tartrate. In aspects, a second part of the manufacturing process comprises the creation of a slurry of a brinzolamide compound, e.g., brinzolamide tartrate.

In aspects, the manufacturing process comprises the combination of the products resulting from the performance of steps representing at least two parts of a complete manufacturing process. In aspects, the manufacturing process comprises the combination of the product resulting from a first part as described above with a second part as also described above.

According to specific aspects, a manufacturing process provided by the invention comprises collection of a fraction of the total amount of a carrier to be used in the manufacturing process. In aspects, the carrier is water, e.g., water for injection (WFI). In aspects, the manufacturing process comprises collection of, e.g., about 50%, ~55%, ~60%, ~65%, ~70%, or, e.g., ~75% or ~80% or more of the total carrier. In aspects, ~60%-~70%, such as, e.g., ~65% of the total carrier is collected in a clean container. In aspects, the collected carrier (e.g., WFI) is brought to about room temperature (e.g., between ~10-~30° C., or, e.g., ~15-~25° C., such as about 20° C.). In aspects, the carrier is stirred until it reaches about room temperature.

In aspects, a manufacturing process comprises the addition of 2 or more ingredients to the collected room temperature carrier. In aspects, the addition of the 2 or more ingredients is performed such that the 2 or more ingredients are added to the carrier one-by-one, allowing for the complete dissolution of the previously added ingredient prior to the addition of the next ingredient. In aspects, ingredients added comprise a tonicity component or one or more tonicity agents, a polyol component or one or more polyol compounds, a borate component or one or more borate compounds, a penetration enhancer component or one or more penetration enhancer compounds, a viscosity-enhancement component or suspension component or one or more viscosity-enhancing or suspension compounds, or any combination of any or all thereof. In specific exemplary aspects, ingredients added comprise sodium chloride, mannitol, propylene glycol, boric acid, benzalkonium chloride, and a carbomer polymer, such as Carbomer 974P or a polymer that results in significantly similar properties/effects in such a composition. In aspects, ingredients are added in that that given order, allowing each ingredient to completely dissolve prior to the addition of the next ingredient.

In aspects, once the above-described ingredients are dissolved, the manufacturing process comprises stirring the resulting solution for at least about 20 minutes, such as, e.g., ≥~22 minutes, ≥~24 minutes, ≥~26 minutes, ≥~28 minutes, ≥~30 minutes, ≥~32 minutes, ≥~34 minutes, ≥~36 minutes, ≥~38 minutes, or, e.g., ≥~40 minutes, such as, e.g., ~30 minutes to ensure complete dissolution of all ingredients.

In aspects, the manufacturing process comprises a step of sterilizing the solution resulting from the process described in the preceding paragraph. In aspects, such a sterilization step can comprise any method of sterilization known in the art resulting in sufficient elimination of microbial contaminant(s). In aspects, such a sterilization method can comprise, e.g., sterilization using heat (e.g., via use of an autoclave), filtration, gas, or radiation. In aspects, sterile filtration is used to sterilize the solution resulting from the above-described process(es). In aspects, a 0.2-micron filter is used to filter the resulting solution into a separate container. For ease of reference, such a separate container is referred to as the "main vessel", as later steps in the manufacturing process can reference such a container. In aspects, the container is suitable for sterilization by, e.g., heat sterilization (such that, e.g., the container is autoclavable).

In aspects, the manufacturing process comprises pH adjusting the sterilized solution resulting from the steps of the preceding paragraph. In aspects, the pH of the solution is adjusted using any suitable pH adjusting agent, such as hydrochloric acid (HCl), sodium hydroxide (NaOH), and other pH adjusting agents well known in the art. In aspects, 0.1 N HCL, 0.1 N NaOH, or both, are used to adjust the pH of the solution. In aspects, the pH of the solution is brought to between about 4.0-about 7.5, such as, e.g., between ~5.0-~7.0, ~5.5-~7.0, or between ~6.0-~7.0, such as, e.g., a pH of ~6.5.

In aspects, the manufacturing process comprises bringing the pH-adjusted up, using additional carrier, e.g., WFI, to a weight which is a fraction of the total final weight of the composition. In aspects, additional carrier (e.g., WFI) is added to bring the weight of the composition up to between about 60%-about 80%, e.g., between ~60-~75%, ~60-~70%, ~65-~80%, ~70-~80%, as in, e.g., between ~65-~75%, or which is, e.g., ~70% of the total final weight of the composition.

In aspects, once the composition resulting from the step described in the preceding paragraph is brought up to a pre-determined weight, the manufacturing process comprises a step of sterilizing the resulting solution. In aspects, such a sterilization step can comprise any sterilization method known in the art such as, e.g., sterilization using heat (e.g., via use of an autoclave), filtration, gas, or radiation. In aspects, the sterilization step comprises use of heat. In aspects, the composition is sterilized using an autoclave. In aspects, any sterilization method known in the art can be used for sterilizing the suspension. In aspects, the suspension is sterilized using an autoclave. In aspects, the suspension is autoclaved at between about 115° C.-135° C. for up to 1 hour. For example, the suspension is autoclaved at 121° C. for about 20-about 40 minutes, such as, e.g., ~20 minutes, ~25 minutes, ~30 minutes, ~35 minutes, or, e.g., ~40 minutes. In aspects, the suspension is autoclaved for a sufficient amount of time and at a sufficient temperature to sterilize the composition by thermal lethalization without negatively impacting any one or more ingredients, such as e.g., causing DOS degradation of any one or more ingredients. In aspects, the time and temperature of the sterilization step do not result in a reduction in a DOS amount of any one or more ingredients. In aspects, the time and temperature of the sterilization step do not result in the reduction of a DOS in an amount of activity which an ingredient can impart either to the composition or which the ingredient can impart therapeutically upon administration. In aspects, the sterilization step detectably or significantly reduces the amount(s) of related compound(s) and impurities associated with the ophthalmic composition upon storage of the composition at about 25° C. and about 40% relative humidity, at about 40° C. and not more than 25% relative humidity for a period of at least about 1 month, e.g., at least ~2, ~3, ~4, ~5, or, e.g., ~6 months or more (e.g., ≥12, ≥18, or ≥~24 months). In specific embodiments, the resulting composition is autoclaved for ~20 minutes at ~121° C. within the main vessel.

In aspects, after completion of the sterilization step described in the preceding paragraph, the manufacturing process comprises allowing the resulting composition within the main vessel to cool to about room temperature (e.g., between ~10-~30° C., or, e.g., ~15-~25° C., such as about 20° C.). In aspects, cooling can be aided, e.g., one or more methods of facilitating faster cooling can be applied, e.g., via use of a water jacket or other cooling methods known in the art.

According to aspects, between about 30-about 50%, e.g., between ~30-~45%, ~30-~40%, between ~35-~45%, ~30-~40%, or, e.g., ~40% of the remaining required carrier (e.g., WFI) is collected separately. In aspects, this portion of the carrier is cooled under nitrogen purging.

In aspects, between about 10%-about 30% of the remaining carrier (e.g., WFI) is collected, such as, e.g., between ~10-~25%, ~10-~20%, between ~15-~25%, ~15-~20%, or, e.g., ~20% of the remaining required total volume of carrier is collected. In aspects, the manufacturing process comprises adding the required amount of a solubilizing component or at least one or more solubilizing compounds to this portion of the carrier. In aspects, the solubilizing component comprises tyloxapol. In aspects, tyloxapol is the only solubilizing compound added at this step of the manufacturing process. In aspects, the manufacturing process comprises stirring the solubilizing component, e.g., solubilizing compound (e.g., tyloxapol) until it is completely dissolved.

In aspects, the manufacturing process comprises adding, to the solution resulting from the preceding paragraph (e.g., tyloxapol solution), the required amount of at least one alpha-2-adrenergic agonist. In aspects, the at least one alpha-2-adrenergic agonist is a brimonidine compound. In aspects, the brimonidine compound is brimonidine tartrate. In aspects, the at least one alpha-2-adrenergic agonist (e.g., brimonidine tartrate) is stirred until completely dissolved.

According to aspects, the manufacturing process comprises a step for sterilizing the solubilizing agent-alpha-2-adrenergic agonist solution resulting from the steps performed in the preceding paragraphs. In aspects, the tyloxapol-brimonidine tartrate solution is sterilized using any sterilization method known in the art, such as, e.g., sterilization using heat (e.g., via use of an autoclave), filtration, gas, or radiation. In aspects, the solution is sterilized using filtration. In aspects, the solution is sterile filtered using a 0.2-micron filter.

In aspects, the manufacturing process comprises the sterile filtration step as described in the preceding paragraph, wherein the solution is sterile filtered into a container in communication with (e.g., connected to) a process or equipment capable of establishing a pre-determined particle size of components to which it is exposed. In aspects, the solution is sterile filtered into a container (e.g., a sterile container) connected to a homogenizer.

In aspects, after sterile filtration of the solution which it previously held, the emptied container previously holding the, e.g., tyloxapol-brimonidine tartrate solution, is rinsed with a fraction of the remaining carrier, with the resulting rinsing solution also sterile filtered into the container connected to an, e.g., homogenizer.

According to aspects, the manufacturing process comprises the addition of one or more carbonic anhydrase inhibitors (CAIs) to the solution resulting from the step described in the preceding paragraph; that is, to the sterilized solution comprising, e.g., tyloxapol and brimonidine. In aspects, the one or more CAIs comprise a brinzolamide compound. In aspects, the brinzolamide compound is brinzolamide.

In aspects, the addition of a brinzolamide compound (e.g., brinzolamide) forms a slurry, e.g., a mixture of brinzolamide as a solid component suspended in the tyloxapol-brimonidine solution.

In aspects, the manufacturing process comprises a step of homogenizing the suspension, e.g., the "slurry", resulting from the step of the preceding paragraph, for a period of between about 1-about 3 hours, such as, e.g., between ~1-~2.5 hours, ~1-~2 hours, ~1-1.5 hours, ~1.5-~3 hours, ~1.5-~2.5 hours, ~1.5-~2 hours, or, e.g., for a period of time sufficient to obtain an average target particle size. In aspects, the manufacturing process comprises a step of homogenizing the suspension resulting from the step of the preceding paragraph, for a period of time sufficient to obtain an average particle size of between about 1 μm-about 3 μm, such as, e.g., ~1-~2.5 μm, ~1-~2 μm, ~1-~1.5 μm, ~1.5-~3 μm, ~2-~3 μm, ~2.5-~3 μm, or, e.g., between ~1.5-~2.5 μm. In aspects, samples, e.g., small-quantity samples, can be collected (e.g., aseptically collected) 1 or more times throughout the homogenization process and analyzed to determine the average particle size.

In aspects, the manufacturing process comprises a step of transferring the suspension, after the target average particle size has been achieved and the suspension is satisfactorily homogenized, to the main vessel comprising the previously created and sterilized solution described above.

In aspects, the manufacturing process comprises sterilizing, e.g., by sterile filtration, a fraction of remaining carrier (e.g., WFI), and using the sterilized carrier to rinse the container previously holding the suspension and the homogenizer. In aspects, the rinse material is then aseptically transferred to the main vessel.

In aspects, as a final step in the manufacturing process (e.g., final step prior to packaging), remaining carrier is added to the main vessel to bring the final volume (alternatively stated as the final weight) of the composition to 100% of the final total volume (total weight).

In aspects, as alluded to above, the manufacturing process comprises one or more sterilization step(s). In aspects, the method of manufacturing can comprise any suitable one or more sterilization methods capable of yielding a composition free of detectable or significant material or microbial contamination. In aspects, such a sterilization step can comprise any suitable sterilization method known in the art, such as, e.g., heat sterilization, gaseous sterilization, filtration sterilization, or radiation sterilization. In aspects, such steps, as with other steps described herein with respect to a functional result, can also be characterized in methods as "steps for" performing a function, such as a "step for sterilizing" a composition, thus incorporating equivalent means for sterilization known presently in the art. According to aspects, the invention provides a process for preparing and sterilizing the compositions which results in a detectable or significant reduction in the amount of related compounds and impurities associated with the ophthalmic compositions upon storage. In aspects, the process for preparing and sterilizing the compositions provided by the invention results in a detectable or significant reduction in the amount of related compounds and impurities associated with the compositions upon storage at about 25° C. and about 40% relative humidity or at about 40° C. and 25% relative humidity for a period of at least about 1 month, ≥~2 months, ≥~3 months, ≥~4 months, ~5 months, ≥~6 months, ≥~8 months, ≥~10 months, ≥~12 months, ≥~14 months, ≥~16 months, ≥~18 months, ≥~20 months, ≥~22 months, or, e.g., ≥~24 months.

In specific aspects, the method provides a process for preparing, e.g., a process for manufacturing, a pharmaceutically acceptable and ophthalmologically suitable composition comprising a brinzolamide compound in an amount of about 0.1% to about 10% by weight, a brimonidine compound in an amount of about 0.01% to about 0.5% by weight, a borate-polyol complex in an amount of about 0.5 to about 6% by weight, and one or more pharmaceutically acceptable excipients, including benzalkonium chloride (BKC), wherein the BKC concentration is greater than about 0.005 wt. %. In aspects, the BKC concentration is less than about 0.02 wt. %. In aspects, the BKC concentration is between ~0.005-~0.02 wt. %. In aspects, the resulting composition provides one or more pharmacokinetic properties when dosed once or twice per day (e.g., per 24-hour period) that is/are at least substantially or effectively bioequivalent to the same one or more pharmacokinetics of a composition having the same amounts of brinzolamide compound and brimonidine compound administered three times per day.

Packaging and Kits

Packaging

According to certain embodiments, ophthalmologically suitable compositions of the invention can be packaged in any suitable packaging, such suitability being at least in part defined by protecting the compositions held therein from degradation, contamination, or both. In aspects, compositions are packaged in ready to use form. In aspects, compositions are packaged in ready to use form an only require brief manual shaking (e.g., sufficient to obtain a uniform suspension as described herein) prior to ocular administration.

In certain aspects, suitable packaging materials are materials which exhibit less than about 20%, such as <~18%, <~16%, <~14%, <~12%, <~10%, <~8%, <~6%, <~4%, <~2% or even less sorption of anu API, e.g., a brinzolamide or brimonidine compound. In some respects, suitable materials include but may not be limited to packaging material made of select polyolefins, such as, e.g., DuPont® 20 LDPE, Chevron 5502 HDPE, Atofina 3020 PP, polypropylene homopolymers, low ethylene content (<8%) polypropylenes, and polymers (HDPE, PP) with low content of additives (<5%) and with low flexural modulus (<200 kpsi). In some respects, a suitable material is an EP-quality LDPE which, in further aspects, may contain no additives. In aspects, suitable packaging can comprise a polypropylene container provided that that polypropylene container is not packaged in a bag/container containing an iron oxide oxygen scavenger.

In certain aspects, the packaging can comprise or can be mostly comprised of (e.g., comprise in an amount ≥~10%, ≥~20%, ≥~30%, ≥~40%, or ≥~50%, such as, e.g., comprise in an amount ≥~60%, ≥~70%, ≥~80%, ≥~90% or more) an ultraviolet-light blocking agent or material. In aspects, such a material can be capable of blocking ≥~1%, ≥~5%, ≥~10%, ≥~20%, ≥~30%, ≥~40%, or ≥~50%, such as, e.g., ≥~60%, ≥~70%, ≥~80%, ≥~90% or more of the ultraviolet light in the environment from entering the container. In aspects, compositions described herein can be packaged in, stored, in, or both packaged and stored in a container wherein the container significantly reduces exposure of the composition to UV B radiation, such as by at least about 50%, at least about 65%, at least about 75%, at least about 90%, at least about 95%, or at least 99%. In some aspect the packaging material of a composition described herein is semi- or completely opaque, while in alternative aspects, the packaging is semi- or completely clear. In aspects, packaging can comprise different parts wherein one component of the packaging comprises a first material and one or more components of the packaging contain a second (or more) material(s).

In certain aspects, packaging can be selected based on the method of delivery of the compositions herein (e.g., compositions provided as a liquid for administration by drop(s) can be provided in suitable packaging for liquids, e.g., in a user-friendly dropper bottle.) In aspects, the compositions of the invention are stored in a packaging that facilitates the delivery of the composition as eye drops.

In one aspect, the ophthalmic compositions comprise brinzolamide compound(s), brimonidine compound(s), and one or more pharmaceutically acceptable excipient(s), and are provided in single-dose bottles. In an alternative aspect, such compositions are provided in multi-dose bottles, such as multi-dose eye dropper bottles. In aspects, such multi-dose bottles allow for the composition, e.g., provided as a solution to be dropped into the recipient's eye(s), to be applied as liquid drops over a course of treatment, such as, e.g., over the course of many days, several weeks, or longer. In aspects, a single dose package comprises a single dose of composition within a single dose administration container. In aspects, a multi-dose package comprises a plurality of single dose administration containers. In aspects, a multi-dose package comprises a plurality of doses within a single administration container. For example, a multi-dose package can be, e.g., a single dropper bottle comprising sufficient volume of composition to administer the composition multiple times over the course of an administration period, such as (but certainly not limited to) administration of about 1-3×/day over a period of about 1-7 days, or, e.g., 1-14 days, 1-30 days, 1-60 days, 1-90 days, or longer.

In aspects, the average force required to release one or more drops of the compositions described herein from a dropper bottle (a standard bottle common in the art for dispensing liquid in droplet form), by compressing the middle section of the storage body of such a dropper bottle, ranges between about 1.7-2.8 kg for release of the first drop, e.g., between about 1.7-2.6, ~1.7-2.4, ~1.7-2.2, or between about ~1.7-2.0. In aspects, successive drops can require more tension, such as can require an additional ~20-30% of force for release of the second drop, and, e.g., an additional force of ~24-50% for release of the third drop.

In aspects, packaging of compositions is any suitable packaging which effectively provides compositions with a shelf life (as defined elsewhere herein) of at least about 1 month, such as, e.g., ≥~3 weeks, ≥~4 weeks (1 month), ≥~5 weeks, ≥~6 weeks, ≥~7 weeks, ≥~8 weeks (2 months), ≥~9 weeks, ≥~10 weeks, ≥~11 weeks, ≥~12 weeks (3 months), ≥~13 weeks, ≥~14 weeks, ≥~15 weeks, ≥~16 weeks (4 months), or more, such as ≥~5 months, ≥~6 months, ≥~7 months, ≥~8 months, ≥~9 months, ≥~10 months, ≥~11 months, or ≥~12 months (1 year), or even longer, such as, ≥~18 months, ≥~24 months (2 years), ≥~30 months, or, e.g., ≥~~36 months (3 years) or longer.

In aspects, suitable packaging can comprise a container as described above which is suitable for administration of compositions held therein in a drop-by-drop manner, e.g., a dropper bottle, wherein the container holds between about 1 mL-about 50 mL of composition, e.g., between ~1-~45 mL, ~1-~40 mL, ~1-~35 mL, ~1-~30 mL, ~1-~25 mL, or ~1-~20 mL of composition.

"Kits" (Collections of Components or Compositions and Related Material)

In aspects, the invention provides kits comprising an ophthalmologically suitable composition according to any one or more of the compositions provided by aspects of the invention described herein, packaged in one or more containers, e.g., one or more single dose or multi-dose containers. In aspects, a kit comprises one or more delivery devices for administering the composition to a recipient. In aspects, kits comprise one or more container means, which can include containers described elsewhere (e.g., pharmaceutically acceptable dropper bottles) or known equivalents thereof. In aspects, the invention provides kits for storing, distributing, or storing and distributing compositions described herein.

In aspects, the invention provides a kit wherein compositions are pre-filled in a delivery device, and a kit comprises one or more pre-filled delivery devices and one or more additional components to facilitate administration of the composition(s). For example, in aspects the invention provides a kit wherein compositions are pre-filled in dropper bottle to facilitate topical administration by drop(s) to a mammalian eye. In aspects, the invention provides a kit wherein composition(s) are provided in one or more pre-filled containers which facilitate administration of the compositions by drops, such as, e.g., one or more pre-filled dropper bottles as described herein. In certain aspects, the invention provides a kit wherein at least one component of a composition is provided separately from at least one other component of a composition, such that components are mixed to form a composition in a form suitable for administration. For example, in aspects, the invention provides kits comprising components of a composition other than a carrier provided in, e.g., a dry form, separate from a carrier component. In aspects, a carrier component is mixed with the dry form components which results in a composition suitable and ready for administration to a recipient. In aspects, a kit comprises any/all necessary tool(s), container(s), or device to facilitate any required combination or mixing of two or more components prior to use.

In aspects, the invention provides for a kit as described in this section, wherein the kit has a shelf life when stored at about room temperature, such as, e.g., about 25° C.+/−~2° C. (or as otherwise described herein), for at least about 1 month, e.g., ~2, ~3, ~4, ~5, or at least about 6 months (e.g., 6-24 mos.).

According to aspects, the invention provides the kit of any of the preceding paragraphs, wherein the composition is made by a process described elsewhere herein.

EXEMPLARY ASPECTS OF THE INVENTION

The following is a non-limiting list of exemplary aspects of the invention.

In aspects, the invention provides a pharmaceutically acceptable and ophthalmologically suitable composition comprising:
  (a) a brinzolamide compound in an amount of between about 0.1 wt. %-about 10 wt. % of the composition;
  (b) a brimonidine compound in an amount of between about 0.01 wt. %-about 0.5 wt. % of the composition; and
  (c) one or more borate-polyol complexes, wherein the total of the one or more borate-polyol complexes are present in an amount of between about 0.5 wt. %-about 6 wt. % of the composition;
wherein the composition demonstrates bioequivalent or detectably or significantly improved pharmacokinetic properties when administered one time or two times per 24-hour period compared to the same one or more pharmacokinetic properties of a reference composition which is substantially similar in ingredients to that of the composition, except with respect to the amount of a penetration enhancement component or a penetration enhancement component constituent, and comprising the same amount of brinzolamide and the same amount of brimonidine, administered three times per 24-hour period (aspect 1).

In aspects, the invention provides the composition of aspect 1, wherein bioequivalence is determined by performance of one or more clinical endpoint studies (aspect 2).

In aspects, the invention provides the composition of aspect 2, wherein the clinical endpoint study is an FDA recommended clinical endpoint study for the treatment of chronic open angle glaucoma and ocular hypertension (aspect 3).

In aspects, the invention provides the composition of any one or both of aspect 2 and aspect 3, wherein the primary endpoint of the clinical endpoint study is the mean difference in intraocular pressure of treated eyes in a test group compared to a reference group at 4 time points, including pre-dose, at 2 hours post administration, after 2 weeks of treatment, and after 6 weeks of treatment with the composition and a corresponding reference product (aspect 4).

In aspects, the invention provides the composition of aspect 4, wherein bioequivalence is established by the clinical endpoint study is established by demonstrating that the limits of each two-sided 95% confidence interval of the treatment difference (test—reference) for mean intraocular pressure of treated eyes at all four time points is within ±1.0 mmHg using the per-protocol (PP) population for the majority of time points measured (aspect 5).

In aspects, the invention provides the composition of any one or more of aspects 1-5, wherein the composition demonstrates equivalent or detectably or significantly improved bioavailability over the bioavailability of a composition comprising the same amount of brinzolamide and the same amount of brimonidine administered three times per 24-hour period (aspect 6).

In aspects, the invention provides the composition of any one or more of aspects 1-6, wherein the composition provides at least one detectably or significantly improved pharmacokinetic property over the same property(ies) provided by a composition comprising the same amount of brinzolamide and the same amount of brimonidine administered three times per 24-hour period (aspect 7).

In aspects, the invention provides the composition of any one or more of aspects 1-7, wherein the composition demonstrates detectably or significantly improved bioavailability over the bioavailability of a composition comprising the same amount of brinzolamide and the same amount of brimonidine administered three times per 24-hour period (aspect 8).

In aspects, the invention provides the composition of any one or more of aspects 1-8, wherein the brinzolamide compound is present in the composition in an amount of about 0.5-about 5 wt. % (aspect 9).

In aspects, the invention provides the composition of any one or more of aspects 1-9, wherein the brinzolamide compound is present in the composition in an amount of about 0.5-about 2 wt. % (aspect 10).

In aspects, the invention provides the composition of any one or more of aspects 1-10, wherein the brinzolamide compound is present in the composition in an amount of about 1 wt. % (aspect 11).

In aspects, the invention provides the composition of any one or more of aspects 1-11, wherein the brinzolamide compound is brinzolamide (aspect 12).

In aspects, the invention provides the composition of any one or more of aspects 1-12, wherein the brimonidine compound is present in the composition in an amount of between about 0.05-about 0.3 wt. % (aspect 13).

In aspects, the invention provides the composition of any one or more of aspects 1-13, wherein the brimonidine compound is present in the composition in an amount of between about 0.1-about 0.3 wt. % (aspect 14).

In aspects, the invention provides the composition of any one or more of aspects 1-14, wherein the brimonidine compound is present in the composition an amount of about 0.2 wt. % (aspect 15).

In aspects, the invention provides the composition of any one or more of aspects 1-15, wherein the brimonidine compound is brimonidine tartrate (aspect 16).

In aspects, the invention provides the composition of any one or more of aspects 1-16, wherein the ratio of the brimonidine compound to the brinzolamide compound in the composition is about 1000:1-about 1:5 (aspect 17).

In aspects, the invention provides the composition of aspect 17, wherein the ratio of the brimonidine compound to the brinzolamide compound in the composition is about 10:1-about 1:5 (aspect 18).

In aspects, the invention provides the composition of any one or both of aspect 17 and aspect 18, wherein the ratio of the brimonidine compound to the brinzolamide compound in the composition is about 5:1 (aspect 19).

In aspects, the invention provides the composition of any one or more of aspects 1-19, wherein the composition comprises brinzolamide in an amount of between about 0.5-about 2 wt. % and brimonidine tartrate in an amount of between about 0.1-about 0.3 wt. % (aspect 20).

In aspects, the invention provides the composition of any one or more of aspects 1-20, wherein the molar ratio of borate to polyol present in the composition is between about 1:0.1-about 1:10 (aspect 21).

In aspects, the invention provides the composition of any one or more of aspects 1-21, wherein the molar ratio of borate to polyol present in the composition is between about 1:0.25-about 1:2.5 (aspect 22).

In aspects, the invention provides the composition of any one or more of aspects 1-22, wherein the composition comprises one or more polyols which form a borate-polyol complex, and wherein the one or more polyols forming the borate-polyol complex is/are selected from the group consisting of one or more of mannitol, glycerin, propylene glycol, and sorbitol (aspect 23).

In aspects, the invention provides the composition of aspect 23, wherein the concentration of borate-polyol complex(es) in the composition is between about 0.5-about 3 wt. % (aspect 24).

In aspects, the invention provides the composition of aspect 24, wherein the concentration of borate-polyol complex(es) in the composition is between about 1-about 2.5 wt. % (aspect 25).

In aspects, the invention provides the composition of aspect 25, wherein the concentration of borate-polyol complex(es) in the composition is between about 1-about 2 wt. % (aspect 26).

In aspects, the invention provides the composition of any one or more of aspects 21-26, wherein the composition comprises boric acid in an amount of about 0.1-about 0.5 wt. % (aspect 27).

In aspects, the invention provides the composition of any one or more of aspects 1-27, wherein the composition comprises an effective amount of one or more compounds which detectably or significantly increase the penetration into ocular tissue of the brinzolamide compound, the brimonidine compound, or both over the penetration of the brinzolamide compound, brimonidine compound, or both in a composition comprising the same amount of brinzolamide compound, brimonidine compound, or both without the one or more penetration-enhancing compound(s) (aspect 28).

In aspects, the invention provides the composition of aspect 28, wherein the one or more penetration-enhancing compound(s) comprises one or more of a water-soluble synthetic polymer, a polyoxyl castor oil, a fatty acid ester including fatty acid ester derivatives, polyoxyethylene fatty ethers, quaternary ammonium compounds, or compounds belonging to two or more such groups (aspect 29).

In aspects, the invention provides the composition of any one or both of aspect 28 or 29, wherein the composition comprises one or more quaternary ammonium compounds (aspect 30).

In aspects, the invention provides the composition of any one or more of aspects 28-30, wherein the composition comprises one or more quaternary ammonium compounds selected from a group comprising a quaternary ammonium salt (aspect 31).

In aspects, the invention provides the composition of aspect 31, wherein the quaternary ammonium salt is selected from a group comprising benzethonium chloride, benzyltrimethylammonium chloride, cetalkonium chloride, cetrimide, cetrimonium bromide, cetylpyridinium chloride, stearalkonium chloride, lauryltrimethylammonium chloride, and benzalkonium chloride (aspect 32).

In aspects, the invention provides the composition of aspect 32, wherein the quaternary ammonium salt is benzalkonium chloride (BKC) (aspect 33).

In aspects, the invention provides the composition of any one or both of aspect 32 or 33, wherein the composition comprises BKC in an amount of at least 0.005 wt. % (aspect 34).

In aspects, the invention provides the composition of any one of aspects 32-34, wherein the composition comprises BKC in an amount of at least 0.005 wt. % but less than 0.02 wt. % (aspect 35).

In aspects, the invention provides the composition of any one of aspects 32-35, wherein the composition comprises BKC in an amount of between about 0.005-about 0.009 wt. % (aspect 36).

In aspects, the invention provides the composition of any one or more of aspects 32-36, wherein the composition comprises BKC in an amount of about 0.007 wt. % (aspect 37).

In aspects, the invention provides the composition of any one or more of aspects 28-37, wherein the composition has a greater bioavailability of the brimonidine compound than an FDA approved reference product composition comprising the same amount of brimonidine compound, the same amount of brinzolamide compound, and 0.003 wt. % of benzalkonium chloride (BKC) (aspect 38).

In aspects, the invention provides the composition of any one or more of aspects 28-38, wherein the composition has a greater bioavailability of the brimonidine compound than the FDA approved reference product composition Simbrinza® comprising the same amount of brimonidine compound, the same amount of brinzolamide compound, and 0.003 wt. % of benzalkonium chloride (BKC) (aspect 39).

In aspects, the invention provides the composition of any one or more of aspects 28-39, wherein the composition has a greater bioavailability of the brinzolamide compound than an FDA approved reference product composition comprising the same amount of brimonidine compound, the same amount of brinzolamide compound, and 0.003 wt. % of benzalkonium chloride (BKC) (aspect 40).

In aspects, the invention provides the composition of any one or more of aspects 28-40, wherein the composition has a greater bioavailability of the brinzolamide compound than the FDA approved reference product composition (Simbrinza®) comprising the same amount of brimonidine compound, the same amount of brinzolamide compound, and 0.003 wt. % of benzalkonium chloride (BKC) (aspect 41).

In aspects, the invention provides the composition of any one or more of aspects 28-41, wherein the composition has a greater bioavailability of both the brimonidine compound and the brinzolamide compound than an FDA approved reference product composition comprising the same amount of brimonidine compound, the same amount of brinzolamide compound, and 0.003 wt. % of benzalkonium chloride (BKC) (aspect 42).

In aspects, the invention provides the composition of any one or more of aspects 28-42, wherein the composition has a greater bioavailability of both the brimonidine compound and the brinzolamide compound than the FDA approved reference product composition (Simbrinza®) comprising the same amount of brimonidine compound, the same amount of brinzolamide compound, and 0.003 wt. % of benzalkonium chloride (BKC) (aspect 43).

In aspects, the invention provides the composition of any one or more of aspects 28-43, wherein one or more penetration-enhancer compounds also provides a detectable or significant preservation effect (aspect 44).

In aspects, the invention provides the composition of aspect 44, wherein the composition comprises BKC in an amount of between about 0.005-about 0.02 wt. % and wherein the composition comprises a detectably or significantly greater stability (as measured by a standard FDA stability testing protocol) of the brimonidine compound, the brinzolamide compound, or both the brimonidine compound and the brinzolamide compound than that of an FDA approved reference produce composition comprising the same amount of brimonidine compound, the same amount of brinzolamide compound, and 0.003 wt. % of BKC (aspect 45).

In aspects, the invention provides the composition of any one or both of aspect 44 or aspect 45, wherein the composition comprises BKC in an amount of between about 0.005-about 0.02 wt. % and wherein the composition comprises a detectably or significantly greater stability (as measured by a standard FDA stability testing protocol) of the brimonidine compound, the brinzolamide compound, or both the brimonidine compound and the brinzolamide compound than that of the FDA approved reference produce composition (Simbrinza®) comprising the same amount of brimonidine compound, the same amount of brinzolamide compound, and 0.003 wt. % of BKC (aspect 46).

In aspects, the invention provides the composition of any one or more of aspects 1-46, wherein the pH of the composition is between about 4.0-about 7.5 (aspect 47).

In aspects, the invention provides the composition of any one or more of aspects 1-47, wherein the osmolality of the composition is between about 200-about 450 mOsm/kg (aspect 48).

In aspects, the invention provides the composition of any one or more of aspects 1-48, wherein the composition further comprises one or more pharmaceutically acceptable excipients (aspect 49).

In aspects, the invention provides the composition of any one or more of aspects 1-49, wherein the one or more pharmaceutically acceptable excipients comprises one or more of a viscosity enhancer, suspending agent, surfactant, solubilizer, tonicity agent, chelating agent, buffering agent, pH adjusting agent, preservative, carrier, or a combination of any or all thereof (aspect 50).

In aspects, the invention provides the composition of any one or both of aspect 49 or aspect 50, wherein the composition comprises a solubilizer selected from tyloxapol, polysorbate-80, tocopherol polyethylene glycol succinate (TPGS), polyoxyl-35 castor oil, poly-arginine, polyserine, tromethamine (tris), sesame seed oil, or a combination of any or all thereof (aspect 51).

In aspects, the invention provides the composition of any one or more of aspects 49-51, wherein the composition comprises a tonicity agent (aspect 52).

In aspects, the invention provides the composition of aspect 52, wherein the tonicity agent is sodium chloride (aspect 53).

In aspects, the invention provides the composition of any one or more of aspects 1-53, wherein the composition is in the form of a suspension comprising:
(a) a brinzolamide compound in an amount of between about 0.1-about 10 wt. % of the composition;
(b) a brimonidine compound in an amount of between about 0.01-about 0.5 wt. % of the composition;
(c) boric acid in an amount of between about 0.1-about 0.5 wt. % of the composition;
(d) a viscosity-enhancing component in an amount of between about 0.1-about 0.7 wt. % of the composition;
(e) one or more polyols capable of forming a borate-polyol complex in an amount of between about 0.6-about 2.2 wt. % of the composition;
(f) a tonicity component in an amount of between about 0.1-about 0.5 wt. % of the composition;
(g) a penetration enhancer component in a total amount of between about 0.02-0.07 wt. % of the composition; and
(h) a carrier (aspect 54).

In aspects, the invention provides the composition of aspect 54, wherein the brinzolamide compound is brinzolamide and the brinzolamide is present in the composition in an amount of about 0.1 wt. % of the composition (aspect 55).

In aspects, the invention provides the composition of aspect 55, wherein the brimonidine compound is brimonidine or a pharmaceutically acceptable salt thereof and is present in the composition in an amount of about 0.2 wt. % of the composition (aspect 56).

In aspects, the invention provides the composition of aspect 56, wherein the brimonidine or pharmaceutically acceptable salt thereof is brimonidine tartrate (aspect 57).

In aspects, the invention provides the composition of any one or more of aspects 54-57, wherein the composition comprises boric acid in an amount of about 0.3 wt. % of the composition (aspect 58).

In aspects, the invention provides the composition of any one or more of aspects 54-58, wherein the composition comprises one or more compounds characterizable as a solubilizer selected from a group consisting of benzalkonium chloride, tyloxapol, polysorbate-80, tocopherol polyethylene glycol succinate (TPGS), polyoxyl-35 castor oil, poly-arginine, polyserine, tromethamine (tris), sesame seed oil, or a combination of any or all thereof (aspect 59).

In aspects, the invention provides the composition of aspect 59, wherein the composition comprises benzalkonium chloride and tyloxapol (aspect 60).

In aspects, the invention provides the composition of aspect 60, wherein the composition comprises the compounds benzalkonium chloride and tyloxapol which provide detectable or significant penetration enhancement effect of a brinzolamide compound, a brimonidine compound, or both a brinzolamide compound and a brimonidine compound, however, neither benzalkonium chloride nor tyloxapol provide detectable or significant solubilization effect for any brinzolamide compound, brimonidine compound, or both any brinzolamide or brimonidine compound (aspect 61).

In aspects, the invention provides the composition of aspect 61, wherein the tyloxapol is present in the composition in an amount of about 0.025 wt. % (aspect 62).

In aspects, the invention provides the composition of any one or more of aspects 54-62, wherein the viscosity-enhancing component comprises a polymer containing hydrophilic groups, such as monosaccharides and polysaccharides comprising ethylene oxide groups, hydroxyl groups, carboxylic acids, or other charged functional groups (aspect 63).

In aspects, the invention provides the composition of aspect 63, wherein the composition comprises a viscosity-enhancing agent selected from a group consisting of a carboxyvinyl polymer, xanthan gum, gelan gum, sodium carboxymethyl cellulose, hydroxypropylmethylcellulose, povidone, polyvinyl alcohol, polyethylene glycol, and alginic acid (aspect 64).

In aspects, the invention provides the composition of aspect 64, wherein the composition comprises a carboxyvinyl polymer comprising carboxylic acid functional groups (aspect 65).

In aspects, the invention provides the composition of aspect 65, wherein the carboxylic acid functional groups of the carboxyvinyl polymer comprise between about 2 to about 7 carbon atoms per functional group (aspect 66).

In aspects, the invention provides the composition of any one or more of aspects 63-66, wherein the viscosity-enhancing agent is a carbomer selected from Carbopol 934P, Carbopol 940, and Carbopol 974P (carbomer 974P) (aspect 67).

In aspects, the invention provides the composition of any one or more of aspects 63-67, wherein the composition comprises a carbomer in an amount of about 0.4 wt. % (aspect 68).

In aspects, the invention provides the composition of aspect 68, wherein the carbomer is Carbopol 974P (carbomer 974P) (aspect 69).

In aspects, the invention provides the composition of any one or more of aspects 54-69, wherein the composition comprises one or more polyols selected from a group consisting of sugars, sugar alcohols, sugar acids, and uronic acids (aspect 70).

In aspects, the invention provides the composition of aspect 70, wherein the one or more polyols is selected from a group consisting of mannitol, glycerin, propylene glycol, and sorbitol (aspect 71).

In aspects, the invention provides the composition of aspect 71, wherein the composition comprises propylene glycol and mannitol (aspect 72).

In aspects, the invention provides the composition of any one or both of aspect 71 or aspect 72, wherein the composition comprises propylene glycol in an amount of between about 0.5-about 1.2 wt. % of the composition (aspect 73).

In aspects, the invention provides the composition of aspect 73, wherein the composition comprises propylene glycol in an amount of about 0.75 wt. % of the composition (aspect 74).

In aspects, the invention provides the composition of any one or more of aspects 71-74, wherein the composition comprises mannitol in an amount of between about 0.1-about 1 wt. % of the composition (aspect 75).

In aspects, the invention provides the composition of aspect 75, wherein the composition comprises mannitol in an amount of about 0.3 wt. % of the composition (aspect 76).

In aspects, the invention provides the composition of any one or more of aspects 70-76, wherein the composition comprises propylene glycol in an amount of about 0.75 wt. % and mannitol in an amount of about 0.3 wt. % of the composition (aspect 77).

In aspects, the invention provides the composition of any one or more of aspects 54-77, wherein the composition comprises boric acid in an amount of about 0.3 wt. % of the composition, propylene glycol in an amount of about 0.75 wt. % of the composition, and mannitol in an amount of about 0.3 wt. % of the composition (aspect 78).

In aspects, the invention provides the composition of any one or more of aspects 54-78, wherein the composition comprises a tonicity agent selected from the group consisting of sodium chloride, glycerin, mannitol, sorbitol, and other electrolytes (aspect 79).

In aspects, the invention provides the composition of aspect 79, wherein the tonicity agent is sodium chloride (aspect 80).

In aspects, the invention provides the composition of aspect 80, wherein the sodium chloride is present in the composition in an amount of about 0.025 wt. % of the composition (aspect 81).

In aspects, the invention provides the composition of any one or more of aspects 54-81, wherein the penetration enhancer is selected from a group comprising one or more of a water-soluble synthetic polymer, a polyoxyl castor oil, fatty acid esters including fatty acid ester derivatives, polyoxyethylene fatty ethers, quaternary ammonium compounds, or compounds belonging to two or more such groups (aspect 82).

In aspects, the invention provides the composition of aspect 82, wherein the composition comprises a quaternary ammonium compound (aspect 83).

In aspects, the invention provides the composition of any one or both of aspect 82 or aspect 83, wherein the composition comprises one or more quaternary ammonium compounds selected from a group comprising a quaternary ammonium salt (aspect 84).

In aspects, the invention provides the composition of aspect 84, wherein the quaternary ammonium salt is selected from a group comprising benzethonium chloride, benzyltrimethylammonium chloride, cetalkonium chloride, cetrimide, cetrimonium bromide, cetylpyridinium chloride, stearalkonium chloride, lauryltrimethylammonium chloride, and benzalkonium chloride (aspect 85).

In aspects, the invention provides the composition of aspect 85, wherein the quaternary ammonium salt comprises, generally consists of, consists essentially of, or is benzalkonium chloride (aspect 86).

In aspects, the invention provides the composition of aspect 86, wherein the benzalkonium chloride is present in an amount of between about 0.004-about 0.015 wt. % of the composition (aspect 87).

In aspects, the invention provides the composition of aspect 87, wherein the benzalkonium chloride is present in an amount of between about 0.005-about 0.01 wt. % of the composition (aspect 88).

In aspects, the invention provides the composition of aspect 88, wherein the benzalkonium chloride is present in the composition in an amount of about 0.006-about 0.009 wt. % of the composition (aspect 89).

In aspects, the invention provides the composition of aspect 89, wherein the benzalkonium chloride is present in the composition in an amount of about 0.006-about 0.008 wt. % of the composition (aspect 90).

In aspects, the invention provides the composition of aspect 90, wherein the benzalkonium chloride is present in the composition in an amount of about 0.007 wt. % of the composition (aspect 91).

In aspects, the invention provides the composition of any one or more of aspects 54-91, wherein the composition comprises water as a carrier, such that the composition is an aqueous suspension (aspect 92).

In aspects, the invention provides the composition of aspect 92, wherein the composition is at least 70 wt. % water (aspect 93).

In aspects, the invention provides the composition of aspect 93, wherein the composition is at least 85 wt. % water (aspect 94).

In aspects, the invention provides the composition of any one or more of aspects 1-94, wherein the composition retains at least 90 wt. % of the potency of the brinzolamide compound when stored at 25° C. and 60% relative humidity or at 40° C. and 75% relative humidity for at least about 1 month (aspect 95).

In aspects, the invention provides the composition of any one or more of aspects 1-95, wherein the composition retains at least 90 wt. % of the potency of the brinzolamide compound when stored at 25° C. and 60% relative humidity or at 40° C. and 75% relative humidity for at least about 2 months (aspect 96).

In aspects, the invention provides the composition of any one or more of aspects 1-96, wherein the composition retains at least 90 wt. % of the potency of the brinzolamide compound when stored at 25° C. and 60% relative humidity or at 40° C. and 75% relative humidity for at least about 3 months (aspect 97).

In aspects, the invention provides the composition of any one or more of aspects 1-97, wherein the composition retains at least 90 wt. % of the potency of the brimonidine compound when stored at 25° C. and 60% relative humidity or at 40° C. and 75% relative humidity for at least about 1 month (aspect 98).

In aspects, the invention provides the composition of any one or more of aspects 1-98, wherein the composition retains at least 90 wt. % of the potency of the brimonidine compound when stored at 25° C. and 60% relative humidity or at 40° C. and 75% relative humidity for at least about 2 months (aspect 99).

In aspects, the invention provides the composition of any one or more of aspects 1-99, wherein the composition retains at least 90 wt. % of the potency of the brimonidine compound when stored at 25° C. and 60% relative humidity or at 40° C. and 75% relative humidity for at least about 3 months (aspect 100).

In aspects, the invention provides the composition of any one or more of aspects 1-100, wherein the composition retains at least 90 wt. % of the potency of the brinzolamide compound and the brimonidine compound when stored at 25° C. and 60% relative humidity or at 40° C. and 75% relative humidity for at least about 1 month (aspect 101).

In aspects, the invention provides the composition of any one or more of aspects 1-101, wherein the composition retains at least 90 wt. % of the potency of the brinzolamide compound and the brimonidine compound when stored at 25° C. and 60% relative humidity or at 40° C. and 75% relative humidity for at least about 2 months (aspect 102).

In aspects, the invention provides the composition of any one or more of aspects 1-102, wherein the composition retains at least 90 wt. % of the potency of the brinzolamide compound and the brimonidine compound when stored at 25° C. and 60% relative humidity or at 40° C. and 75% relative humidity for at least about 3 months (aspect 103).

In aspects, the invention provides the composition of any one or more of aspects 1-103, wherein the composition maintains a level of total impurities below that required by the United States Food and Drug Administration (aspect 104).

In aspects, the invention provides the composition of any one or more of aspects 1-104, wherein the composition is provided in the form of an ophthalmologically suitable suspension, ophthalmologically suitable dispersion, or ophthalmologically suitable solution (aspect 105).

In aspects, the invention provides the composition of aspect 105, wherein the composition is provided as an ophthalmologically suitable suspension (aspect 106).

In aspects, the invention provides the composition of any one or more of aspects 1-106, wherein the composition is administered by drops to a mammalian eye (aspect 107).

In aspects, the invention provides the composition of aspect 107, wherein the composition is administered by the application of 1-3 drops one to three times per day to a mammalian eye (aspect 108).

In aspects, the invention provides the composition of aspect 108, wherein the composition is administered by the application of 1-3 drops one to two times per day to a mammalian eye (aspect 109).

In aspects, the invention provides the composition of aspect 109, wherein the composition is administered by the application of 1-3 drops once per day to a mammalian eye (aspect 110).

In aspects, the invention provides the composition of any one or more of aspects 105-110, wherein the composition provides a reduction in the total amount of brinzolamide compound administered per 24 hour period, total amount of brimonidine compound administered per 24 hour period, total amount of brinzolamide compound and total amount of brimonidine compound administered per 24 hour period, the frequency of dosing per 24 hour period, or any combination thereof compared to the FDA approved reference product Simbrinza® (aspect 111).

In aspects, the invention provides the composition of any one or more of aspects 1-111, wherein the composition is administered to a mammalian eye to treat one or more of irritation of the cornea, irritation of ocular tissue adjacent the cornea, dry eye, glaucoma, or ocular hypertension (elevated intraocular pressure (IOP)) (aspect 112).

In aspects, the invention provides the composition of aspect 112, wherein the composition is administered to a mammalian eye to reduce elevated intraocular pressure (IOP), in patients diagnosed with open-angle glaucoma, ocular hypertension, or both (aspect 113).

In aspects, the invention provides the composition of any one or more of aspects 1-113, wherein the composition detectably or significantly reduces intraocular pressure (IOP) when administered in a dose of 1-3 drops 1-3 times per day (aspect 114).

In aspects, the invention provides the composition of aspect 114, wherein the composition detectably or significantly reduces intraocular pressure (IOP) when administered in a dose of 1-3 drops 1-2 times per day (aspect 115).

In aspects, the invention provides the composition of aspect 115, wherein the composition detectably or significantly reduces intraocular pressure (IOP) when administered in a dose of 1-2 drops 1-2 times per day (aspect 116).

In aspects, the invention provides the composition of aspect 116, wherein the composition detectably or significantly reduces intraocular pressure (IOP) when administered in a dose of a single drop 1-2 times per day (aspect 117).

In aspects, the invention provides the composition of aspect 117, wherein the composition detectably or significantly reduces intraocular pressure (IOP) when administered in a dose of a single drop once per day (aspect 118).

In aspects, the invention provides the composition of any one or more of aspects 112-118, wherein use of composition results in detectably or significantly fewer adverse events than that of a reference product comprising the same amount of brinzolamide compound, the same amount of brimonidine compound, and 0.003 wt. % of benzalkonium chloride administered as one drop three times per day (aspect 119).

In aspects, the invention provides a pharmaceutically acceptable and ophthalmologically suitable composition comprising:
- (a) a pharmaceutically acceptable and ophthalmologically suitable brinzolamide compound in an amount of between about 0.1 wt. %-about 10 wt. % of the composition;
- (b) a pharmaceutically acceptable and ophthalmologically suitable brimonidine compound in an amount of between about 0.01 wt. %-about 0.5 wt. % of the composition; and
- (c) one or more pharmaceutically acceptable and ophthalmologically suitable borate-polyol complexes, wherein the total of the one or more borate-polyol complexes are present in an amount of between about 0.5 wt. %-about 6 wt. % of the composition; and
- (d) benzalkonium chloride in an amount of between 0.005-about 0.02 wt. % of the composition (aspect 120).

In aspects, the invention provides the composition of aspect 120, wherein the composition has any one or more of the characteristics of any one or more of aspects 2-119 (aspect 121).

In aspects, the invention provides a method of treating irritation of the cornea, irritation of ocular tissue adjacent the cornea, dry eye, glaucoma, including open angle glaucoma, or ocular hypertension (elevated intraocular pressure (IOP), comprising administration of a pharmaceutically acceptable and ophthalmologically suitable composition comprising
- (a) a pharmaceutically acceptable and ophthalmologically suitable brinzolamide compound in an amount of between about 0.1 wt. %-about 10 wt. % of the composition;
- (b) a pharmaceutically acceptable and ophthalmologically suitable brimonidine compound in an amount of between about 0.01 wt. %-about 0.5 wt. % of the composition; and
- (c) one or more pharmaceutically acceptable and ophthalmologically suitable borate-polyol complexes, wherein the total of the one or more borate-polyol complexes are present in an amount of between about 0.5 wt. %-about 6 wt. % of the composition;

wherein the method results in bioequivalent or detectably or significantly improved pharmacokinetic properties when administered one time or two times per 24-hour period compared to the same one or more pharmacokinetic properties of a composition comprising the same amount of brinzolamide and the same amount of brimonidine administered three times per 24-hour period (aspect 122).

In aspects, the invention provides the method of aspect 122, wherein the composition has any one or more of the characteristics of aspects 1-121, optionally wherein bioequivalence is determined by performance of one or more clinical endpoint studies, such as studies having one or more characteristics described in one or more of aspects 3-5 (aspect 123).

In aspects, the invention provides a method of treating irritation of the cornea, irritation of ocular tissue adjacent the cornea, dry eye, glaucoma, including open angle glaucoma, or ocular hypertension (elevated intraocular pressure (IOP), comprising administration of a pharmaceutically acceptable and ophthalmologically suitable composition comprising:
- (a) a pharmaceutically acceptable and ophthalmologically suitable brinzolamide compound in an amount of between about 0.1 wt. %-about 10 wt. % of the composition;
- (b) a pharmaceutically acceptable and ophthalmologically suitable brimonidine compound in an amount of between about 0.01 wt. %-about 0.5 wt. % of the composition; and
- (c) one or more pharmaceutically acceptable and ophthalmologically suitable borate-polyol complexes, wherein the total of the one or more borate-polyol complexes are present in an amount of between about 0.5 wt. %-about 6 wt. % of the composition; and
- (d) benzalkonium chloride in an amount between 0.005-about 0.02 wt. % of the composition (aspect 124).

In aspects, the invention provides the method of aspect 124, wherein the composition comprises any one or more of the characteristics of aspects 1-121 (aspect 125).

In aspects, the invention provides the method of any one or more of aspects 122-125, wherein the peak ocular hypotensive effect of the brinzolamide occurs earlier than 3 hours post-dosing (aspect 126).

In aspects, the invention provides the method of aspect 126, wherein the peak ocular hypotensive effect of the brinzolamide occurs earlier than 2.5 hours post-dosing (aspect 127).

In aspects, the invention provides the method of aspect 127, wherein the peak ocular hypotensive effect of the brinzolamide occurs earlier than 2 hours post-dosing (aspect 128).

In aspects, the invention provides the method of any one or more of aspects 122-128, wherein the peak ocular hypotensive effect of the brimonidine occurs earlier than 2 hours post-dosing (aspect 129).

In aspects, the invention provides the method of aspect 129, wherein the peak ocular hypotensive effect of the brimonidine occurs earlier than 1.5 hours post-dosing (aspect 130).

In aspects, the invention provides the method of aspect 130, wherein the peak ocular hypotensive effect of the brinzolamide occurs earlier than 1-hour post-dosing (aspect 131).

In aspects, the invention provides the method of any one or more of aspects 122-131, wherein the method results in a detectable or significant reduction in one or more adverse events compared to the reference product Simbrinza® or a composition comprising the same amount of brimonidine compound, the same amount of brinzolamide compound, and 0.003 wt. % benzalkonium chloride (aspect 132).

In aspects, the invention provides the method of aspect 132, wherein the one or more adverse events are selected from a group consisting of blurred vision; bitter, sour, or unusual taste; blepharitis; dermatitis; dry eye; foreign body sensation; headache; hyperemia; ocular discharge; ocular discomfort; ocular keratitis; ocular pain; ocular pruritus; rhinitis; allergic reaction; alopecia; chest pain; conjunctivitis; diarrhea; diplopia; dizziness; dry mouth/oral dryness; dyspnea; dyspepsia; eye fatigue; hypertonia; keratoconjunctivitis; keratopathy; kidney pain; lid margin crusting or sticky sensation; nausea pharyngitis; tearing; urticaria; ocular burning and stinging; fatigue/drowsiness; conjunctival follicles; corneal staining; corneal erosion; photophobia; eyelid erythema; upper respiratory symptom(s); eyelid edema; conjunctival edema; ocular irritation; gastrointestinal symptoms; asthenia; conjunctival blanching; abnormal vision; and muscle pain (aspect 133).

In aspects, the invention provides a method for manufacturing a composition of any one or more of aspects 1-121, wherein the method comprises:
(a) mixing one or more tonicity agents, one or more polyols, boric acid, one or more penetration enhancers, and one or more viscosity-enhancing compounds, in order, ensuring complete dissolution of one prior to the addition of the next;
(b) filtering the composition resulting from (a);
(c) adjusting the pH of the composition resulting from (b);
(d) sterilizing the composition resulting from (c);
(e) forming a solution of at least one solubilizer compound and a pharmaceutically acceptable and ophthalmologically suitable brimonidine compound, added in order, ensuring the dissolution of the at least one solubilizer compound prior to the addition of the brimonidine;
(f) sterilizing the composition resulting from (e);
(g) forming a slurry by adding a pharmaceutically acceptable and ophthalmologically suitable brinzolamide compound to the composition resulting from (f);
(h) homogenizing the slurry resulting from (g) for a period of about 1-about 3 hours or until a target particle size is achieved; and
(i) transferring the homogenized slurry resulting from (h) to the composition of (d) (aspect 134).

In aspects, the invention provides the method of aspect 134, wherein the one or more tonicity agents comprise sodium chloride; the one or more polyol compounds comprise mannitol and propylene glycol; the one or more penetration enhancers comprise benzalkonium chloride; the one or more viscosity-enhancing agents comprises a carbomer; and the one or more solubilizing agents comprise tyloxapol (aspect 135).

In aspects, the invention provides the composition of any one or both of aspect 134 or 135, wherein the process results in an average particle size of brimonidine and brinzolamide of between about 1-about 3 µm (aspect 136).

In aspects, the invention provides a process for preparing a composition of any one or more of aspects 1-121, wherein the composition provides one or more equivalent or improved pharmacokinetic properties of the brimonidine compound, the brinzolamide compound, or both the brimonidine and the brinzolamide compound when administered one time or two times per 24-hour period compared to the same one or more pharmacokinetic properties of a composition comprising the same amount of brinzolamide and the same amount of brimonidine administered three times per 24-hour period (aspect 137).

In aspects, the invention provides the process of any one or more of aspects 134-137, wherein the process comprises a step of sterilization using one or more methods selected from a group consisting of heat sterilization, gaseous sterilization, filtration sterilization, and radiation sterilization (aspect 138).

In aspects, the invention provides the process of any one or more of aspects 134-138, wherein the process further comprises the inclusion of one or more additional excipients (aspect 139).

In aspects, the invention provides a process for preparing a pharmaceutically acceptable and ophthalmologically suitable composition comprising a pharmaceutically acceptable and ophthalmologically suitable brinzolamide compound in an amount of between about 0.1 wt. %-about 10 wt. % of the composition, a pharmaceutically acceptable and ophthalmologically suitable brimonidine compound in an amount of between about 0.01 wt. %-about 0.5 wt. % of the composition, and a pharmaceutically acceptable and ophthalmologically suitable borate-polyol complex in an amount of between about 0.5 wt. %-about 6 wt. % of the composition, wherein the composition provides one or more equivalent or improved pharmacokinetic properties when administered one time or two times per 24-hour period compared to the same one or more pharmacokinetic properties of a composition comprising the same amount of brinzolamide and the same amount of brimonidine administered three times per 24-hour period (aspect 140).

The process of aspect 140, wherein the process comprises the characteristics described in any one or more of aspects 134-140 (aspect 141).

In aspects, the invention provides a process for preparing an ophthalmic composition comprising a pharmaceutically acceptable and ophthalmologically suitable brinzolamide compound in an amount of about 0.1 to about 10.0 wt. %, a pharmaceutically acceptable and ophthalmologically suitable brimonidine compound in an amount of about 0.01 to about 0.5 wt. %, a pharmaceutically acceptable and ophthalmologically suitable borate-polyol complex in an amount of about 0.5 to 6 wt. %, and one or more pharmaceutically acceptable excipients including benzalkonium chloride, wherein the benzalkonium chloride concentration is greater than about 0.005 wt. % but less than about 0.02 wt. % (aspect 142).

In aspects, the invention provides a process according to any one or more of aspects 134-142, wherein the process results in a detectable or significant reduction in the amount of related compounds and impurities associated with the ophthalmic compositions after storage of one month at 25° C. and 60% relative humidity or at 40° C. and 75% relative humidity (aspect 143).

In aspects, the invention provides a process according to any one or more of aspects 134-143, wherein the process results in a detectable or significant reduction in the amount of related compounds and impurities associated with the ophthalmic compositions after storage of two months at 25° C. and 60% relative humidity or at 40° C. and 75% relative humidity (aspect 144).

In aspects, the invention provides a process according to any one or more of aspects 134-144, wherein the process results in a detectable or significant reduction in the amount of related compounds and impurities associated with the ophthalmic compositions after storage of three months at 25° C. and 60% relative humidity or at 40° C. and 75% relative humidity (aspect 145).

In aspects, the invention provides the composition of any one or more of aspects 1-121, wherein the composition is provided in a form ready for administration to a subject (aspect 146).

In aspects, the invention provides the composition of aspect 146, wherein the composition is provided ready for use in a container capable of dispensing the composition in a drop-by-drop manner to a recipient's eye (aspect 147).

In aspects, the invention provides a kit comprising a pharmaceutically acceptable and ophthalmologically suitable composition of any one or more of aspects 1-121 packaged in one or more containers capable of dispensing the composition by drops to a recipient's eye (aspect 148).

In aspects, the invention provides the kit of aspect 148, wherein the container comprises a total volume of composition of between about 2 mL and about 20 mL (aspect 149).

In aspects, the invention provides the kit of any one or more of aspects 146-149, wherein the composition is made by a process having any one or more of the characteristics of aspects 134-145 (aspect 150).

In aspects, the invention provides a composition of any one or more of aspects 1-121, wherein the composition comprises means for providing detectable or significant preservation effect, as indicated by stability of a brinzolamide compound, a brimonidine compound, or both a brinzolamide compound and a brimonidine compound in the composition, detectably or significantly reducing the amount of detectable or significant impurities, when the composition is stored for at least 1 month at 25° C. and 40% relative humidity or 40° C. and 25% relative humidity ("preservation means") (aspect 151).

In aspects, the invention provides a composition of any one or more of aspects 1-121, wherein the composition comprises means for providing detectable or significant preservation effect, as indicated by stability of a brinzolamide compound, a brimonidine compound, or both a brinzolamide compound and a brimonidine compound in the composition, detectably or significantly reducing the amount of detectable or significant impurities, when the composition is stored for at least 2 months at 25° C. and 40% relative humidity or 40° C. and 25% relative humidity ("preservation means") (aspect 152).

In aspects, the invention provides a composition of any one or more of aspects 1-121, wherein the composition comprises means for providing detectable or significant preservation effect, as indicated by stability of a brinzolamide compound, a brimonidine compound, or both a brinzolamide compound and a brimonidine compound in the composition, detectably or significantly reducing the amount of detectable or significant impurities, when the composition is stored for at least 3 months at 25° C. and 40% relative humidity or 40° C. and 25% relative humidity ("preservation means") (aspect 153).

In aspects, the invention provides a composition of any one or more of aspects 1-121, wherein the composition comprises means for providing detectable or significant preservation effect, as indicated by stability of a brinzolamide compound, a brimonidine compound, or both a brinzolamide compound and a brimonidine compound in the composition, detectably or significantly reducing the amount of detectable or significant impurities, when the composition is stored for at least 6 months at 25° C. and 40% relative humidity or 40° C. and 25% relative humidity ("preservation means") (aspect 154).

In aspects, the invention provides a composition of any one or more of aspects 1-121, wherein the composition comprises means for providing detectable or significant preservation effect, as indicated by stability of a brinzolamide compound, a brimonidine compound, or both a brinzolamide compound and a brimonidine compound in the composition, detectably or significantly reducing the amount of detectable or significant impurities, when the composition is stored for at least 1 year at 25° C. and 40% relative humidity or 40° C. and 25% relative humidity ("preservation means") (aspect 155).

In aspects, the invention provides a composition of any one or more of aspects 1-121, wherein the composition comprises means for detectably or significantly enhancing the amount of one or more APIs of the composition penetrating ocular tissue over the course of an established time period, the rate of one or more APIs of the composition penetrating ocular tissue, or both ("penetration means") (aspect 156).

In aspects, the invention provides a composition of any one or more of aspects 1-121, wherein the composition comprises means for detectably or significantly enhancing the viscosity of the composition ("viscosity enhancement means") (aspect 157).

In aspects, the invention provides a composition of any one or more of aspects 1-121, wherein the composition comprises means for detectably or significantly contributing to the tonicity of the composition ("tonicity means") (aspect 158).

In aspects, the invention provides a composition of any one or more of aspects 1-121, wherein the composition comprises means for detectably or significantly maintaining a suspension of an API of the composition for at least about 12 hours without requiring re-suspension ("suspension means") (aspect 159).

In aspects, the invention provides a composition of any one or more of aspects 1-121, wherein the composition comprises means for detectably or significantly maintaining a suspension of an API of the composition for at least about 24 hours ("suspension means") (aspect 160).

In aspects, the invention provides a composition of any one or more of aspects 1-121, wherein the composition comprises means for detectably or significantly maintaining a suspension of an API of the composition for at least about 36 hours ("suspension means") (aspect 161).

In aspects, the invention provides a composition of any one or more of aspects 1-121, wherein the composition comprises means for detectably or significantly maintaining a suspension of an API of the composition for at least about 48 hours ("suspension means") (aspect 162).

In aspects, the invention provides a composition of any one or more of aspects 1-121, wherein the composition comprises means for carrying APIs of the composition ("carrier means") (aspect 163).

In aspects, the invention provides a composition of any one or more of aspects 1-121, wherein the composition comprises means for chelation ("chelation means") (aspect 164).

In aspects, the invention provides a composition of any one or more of aspects 1-121, wherein the composition comprises means for buffering the composition such that it maintains a pH of about 4.0-about 7.0 ("buffering means") (aspect 165).

EXAMPLES

The following detailed Examples are provided to assist readers in further understanding aspects of the invention or principles related to practicing aspects of the invention. The particular materials, methods, steps, and conditions employed/described in the following Examples, and results thereof, are intended to be further illustrative of aspects of the invention. These Examples reflect exemplary embodiments of the invention, and the specific methods, findings, principles of such Examples, and the general implications thereof, can be combined with any other aspect of the invention. However, readers should understand that the invention is not limited by or to any part of the Examples.

Example 1

Table 3 below provides a listing of exemplary ingredients suitable for a pharmaceutically acceptable and ophthalmologically suitable composition provided by the invention, along with exemplary concentrations of such ingredients. Various derivations of compositions provided by Table 3 have been manufactured. Specific data derived from the testing of one such exemplary composition is provided in Example 2. Note that concentrations of ingredients are provided in Table 3 in percent weight/volume (wt/v. %).

TABLE 3

Exemplary Composition(s) Provided by the Invention (with Exemplary Ingredient Concentrations).

| No. | Name of Ingredient | Percentage (weight/volume) (wt/v. %) |
|---|---|---|
| 1 | Brinzolamide | 0.1 to 10 |
| 2 | Brimonidine Tartrate | 0.01 to 0.5 |
| 3 | Benzalkonium chloride | 0.005 to 0.2 |
| 4 | Boric acid | 0.1 to 0.5 |
| 5 | Propylene glycol | 0.5 to 1.2 |
| 6 | Tyloxapol | 0.015 to 0.5 |
| 7 | Carbomer 974P | 0.1 to 0.7 |
| 8 | Mannitol | 0.1 to 1.0 |
| 9 | Sodium chloride | 0.1 to 0.5 |
| 10 | Hydrochloric acid, and/or Sodium Hydroxide | QS to adjust pH approximately 6.5 |
| 11 | Water for Injection | QS to 100% |

Example 2

Exemplary Composition A provided in Table 4 was manufactured according to the manufacturing process provided by this Example.

TABLE 4

Composition A.

| No. | Name of ingredients | Percentage (w/v) (wt/v. %) |
|---|---|---|
| 1 | Brinzolamide | 1 |
| 2 | Brimonidine Tartrate | 0.2 |
| 3 | Benzalkonium chloride | 0.007 |
| 4 | Boric acid | 0.3 |
| 5 | Propylene glycol | 0.75 |
| 6 | Tyloxapol | 0.025 |
| 7 | Carbomer 974P | 0.4 |
| 8 | Mannitol | 0.3 |
| 9 | Sodium chloride | 0.25 |
| 10 | Hydrochloric acid, and/or Sodium Hydroxide | q.s. to adjust pH approximately 6.5 |
| 11 | Water for Injection | QS to 100% |

The following manufacturing process was utilized in the production of Composition A shown in Table 4.

Part I:
1. 65% of the total required water for injection (WFI) was collected in a clean container and was stirred until it reached room temperature (RT).
2. Once at RT, the following ingredients were added to the WFI in order, ensuring that each previous ingredient was in solution prior to the addition of the next.
    a. Sodium chloride
    b. Mannitol
    c. Propylene glycol
    d. Boric acid
    e. Benzalkonium chloride
    f. Carbomer 974P
3. After complete dissolution of the above 6 ingredients, the resulting solution was stirred for 30 minutes.
4. After 30 minutes, the solution was filtered through a 0.2-micron filter into a larger vessel ("main vessel"), a vessel suitable for bulk sterilization.
5. Once in the main vessel, the solution was pH adjusted to 6.8±0.1 using 0.1 N HCl or 0.1 N NaOH.
6. The solution was then brought up to 70% of the total final weight using WFI.
7. After the solution was brought to 70% of its final weight, the main vessel was closed and autoclaved for 20 minutes at 121° C.
8. After autoclaving, the main vessel was allowed to cool to room temperature.

Part II
1. 40% of the remaining required WFI was obtained and cooled under nitrogen purging.

Part III
1. 20% of the remaining required WFI was obtained, and to that WFI, the required quantity of tyloxapol was added and stirred until completely dissolved.
2. Once the tyloxapol was completely in solution, the required amount of brimonidine was added and stirred until completely dissolved.
3. Upon complete dissolution of the brimonidine in the Tyloxapol solution, the solution was sterile filtered into a sterile container connected to a homogenizer.
4. The emptied container resulting from step (3) of Part III was rinsed with 5% of the remaining WFI and the solution resulting from the rinsing was sterile filtered into the sterile container of step 3 of Part III.
5. The required quantity of brinzolamide was then aseptically added to the sterile container of step (4) of Part III to form a slurry.
6. The slurry resulting from step (5) was homogenized for between about one to three hours, during which time small quantity samples of the slurry were aseptically collected to determine the particle size. The homogenization process was continued until the desired average particle size of between about 1.5-2.5 μm was achieved.
7. Once the desired particle size was achieved, the slurry was aseptically transferred to the main vessel of Part I.
8. An additional 5% of the remaining WFI was sterile filtered and used to rinse the tank and homogenizer.
9. The rinsing water from step (9) of Part III was aseptically transferred to the main vessel of Part I.
10. Finally, WFI was added to bring up the volume of the solution to 100% of the final total volume.

Example 3

The composition (Composition B) provided in Table 5 was manufactured according to the manufacturing process provided by this Example. Multiple aliquots of Composition B were then stored at 40° C. and 25% relative humidity and 25° C. and 40% relative humidity for a period of at least 12 months, during which time a series of tests, including stability testing (of active compounds), impurity testing, particle size distribution testing, and pH, viscosity, and osmolality testing as described herein were performed.

TABLE 5

Exemplary Composition B Provided by the Invention.

| Sr. No | Name of ingredients | Percentage (w/v) (wt/v. %) |
|---|---|---|
| 1 | Brinzolamide | 1 |
| 2 | Brimonidine Tartrate | 0.2 |
| 3 | Benzalkonium chloride | 0.005 |
| 4 | Boric acid | 0.3 |
| 5 | Propylene glycol | 0.75 |
| 6 | Tyloxapol | 0.025 |

TABLE 5-continued

Exemplary Composition B Provided by the Invention.

| Sr. No | Name of ingredients | Percentage (w/v) (wt/v. %) |
|---|---|---|
| 7 | Carbomer 974P | 0.4 |
| 8 | Mannitol | 0.3 |
| 9 | Sodium chloride | 0.25 |
| 10 | Hydrochloric acid, and/or Sodium Hydroxide | q.s. to adjust pH approximately 6.5 |
| 11 | Water for Injection | QS to 100% |

The following manufacturing process was utilized in producing Composition B of Table 4.

Part I:
1. 65% of the total required water for injection (WFI) was collected in a clean container and was stirred until it reached room temperature (RT).
2. Once at RT, the following ingredients were added to the WFI in order, ensuring that each previous ingredient was in solution prior to the addition of the next.
   a. Sodium chloride
   b. Mannitol
   c. Propylene glycol
   d. Boric acid
   e. Benzalkonium chloride
   f. Carbomer 974P
3. After complete dissolution of the above 6 ingredients, the resulting solution was stirred for 30 minutes.
4. After 30 minutes, the solution was filtered through a 0.2-micron filter into a larger vessel ("main vessel"), a vessel suitable for bulk sterilization.
5. Once in the main vessel, the solution was pH adjusted to 6.8±0.1 using 0.1 N HCl or 0.1 N NaOH.
6. The solution was then brought up to 70% of the total final weight using WFI.
7. After the solution was brought to 70% of its final weight, the main vessel was closed and autoclaved for 20 minutes at 121° C.
8. After autoclaving, the main vessel was allowed to cool to room temperature.

Part II
1. 40% of the remaining required WFI was obtained and cooled under nitrogen purging.

Part III
1. 20% of the remaining required WFI was obtained, and to that WFI, the required quantity of tyloxapol was added and stirred until completely dissolved.
2. Once the tyloxapol was completely in solution, the required amount of brimonidine was added and stirred until completely dissolved.
3. Upon complete dissolution of the brimonidine in the Tyloxapol solution, the solution was sterile filtered into a sterile container connected to a homogenizer.
4. The emptied container resulting from step (3) of Part III was rinsed with 5% of the WFI and the solution resulting from the rinsing was sterile filtered into the sterile container of step 3 of Part III.
5. The required quantity of brinzolamide was then aseptically added to the sterile container of step (4) of Part III to form a slurry.
6. The slurry resulting from step (5) was homogenized for between about one to three hours, during which time small quantity samples of the slurry were aseptically collected to determine the particle size. The homogenization process was continued until the desired average particle size of between about 1.5-2.5 μm was achieved.
7. Once the desired particle size was achieved, the slurry was aseptically transferred to the main vessel of Part I.
8. An additional 5% of the WFI was sterile filtered and used to rinse the tank and homogenizer.
9. The rinsing water from step (9) of Part III was aseptically transferred to the main vessel of Part I.
10. Finally, WFI was added to bring up the volume of the solution to 100% of the final total volume.

Composition B manufactured according to the process described was subjected to stability testing at 40° C. and 25% relative humidity and 25° C. and 40% relative humidity. Data from stability testing demonstrating the percent of original brinzolamide and brimonidine compound is provided below in Table 6.

TABLE 6

Composition B Stability.

| Condition | Time (Months) | Brinzolamide (Assay %) | Brimonidine (Assay %) |
|---|---|---|---|
| 40° C./25% RH* | 1 | 96.8 | 98.8 |
| | 3 | 96.1 | 97.0 |
| | 6 | 95.7 | 97.1 |
| 25° C./40% RH | Initial | 95.4 | 100.0 |
| | 3 | 94.7 | 97.6 |
| | 6 | —** | — |
| | 12 | 97.3 | 96.8 |

*"RH" = relative humidity; **"—" = data not collected

Stability testing revealed that Composition B maintains greater than 95% of both brinzolamide and brimonidine compounds after storage at 40° C. and 25% relative humidity for at least 6 months and after storage at 25° C. and 40% relative humidity for at least 12 months.

Composition B manufactured according to the process described was also subjected to impurities testing over the course of storage at 40° C. and 25% relative humidity and 25° C. and 40% relative humidity. Data from impurities testing is provided below in Table 7.

TABLE 7

Composition B Stability.

| | | | Brinzolamide (Major Impurities) (%) | | | Brimonidine (Major Impurities) (%) | |
|---|---|---|---|---|---|---|---|
| Condition | Time (Months) | Total Impurities (%) | Imp. B | Imp. E | Imp. G | EP Imp. E | 6 amino quinoxaline/Brimonidine Imp. C. @ RRT* 1.53 |
| 40° C./ 25% RH** | 1 | 0.355 | 0.066 | 0.070 | 0.069 | — | — |
| | 3 | 0.572 | 0.084 | 0.066 | 0.171 | 0.096 | 0.156 |
| | 6 | 1.152 | —*** | — | 0.343 | — | 0.355 |

TABLE 7-continued

Composition B Stability.

| | | | Brinzolamide (Major Impurities) (%) | | Brimonidine (Major Impurities) (%) | | |
|---|---|---|---|---|---|---|---|
| | | | | | | 6 amino quinoxaline/Brimonidine | |
| Condition | Time (Months) | Total Impurities (%) | Imp. B | Imp. E | Imp. G | EP Imp. E | Imp. C. @ RRT* 1.53 |
| 25° C./ | Initial | 0.280 | 0.081 | 0.067 | — | — | — |
| 40% RH | 3 | 0.207 | 0.091 | 0.062 | — | — | — |
| | 6 | — | — | — | — | — | — |
| | 12 | 0.887 | — | — | — | — | — |

*"RRT" = Relative retention time;
**"RH" = relative humidity;
***"—" = Below limit of detection;
"EP" = per European pharmacopeia;
"Imp." = impurity.

Data from impurities testing reveals that compositions tested/evaluated under the provided conditions demonstrate stability for a period of at least about 6 months.

Composition B manufactured according to the process described was also subjected to particle size distribution testing over the course of storage at 40° C. and 25% relative humidity and 25° C. and 40% relative humidity. Data from particle size distribution testing is provided below in Table 8.

TABLE 8

Composition B Particle Size Distribution.

| | | Diameter (micron) | | |
|---|---|---|---|---|
| Condition | Time (months) | D10 | D50 | D90 |
| | 0 | 0.86 | 1.64 | 2.66 |
| 40° C./25% RH** | 1 | 0.74 | 1.68 | 2.83 |
| | 3 | 1.03 | 2.52 | 4.47 |
| | 6 | 1.00 | 2.30 | 4.00 |
| | 0 | 0.86 | 1.64 | 2.66 |
| 25° C./40% RH | 3 | 0.81 | 2.48 | 4.55 |
| | 6 | — | — | — |
| | 12 | 0.80 | 2.30 | 4.90 |

The results provided in Table 9 demonstrate that after 6 months of storage at 40° C. and 25% relative humidity, about 10% of all particles are smaller than about 1 micron; the mean diameter (D50) of particles is about 2.3 microns; and about 90% of all particles are smaller than about 4 microns. Further, the results provided in Table 7 demonstrate that after 12 months of storage at 25° C. and 40% relative humidity, about 10% of all particles are smaller than about 0.8 microns the mean diameter (D50) of particles is about 2.3 microns; and about 90% of all particles are smaller than about 5 microns. This data indicate that Composition B provides adequate particle size stability over the course of storage for the tested periods under tested conditions.

Composition B manufactured according to the process described was also subjected to pH, viscosity, and osmolality testing over the course of storage at 40° C. and 25% relative humidity and 25° C. and 40% relative humidity. Data from pH, viscosity, and osmolality testing on two manufactured batches of Composition B are provided below in Table 8.

TABLE 9 pH, viscosity, and Osmolality testing.

| | | Composition B - Batch 1 | | | Composition B - Batch 2 | | |
|---|---|---|---|---|---|---|---|
| Condition | Time (months) | pH | Viscosity | Osmolality | pH | Viscosity | Osmolality |
| 40° C./25% RH* | 1 | 6.48 | 22.01 | —** | 6.44 | — | 285 |
| | 3 | 6.52 | 24.56 | — | 6.43 | — | 288 |
| | 6 | 6.43 | 32.27 | 282 | 6.44 | — | 297 |
| 25° C./40% RH | Initial | 6.45 | 20.77 | — | 6.45 | — | 284 |
| | 3 | 6.59 | 21.27 | — | 6.47 | — | 284 |
| | 6 | 6.45 | 21.53 | 273 | — | — | — |
| | 12 | — | — | — | 6.58 | — | 279 |

*"RH" = relative humidity;
**"—" = data not collected.

Results from pH, viscosity, and osmolality testing reveals that the pH of composition B remains stable and within an acceptable range both over the course of 6 months of storage at 40° C. and 25% RH and over the course of 12 months of storage 25° C. and 40% RH. Further, results indicate that the viscosity of the compositions, while detectably higher on average when stored at warmer temperatures and lower relative humidity, the viscosity appears to remain stable and within acceptable limits both over the course of 6 months of storage at 40° C. and 25% RH and over the course of 12 months of storage 25° C. and 40% RH. Finally, results of osmolality testing reveal that osmolality remains stable and within acceptable limits both over the course of 6 months of storage at 40° C. and 25% RH and over the course of 12 months of storage 25° C. and 40% RH.

What is claimed is:

1. A method of treating elevated intraocular pressure (IOP) in a mammalian eye comprising administering an effective amount of a pharmaceutically acceptable and ophthalmologically suitable composition to the eye no more than twice per 24-hour period, the composition comprising:
   (a) a pharmaceutically acceptable and ophthalmologically suitable brinzolamide compound in an amount of about 1 wt. %-about 10 wt. % of the composition; and
   (b) a pharmaceutically acceptable and ophthalmologically suitable brimonidine compound in an amount of about 0.02 wt. %-about 0.5 wt. % of the composition, and
   (c) benzalkonium chloride in an amount of 0.007 wt. %-about 0.02 wt. % of the composition, and
   (d) a pharmaceutically acceptable and ophthalmologically suitable borate-polyol complex in an amount of about 0.5 wt. %-about 6 wt. % of the composition wherein the borate-polyol complex comprises two or more polyol compounds, and wherein the ratio of the benzalkonium chloride to the boric acid is between about 1:14 and about 1:43,
   wherein the composition comprises less than 1% nonionic surfactant, and further wherein performing the method results in an effect that (1) is bioequivalent to or (2) results in a greater bioavailability of the brinzolamide compound, the brimonidine compound, or both, than the administration of a reference product comprising the same amount of a brinzolamide compound and the same amount of a brimonidine compound that is administered three times per 24-hour period; and wherein the composition is in the form of an ophthalmic suspension.

2. The method of claim 1, wherein the composition is administered once per day but still results in an effect that is bioequivalent or results in greater bioavailability of the brinzolamide compound, the brimonidine compound, or both, when compared to application of the reference product three times per day.

3. The method of claim 1, wherein the brimonidine compound is brimonidine tartrate.

4. The method of claim 3, wherein the brimonidine tartrate is present in an amount of about 0.2 wt. % of the composition.

5. The method of claim 1, wherein the brinzolamide compound is present in an amount of about 1 wt. % of the composition.

6. The method of claim 1, wherein the two or more polyol compounds participating in the formation of the borate-polyol complex are selected from mannitol, glycerin, propylene glycol, and sorbitol.

7. The method of claim 6, wherein the total amount of the two or more polyol compounds is about 0.6 wt. %-about 2.2 wt. % of the composition.

8. The method of claim 1, wherein the method provides a statistically significant greater bioavailability of the brinzolamide compound, the brimonidine compound, or both as compared to the reference product.

9. The method of claim 8, wherein the reference product comprises 1 wt. % brinzolamide, 0.2 wt. % brimonidine tartrate, 0.003 wt. % benzalkonium chloride, propylene glycol, carbomer, boric acid, mannitol, sodium chloride, tyloxapol, purified water, and optionally hydrochloric acid and sodium hydroxide used to adjust pH.

10. The method of claim 9, wherein the reference product is a product approved by FDA under NDA #204251 as of Oct. 1, 2020.

11. The method of claim 2, wherein the composition has a statistically significant greater bioavailability of the brinzolamide compound, the brimonidine compound, or both as compared to the reference product.

12. The method of claim 11, wherein the reference composition comprises 1 wt. % brinzolamide, 0.2 wt. % brimonidine tartrate, 0.003 wt. % benzalkonium chloride, propylene glycol, carbomer, boric acid, mannitol, sodium chloride, tyloxapol, purified water, and optionally hydrochloric acid and sodium hydroxide used to adjust pH.

13. The method of claim 12, wherein the reference product is a product approved under NDA #204251 as of Oct. 1, 2020.

14. The method of claim 1, wherein the composition further comprises an effective amount of one or more pharmaceutically acceptable excipients comprising a solubilizer, a viscosity enhancer, a tonicity agent, a chelating agent, a buffer, a preservative, and water.

* * * * *